United States Patent [19]

Takeuchi et al.

[11] Patent Number: 5,780,210
[45] Date of Patent: Jul. 14, 1998

[54] COLOR DEVELOPING AGENT, SILVER HALIDE PHOTOGRAPHIC LIGHT-SENSITIVE MATERIAL AND IMAGE FORMING METHOD

[75] Inventors: Kiyoshi Takeuchi; Koki Nakamura; Toshiki Taguchi; Koichi Nakamura; Toshiyuki Makuta, all of Minami-ashigara, Japan

[73] Assignee: Fuji Photo Film Co., Ltd., Kanagawa, Japan

[21] Appl. No.: 601,683

[22] Filed: Feb. 15, 1996

[30] Foreign Application Priority Data

Feb. 15, 1995 [JP] Japan ............................ 7-49287
Nov. 30, 1995 [JP] Japan ............................ 7-334211

[51] Int. Cl.$^6$ ................................. G03C 1/43
[52] U.S. Cl. ............... 430/435; 430/264; 430/448; 430/566
[58] Field of Search ................... 430/542, 566, 430/435, 264, 448

[56] References Cited

U.S. PATENT DOCUMENTS

| | | | |
|---|---|---|---|
| 2,424,256 | 7/1947 | Schmidt et al. | 430/380 |
| 3,285,957 | 11/1966 | Baker et al. | 430/264 |
| 3,342,597 | 9/1967 | Harnish et al. | 430/376 |
| 3,719,492 | 3/1973 | Barr et al. | 430/376 |
| 3,782,949 | 1/1974 | Olivares et al. | 430/218 |
| 4,060,418 | 11/1977 | Waxman et al. | 430/212 |
| 4,481,268 | 11/1984 | Bailey et al. | 430/17 |
| 4,684,604 | 8/1987 | Harder | 430/375 |
| 4,740,453 | 4/1988 | Nakamura et al. | 430/505 |
| 4,978,602 | 12/1990 | Fujita et al. | 564/34 |
| 5,030,546 | 7/1991 | Takamuki et al. | 430/264 |
| 5,147,764 | 9/1992 | Bowne | 430/372 |
| 5,230,983 | 7/1993 | Inoue et al. | 430/264 |
| 5,262,274 | 11/1993 | Katoh | 430/264 |
| 5,273,859 | 12/1993 | Katoh et al. | 430/264 |
| 5,278,025 | 1/1994 | Okamura et al. | 430/264 |
| 5,279,920 | 1/1994 | Onodera et al. | 430/264 |
| 5,286,598 | 2/1994 | Inoue et al. | 430/264 |
| 5,385,816 | 1/1995 | Stanley et al. | 430/544 |
| 5,415,981 | 5/1995 | Clarke et al. | 430/384 |
| 5,416,218 | 5/1995 | Chan et al. | 548/338.1 |
| 5,424,170 | 6/1995 | Sudo et al. | 430/264 |
| 5,441,847 | 8/1995 | Fukawa et al. | 430/264 |
| 5,447,835 | 9/1995 | Sakai et al. | 430/598 |
| 5,629,140 | 5/1997 | Harder et al. | 430/489 |

FOREIGN PATENT DOCUMENTS

| | | |
|---|---|---|
| 0545491 | 6/1993 | European Pat. Off. |
| 0545491A1 | 6/1993 | European Pat. Off. |
| 0565165 | 10/1993 | European Pat. Off. |
| 0565165A1 | 10/1993 | European Pat. Off. |
| 0593110A1 | 4/1994 | European Pat. Off. |
| 1159758 | 12/1963 | Germany . |
| 57-76543 | 5/1982 | Japan . |
| 58-14671 | 3/1983 | Japan . |
| 58-14672 | 3/1983 | Japan . |
| 59-81643 | 5/1984 | Japan . |
| 1-201650 | 8/1989 | Japan . |
| 7-325358 | 12/1995 | Japan . |
| 803783 | 10/1958 | United Kingdom . |
| 1069061 | 5/1967 | United Kingdom . |

OTHER PUBLICATIONS

Database Crossfire, Beilstein Informationssysteme GmbH, Frankfurt DE BRN=3446337, Xp002003474 & Recl. Trav.Chim.Pays–Bas, vol. 55, 1936, pp. 101, 115.
Chemische Berichte, vol. 54, 1921, Weinheim DE, pp. 660–669, XP002003472 W. Borsche: "Uber Cyan–nitro–phenylhydrazine" pp. 662, 665.
Journal of the Chemical Society, Hegarty et al., Hydrolysis of Azoesters . . . . , 1980, pp. 1238–1243.

Primary Examiner—Hoa Van Le
Attorney, Agent, or Firm—Birch, Stewart, Kolasch & Birch, LLP

[57] ABSTRACT

There is disclosed a light-sensitive material comprising, in a hydrophilic colloid provided on a base, a color-developing agent represented by formula (I) or (II):

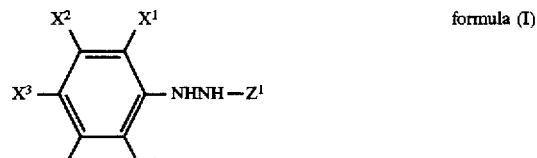

formula (I)

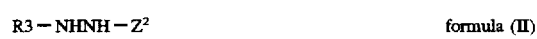

formula (II)

wherein $Z^1$ represents an acyl group, a carbamoyl group, an alkoxycarbonyl group, or an aryloxycarbonyl group; $Z^2$ represents a carbamoyl group, an alkoxycarbonyl group, or an aryloxycarbonyl group; $X^1$, $X^2$, $X^3$, $X^4$, and $X^5$ each represent a hydrogen atom or a substituent, provided that the sum of the Hammett substituent constant σp values of $X^1$, $X^3$, and $X^5$ and the Hammett substituent constant σm values of $X^2$ and $X^4$ is 0.80 or more but 3.80 or below; and $R^3$ represents a heterocyclic group. There is also disclosed a novel color-developing agent that can be built in. By using the color-developing agent, the light-sensitive material can attain a rapid and simple formation of an image.

23 Claims, No Drawings

COLOR DEVELOPING AGENT, SILVER HALIDE PHOTOGRAPHIC LIGHT-SENSITIVE MATERIAL AND IMAGE FORMING METHOD

FIELD OF THE INVENTION

The present invention relates to a silver halide photographic light-sensitive material that uses a novel color-developing agent, and to a novel image-forming method. The present invention particularly relates to a silver halide photographic light-sensitive material good in color-forming properties when developed, and to an image-forming method.

BACKGROUND OF THE INVENTION

In color photographic light-sensitive materials, when the photographic material is exposed to light and color-developed, the oxidized color developer and couplers are reacted, and an image is formed. In this system, color reproduction by the subtractive color process is used, and, to reproduce blue, green, and red colors, images are formed that are yellow, magenta, and cyan in color, complementary to blue, green, and red.

Color development is accomplished by immersing the exposed color photographic material in an aqueous alkali solution in which a color-developing agent is dissolved (a developing solution). However, the color-developing agent in the form of an aqueous alkali solution is unstable and liable to deteriorate with time, and there is the problem that the developing solution must be replenished frequently in order to retain stable developing performance. Further, used developing solutions containing a color-developing agent are required to be discarded, and this, together with the above frequent replenishment, creates a serious problem regarding the treatment of used developing solutions that are discharged in large volume. Thus, low-replenishment and reduced discharge of developing solutions are strongly demanded.

One effective measure for realizing low-replenishment and reduced discharge of developing solutions is a method wherein an aromatic primary amine developing agent or its precursor is built in the hydrophilic colloid layer of a color photographic material. Examples of the developing agents that can be built in include compounds described, for example, in British Patent No. 803,783, U.S. Pat. Nos. 3,342,597, 3,719,492, and 4,060,418, British Patent No. 1,069,061, West Germany Patent No. 1,159,758, JP-B ("JP-B" means examined Japanese patent publication) Nos. 14,671/1983 and 14,672/1983, and JP-A ("JP-A" means unexamined published Japanese patent application) Nos. 76,543/1982 and 81,643/1984. However, color photographic materials having these aromatic primary amine developing agents or their precursors built therein have a defect that satisfactory color formation is not obtained when they are chromogenically developed.

Another effective measure is a method wherein a sulfonylhydrazine-type developing agent is built in the hydrophilic colloid layer of a color photographic material, and examples of the color-developing agent that can be built in include compounds described, for example, in European Patent Nos. 545,491A1 and 565,165A1. However, the developing agents listed therein still cannot give satisfactory color formation when the photographic materials are chromogenically developed, and there is the problem that, when the sulfonylhydrazine-type developing agent is used with a two-equivalent coupler, the color formation is little. In comparison with four-equivalent couplers, two-equivalent couplers have such merits that stain originating in the couplers can be reduced and the activity of the couplers is easily adjusted. Accordingly, a developing agent is strongly desired that can give satisfactory color formation when the photographic material in which the developing agent is built is developed, and that can give an image good in color formation when a two-equivalent coupler is used.

SUMMARY OF THE INVENTION

An object of the present invention is to provide a silver halide color photographic light-sensitive material that, by using a novel color-developing agent, can give satisfactory color formation when the photographic material is developed, and that can give an image good in color formation, even if a two-equivalent coupler is used.

Another object of the present invention is to provide an image-forming method that, by using a novel color-developing agent, can give satisfactory color formation when the photographic material is developed, and that can give an image good in color formation, even if a two-equivalent coupler is used.

Other and further objects, features, and advantages of the invention will appear more evident form the following description.

DETAILED DESCRIPTION OF THE INVENTION

The objects of the present invention can be attained by the following constitution:

(1) A color-developing agent represented by the following formula (I) or (II):

(2) A method of forming an image, comprising developing a silver halide photographic light-sensitive material that has been image-wise exposed to light, in the presence of a color-developing agent represented by formula (I) (which, for example, may be contained in the light-sensitive material or in a processing solution).

(3) A silver halide photographic light-sensitive material, comprising a compound represented by the following formula (I) or (II) that is contained in at least one hydrophilic colloid layer placed on a base. The material preferably contains a coupler.

(4) An image-forming method, comprising carrying out development by heating the photographic material as stated in the above (1) at 65° to 180° C.

(5) An image-forming method, comprising carrying out development of the photographic material as stated in the above (1) in a solution.

(6) An image-forming method, comprising processing a photographic material, after exposure of the photographic material to light, with a processing solution containing a color-developing agent represented by the following formula (I) or (II):

Formula (I):

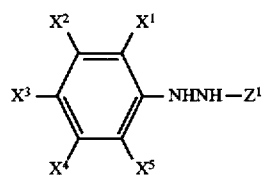

Formula (II):

wherein $Z^1$ represents an acyl group, a carbamoyl group, an alkoxycarbonyl, group, or an aryloxycarbonyl group; $Z^2$ represents a carbamoyl group, an alkoxycarbonyl group, or an aryloxycarbonyl group; $X^1$, $X^2$, $X^3$, $X^4$, and $X^5$, which are the same or different, each represent a hydrogen atom or a substituent, provided that the sum of the Hammett substituent constant σp values of $X^1$, $X^3$, and $X^5$ and the Hammett substituent constant σm values of $X^2$ and $X^4$ is 0.80 or more but 3.80 or below; and $R^3$ represents a heterocyclic group.

The compound represented by formula (I) or (II), which is a color-developing agent, is preferably represented by formula (III) or (IV), respectively:

Formula (III):

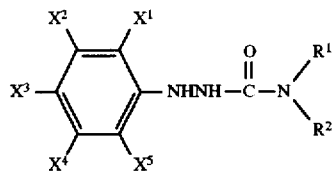

Formula (IV):

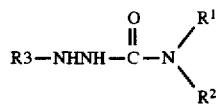

wherein $R^1$ and $R^2$ each represent a hydrogen atom or a substituent; $X^1$, $X^2$, $X^3$, $X^4$, and $X^5$, which are the same or different, each represent a hydrogen atom or a substituent, provided that the sum of the Hammett substituent constant σp values of $X^1$, $X^3$, and $X^5$ and the Hammett substituent constant σm values of $X^2$ and $X^4$ is 0.80 or more but 3.80 or below; and $R^3$ represents a heterocyclic group.

The color-developing agent represented by formula (III) is more preferably represented by formula (V), and the color-developing agent represented by formula (IV) is more preferably represented by formula (VI) or (VII):

Formula (V):

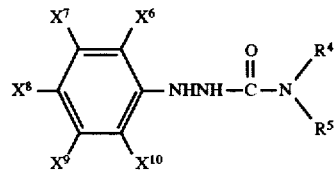

Formula (VI):

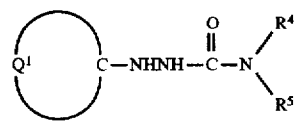

Formula (VII):

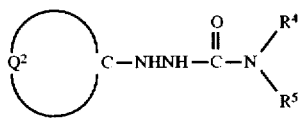

wherein $R^4$ and $R^5$ each represent a hydrogen atom or a substituent; and $X^6$, $X^7$, $X^8$, $X^9$, and $X^{10}$, which are the same or different, each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.20 or more but 3.80 or below, and more preferably 1.50 or more but 3.8 or below.

$Q^1$ represents a group of nonmetal atoms required to form a nitrogen-containing 5-membered to 8-membered heterocyclic ring together with the C.

$Q^2$ represents a group of nonmetal atoms required to form, together with the C, a nitrogen-containing 5-membered to 8-membered heterocyclic ring, to which a benzene ring or a heterocyclic ring is condensed.

A preferable mode is shown below:

(1) A mode that, when the light-sensitive material according to the present invention is processed with a processing solution, the color-developing agent of the present invention is not contained in the processing solution.

The compounds represented by formulae (I) to (VII) used in the present invention are described below in detail.

In formulae (I) and (II), $Z^1$ represents an acyl group, a carbamoyl group, an alkoxycarbonyl group, or an aryloxycarbonyl group, and $Z^2$ represents a carbamoyl group, an alkoxycarbonyl group, or an aryloxycarbonyl group. The acyl group preferably has 1 to 50 carbon atoms, and more preferably 2 to 40 carbon atoms. Specific examples include an acetyl group, a 2-methylpropanoyl group, a cyclohexylcarbonyl group, an n-octanoyl group, a 2-hexyldecanoyl group, a dodecanoyl group, a chloroacetyl group, a trifluoroacetyl group, a benzoyl group, a 4-dodecyloxybenzoyl group, a 2-hydroxymethylbenzoyl group, and a 3-(N-hydroxy-N-methylaminocarbonyl)propanoyl group.

With respect to the case wherein $Z^1$ and $Z^2$ each represent a carbamoyl group, a description is made in detail in formulas (III) to (VI).

Preferably the alkoxycarbonyl group and the aryloxycarbonyl group have 2 to 50 carbon atoms, and more preferably 2 to 40 carbon atoms. Specific examples include a methoxycarbonyl group, an ethoxycarbonyl group, an isobutyloxycarbonyl group, a cyclohexyloxycarbonyl group, a dodecyloxycarbonyl group, a benzyloxycarbonyl group, a phenoxycarbonyl group, a 4-octyloxyphenoxycarbonyl group, a 2-hydroxymethylphenoxycarbonyl group, and a 2-dodecyloxyphenoxycarbonyl group.

$X^1$, $X^2$, $X^3$, $X^4$, and $X^5$ each represent a hydrogen atom or a substituent. Examples of the substituent include a straight-chain alkyl group, a branched-chain alkyl group, or a cycloalkyl group, having 1 to 50 carbon atoms (e.g. trifluoromethyl, methyl, ethyl, propyl, heptafluoropropyl, isopropyl, butyl, t-butyl, t-pentyl, cyclopentyl, cyclohexyl, octyl, 2-ethylhexyl, and dodecyl); a straight-chain alkenyl group, a branched-chain alkenyl group, or a cycloalkenyl group, having 2 to 50 carbon atoms (e.g. vinyl, 1-methylvinyl, and cyclohexen-1-yl); an alkynyl group having 2 to 50 carbon atoms in all (e.g. ethynyl and 1-propinyl), an aryl group having 6 to 50 carbon atoms (e.g. phenyl, naphthyl, and anthryl), an acyloxy group having 1 to 50 carbon atoms (e.g. acetoxy, tetradecanoyloxy, and benzoyloxy), a carbamoyloxy group having 1 to 50 carbon atoms (e.g. N,N-dimethylcarbamoyloxy), a carbonamido group having 1 to 50 carbon atoms (e.g. formamido, N-methylacetamido, acetamido, N-methylformamido, and benzamido), a sulfonamido group having 1 to 50 carbon atoms (e.g. methanesulfonamido, dodecansulfonamido, benzenesulfonamido, and p-toluenesulfonamido), a carbamoyl group having 1 to 50 carbon atoms (e.g. N-methylcarbamoyl, N,N-diethylcarbamoyl, and N-mesylcarbamoyl), a sulfamoyl group having 0 to 50 carbon atoms (e.g. N-butylsulfamoyl, N,N-diethylsulfamoyl, and N-methyl-N-(4-methoxyphenyl) sulfamoyl), an alkoxy group having 1 to 50 carbon atoms (e.g. methoxy, propoxy, isopropoxy, octyloxy, t-octyloxy, dodecyloxy, and 2-(2,4-di-t-pentylphenoxy)ethoxy), an aryloxy group having 6 to 50 carbon atoms (e.g. phenoxy, 4-methoxyphenoxy, and naphthoxy), an aryloxycarbonyl group having 7 to 50 carbon atoms (e.g. phenoxycarbonyl and naphthoxycarbonyl), an alkoxycarbonyl group having 2 to 50 carbon atoms (e.g. methoxycarbonyl and t-butoxycarbonyl), an N-acylsulfamoyl group having 1 to 50 carbon atoms (e.g. N-tetradecanoylsulfamoyl and N-benzoylsulfamoyl), an alkylsulfonyl group having 1 to 50 carbon atoms (e.g. methanesulfonyl, octylsulfonyl, 2-methoxyethylsulfonyl, and 2-hexyldecylsulfonyl), an arylsulfonyl group having 6 to 50 carbon atoms (e.g. benzenesulfonyl, p-toluenesulfonyl, and 4-phenylsulfonylphenylsulfonyl), an alkoxycarbonylamino group having 2 to 50 carbon atoms (e.g. ethoxycarbonylamino), an aryloxycarbonylamino group having 7 to 50 carbon atoms (e.g. phenoxycarbonylamino and naphthoxycarbonylamino), an amino group having 0 to 50 carbon atoms (e.g. amino, methylamino, diethylamino, diisopropylamino, anilino, and morpholino), a cyano group, a nitro group, a carboxyl group, a hydroxy group, a sulfo group, a mercapto group, an alkylsulfinyl group having 1 to 50 carbon atoms (e.g. methanesulfinyl and octanesulfinyl), an arylsulfinyl having 6 to 50 carbon atoms (e.g. benzenesulfinyl, 4-chlorophenylsulfinyl, and p-toluenesulfinyl), an alkylthio group having 1 to 50 carbon atoms (e.g. methylthio, octylthio, and cyclohexylthio), an arylthio group having 6 to 50 carbon atoms (e.g. phenylthio and naphthylthio), a ureido group having 1 to 50 carbon atoms (e.g. 3-methylureido, 3,3-dimethylureido, and 1,3-diphenylureido), a heterocyclic group having 2 to 50 carbon atoms (e.g. a 3-membered to 12-membered monocyclic ring or condensed ring having at least one (preferably 1 to 9) hetero atom(s), such as nitrogen, oxygen, and sulfur, for example, 2-furyl, 2-pyranyl, 2-pyridyl, 2-thienyl, 2-imidazolyl, morpholino, 2-quinolyl, 2-benzimidazolyl, 2-benzothiazolyl, and 2-benzoxazolyl), an acyl group having 1 to 50 carbon atoms (e.g. acetyl, benzoyl, and trifluoroacetyl), a sulfamoylamino group having 0 to 50 carbon atoms (e.g. N-butylsulfamoylamino and N-phenylsulfamoylamino), a silyl group having 3 to 50 carbon atoms (e.g. trimethylsilyl, dimethyl-t-butylsilyl, and triphenylsilyl), and a halogen atom (e.g. a fluorine atom, a chlorine atom, and a bromine atom). The above substituents may have a substituent, and examples of such a substituent include those mentioned above. Further, $X^1$, $X^2$, $X^3$, $X^4$, and $X^5$ may bond together to form a condensed ring.

Preferable examples of $X^1$, $X^2$, $X^3$, $X^4$, and $X^5$ are a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, and a heterocyclic group; and preferably, out of $X^1$, $X^2$, $X^3$, $X^4$, and $X^5$, 2 to 5 of them, and more preferably 3 to 5 of them, represent these groups.

Herein, preferable examples of the heterocyclic ring include 5- to 8-membered heterocyclic groups containing nitrogen, such as pyridine, pyrimidine, pyridazine, pyradine, 1,2,4-triazine, 1,3,5-triazine, pyrazole, imidazole, thiazole, isothiazole, oxazole, isooxazole, and 1,2,4-thiadiazole.

The number of carbon atoms of the substituent is preferably 50 or below, more preferably 42 or below, and most preferably 34 or below, and there is preferably 1 or more carbon atom(s).

With respect to $X^1$, $X^2$, $X^3$, $X^4$, and $X^5$ in formulae (I) and (III), the sum of the Hammett substituent constant σp values of $X^1$, $X^3$, and $X^5$ and the Hammett substituent constant σm values of $X^2$ and $X^4$ is 0.80 or more but 3.80 or below. $X^6$, $X^7$, $X^8$, $X^9$, and $X^{10}$ in formula (V) each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, which may have a substituent and may bond together to form a condensed ring. Specific examples of $X^6$ through $X^{10}$ are the same as those described for $X^1$, $X^2$, $X^3$, $X^4$, and $X^5$. In formula (V), the sum of the Hammett substituent constant σp values of $X^6$, $X^8$, an $X^{10}$ and the Hammett substituent constant σm values of $X^7$ and $X^9$ is 1.20 or more but 3.80 or below, more preferably 1.50 or more but 3.80 or below, and most preferably 1.70 or more but 3.80 or below.

Herein, if the sum of the σp values and the σm values is less than 0.80, the problem arises that the color formation is unsatisfactory, while if the sum of the σp values and the σm values is over 3.80, the synthesis and availability of the compounds themselves become difficult.

Parenthetically, Hammett substituent constants σp and σm are described in detail in such books as "Hammett no Hosoku/Kozo to Hannousei," written by Naoki Inamoto (Maruzen); "Shin-jikken Kagaku-koza 14/Yukikagoubutsu no Gosei to Hanno V," page 2605 (edited by Nihonkagakukai, Maruzen); "Riron Yukikagaku Kaisetsu," written by Tadao Nakaya, page 217 (Tokyo Kagakudojin); and "Chemical Review" (Vol. 91), pages 165 to 195 (1991).

$R^1$ and $R^2$ in formulae (III) and (IV) and $R^4$ and $R^5$ in formulae (V), (VI), and (VII), each represent a hydrogen atom or a substituent, and examples of the substituent are the same as those described for $X^1$, $X^2$, $X^3$, $X^4$, and $X^5$; preferably each represents a hydrogen atom, a substituted or unsubstituted alkyl group having 1 to 50 carbon atoms, a substituted or unsubstituted aryl group having 6 to 50 carbon atoms, or a substituted or unsubstituted heterocyclic group having 1 to 50 carbon atoms, and more preferably at least one of $R^1$ and $R^2$, and at least one of $R^4$ and $R^5$, are each a hydrogen atom. Substituents that may be possessed by the above groups include groups represented by $X^1$, $X^2$, $X^3$, $X^4$, and $X^5$.

In formulae (II) and (IV), $R^3$ represents a heterocyclic group. Herein, a preferable heterocyclic group has 1 to 50 carbon atoms, and the heterocyclic group contains at least one hetero atom, preferably 1 to 9 hetero atoms, such as a nitrogen atom, an oxygen atom, and a sulfur atom, and further the heterocyclic group is a saturated or unsaturated 3-membered or 12-membered (preferably 3-membered to 8-membered) monocyclic or condensed ring. Specific examples of the heterocyclic ring are furan, pyran, pyridine, thiophene, imidazole, quinoline, benzimidazole, benzothiazole, benzoxazole, pyrimidine, pyrazine, 1,2,4-thiadiazole, pyrrole, oxazole, thiazole, quinazoline, isothiazole, pyridazine, indole, pyrazole, triazole, and quinoxaline. Preferable examples of the heterocyclic ring include 5- to 8-membered heterocyclic groups containing nitrogen (preferably 1 to 4 nitrogen atoms), such as pyridine, pyrimidine, pyridazine, pyradine, 1,2,4-triazine, 1,3,5-triazine, pyrazole, imidazole, thiazole, isothiazole, oxazole, isooxazole, and 1,2,4-thiadiazole. More preferable heterocyclic rings include 5- to 8-membered heterocyclic rings containing nitrogen (preferably 1 to 4 nitrogen atoms), to which a benzene ring or a heterocyclic ring is fused, such as quinazoline, quinoxaline, phthalazine, quinoline, isoquinoline, benzothiazole, benzoxazole, benzimidazole, pteridine, and purine. These heterocyclic groups may have a substituent, and preferably they have one or more, preferably one or more but 9 or less electron-attracting groups. Herein, the term "an electron-attracting group" means one wherein the Hammett σp value is a positive value.

In formulas (II) and (IV), when $R^3$ is a 4-pyrimidinyl group and has as a substituent a halogen-substituted alkyl group, preferably $R^1$ or $R^2$ is not an aryl group.

In formula (VI), $Q_1$ represents a group of nonmetal atoms required to form, together with the C, a 5- to 8-membered nitrogen-containing heterocyclic ring. This heterocyclic ring has the same meaning as that of $R^3$ of formula (II). Preferable examples of the heterocyclic ring are the same as the preferable examples of $R^3$.

When the heterocyclic group formed by $Q_1$, together with the C, is a 4-pyrimidinyl group and has as a substituent a halogen-substituted alkyl group, preferably $R^4$ or $R^5$ is not an aryl group.

In formula (VII), $Q_2$ represents a group of nonmetal atoms required to form, together with the C, a 5- to 8-membered nitrogen-containing ring, to which a benzene ring or heterocyclic ring is fused. This condensed heterocyclic ring has the same meaning as that of $R^3$ of formula (II). Preferable examples thereof are the same as the more preferable examples of $R^3$.

When the developing agent of the present invention is built in a light-sensitive material, preferably at least one, and more preferably 1 to 7 of $Z^1$, $Z^2$, $R^1$ to $R^5$, and $X^1$ to $X^{10}$, has one, preferably 1 to 7 ballasting groups. When the developing agent of the present invention is contained in a processing solution, preferably at least one, and more preferably one (1) to 7 ballasting groups. Herein, a "ballasting group" means a group, having 5 to 50, preferably 8 to 40 carbon atoms, which makes the developing agent that has a ballasting group, easily-soluble in a high-boiling organic solvent, and been hardly deposited even after emulsifying and dispersing, and which makes the developing agent immobilized in a hydrophilic colloid. When the developing agent of the present invention is contained in a processing solution, preferably at least one, and more preferably one (1) to seven (7) groups of $Z^1$, $Z^2$, $R^1$ to $R^5$, and $X^1$ to $X^{10}$, have a hydrophilic group.

Herein, a "hydrophilic group" means a polar group that makes the developing agent, which has a hydrophilic group, easily solubilized in a processing solution. As the hydrophilic group, a known hydrophilic group can be used such as, specifically, a substituent having at least one —OH or —NH—, and more specifically a hydroxyl group, a hydroxyalkyl group, a hydroxyphenyl group, a carboxyl group, an amino group, a carbamoyl group, and a sulfamoyl group.

Now, novel color-developing agents used in the present invention are described specifically, but the scope of the present invention is not limited to them.

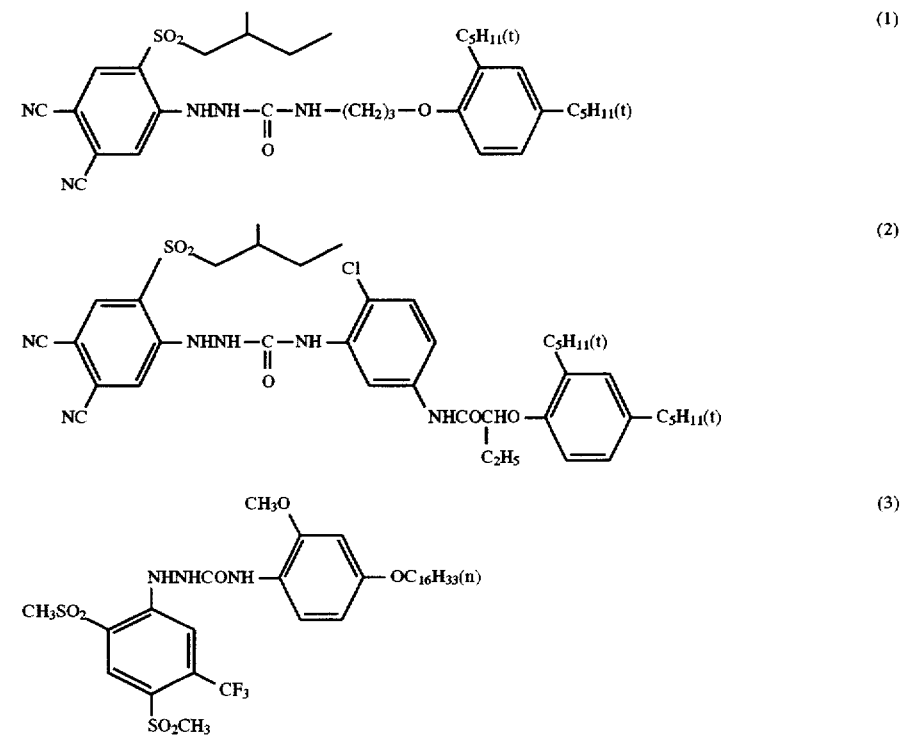

-continued
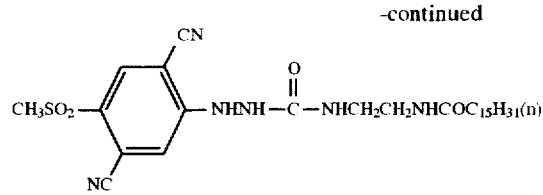
(4)
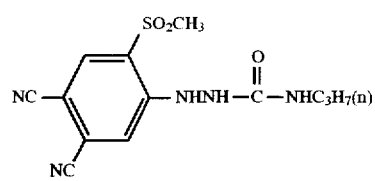
(5)
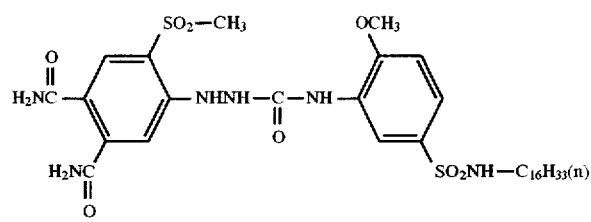
(6)
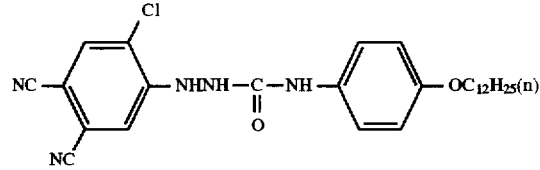
(7)
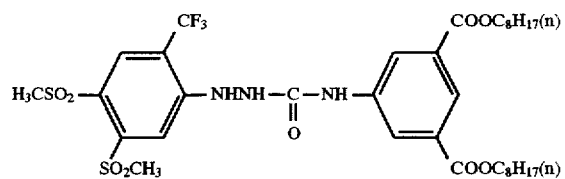
(8)
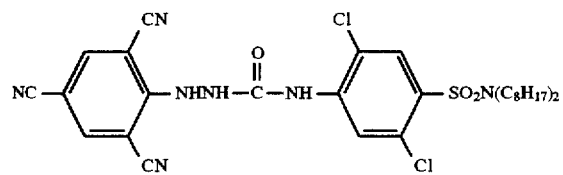
(9)
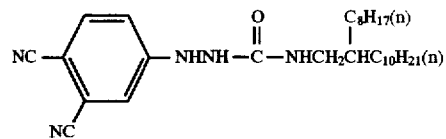
(10)
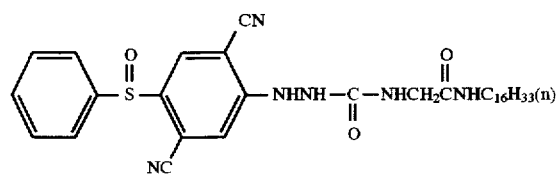
(11)
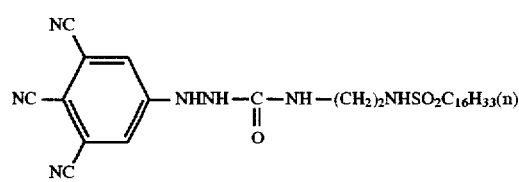
(12)

-continued
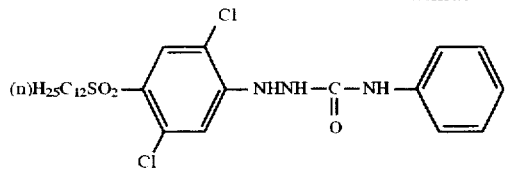
(13)
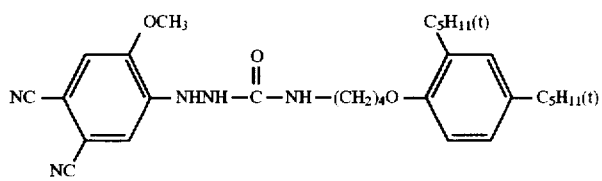
(14)
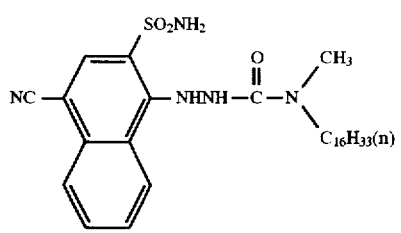
(15)
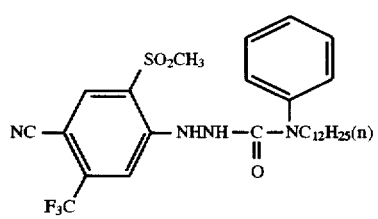
(16)
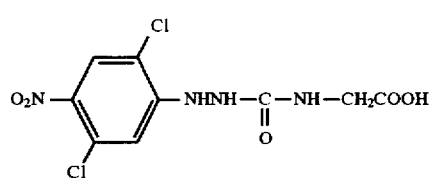
(17)
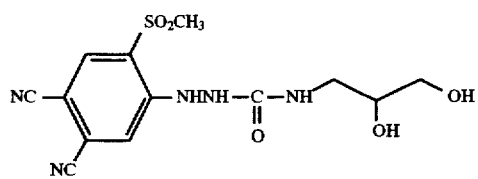
(18)
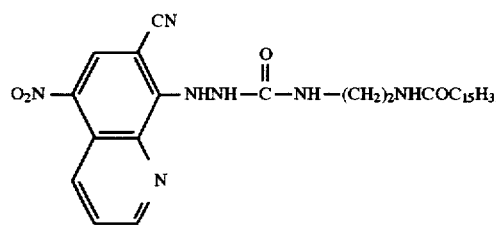
(19)
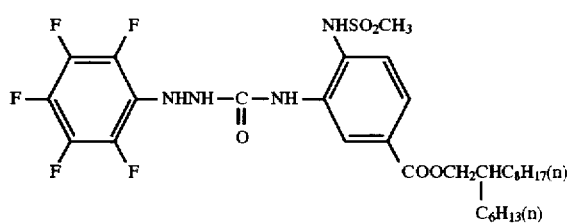
(20)

-continued
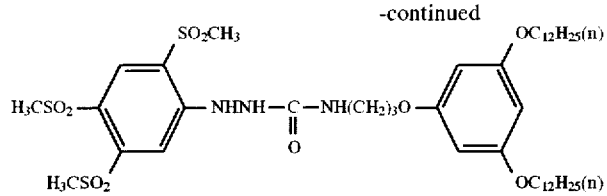 (21)
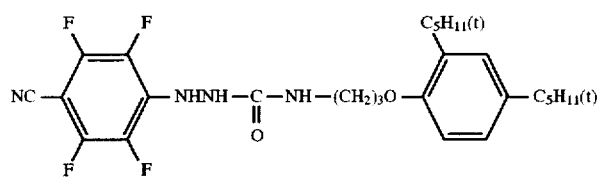 (22)
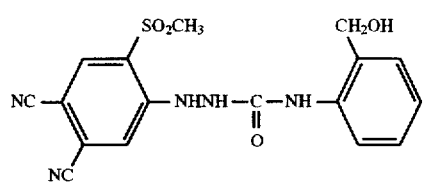 (23)
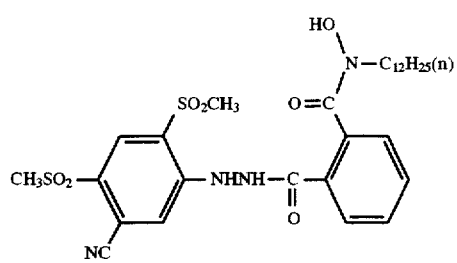 (24)
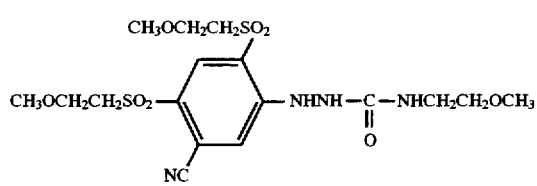 (25)
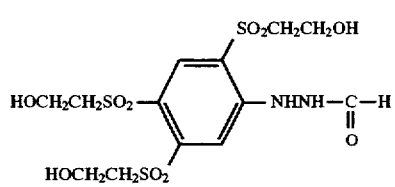 (26)
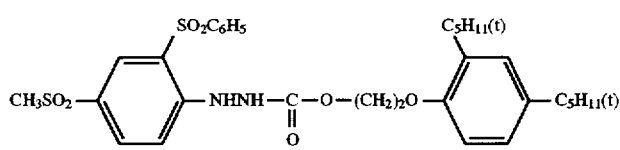 (27)
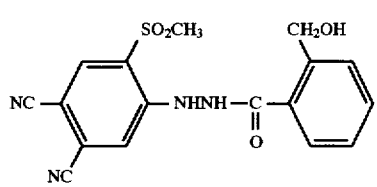 (28)
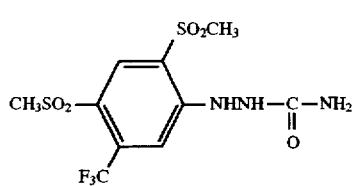 (29)

-continued
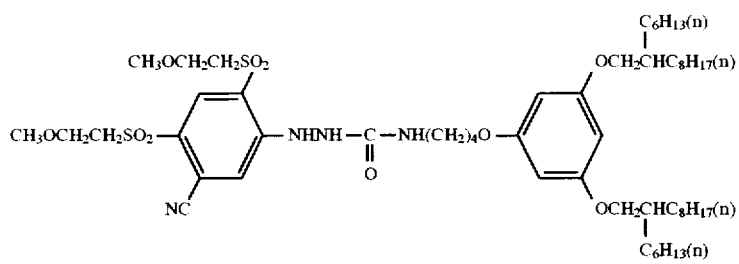
(30)
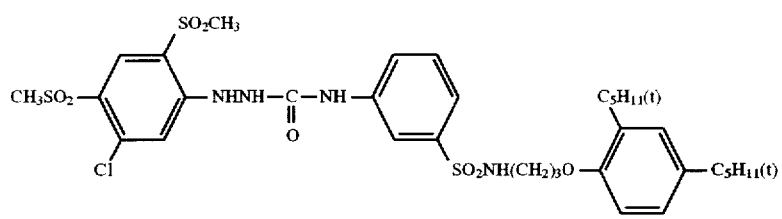
(31)
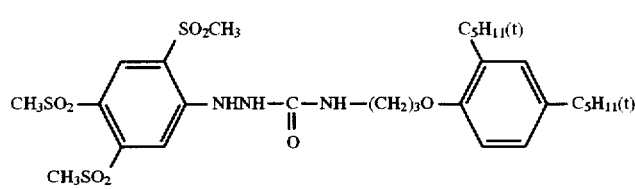
(32)
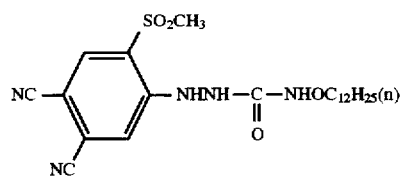
(33)
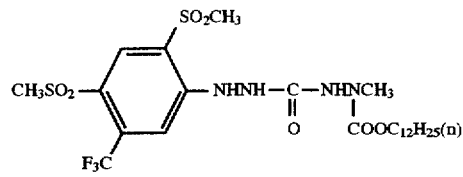
(34)
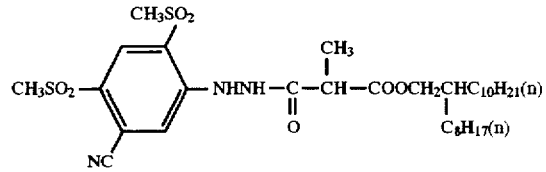
(35)
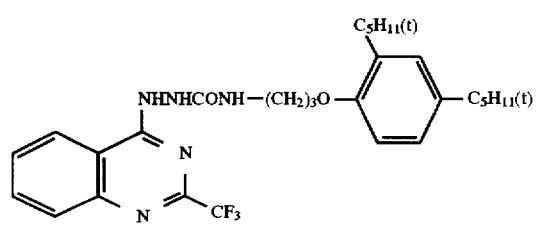
(36)
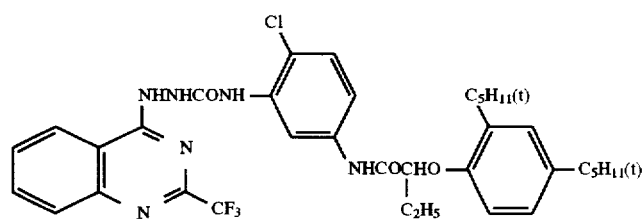
(37)

-continued
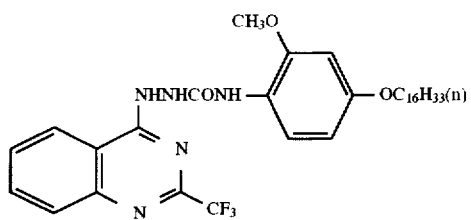
(38)
(39)
(40)
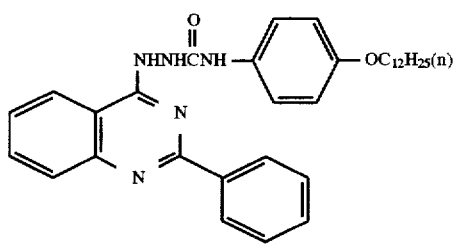
(41)
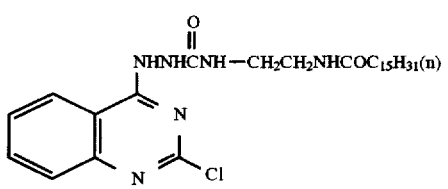
(42)
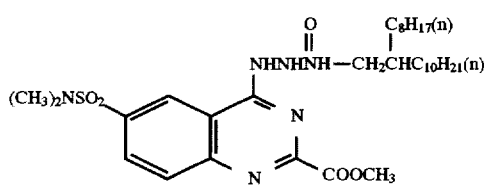
(43)
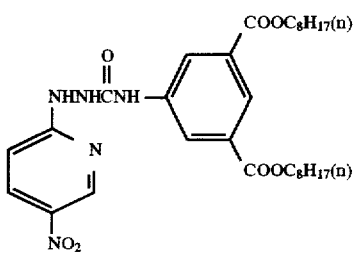
(44)
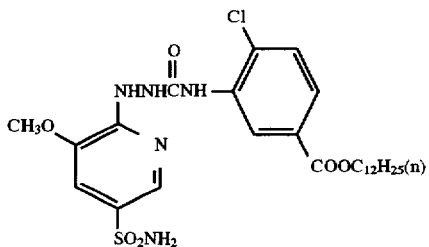
(45)

-continued
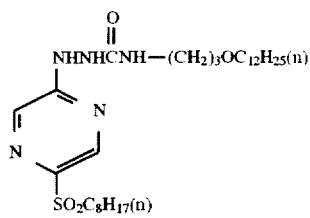 (46)
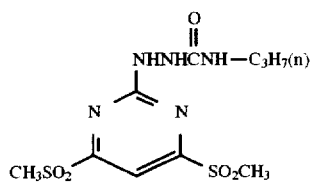 (47)
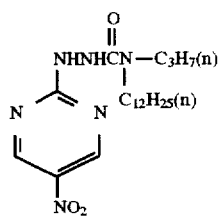 (48)
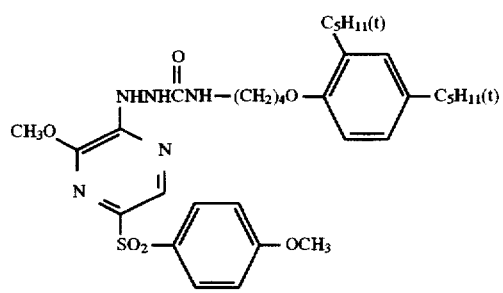 (49)
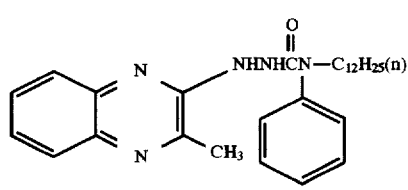 (50)
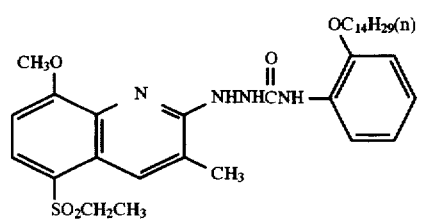 (51)
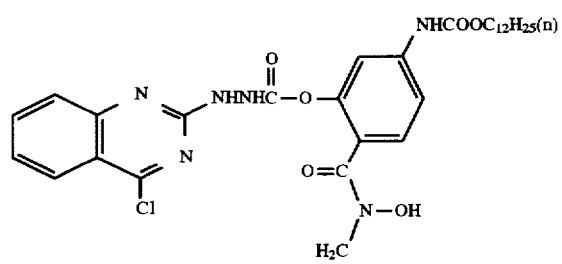 (52)

-continued
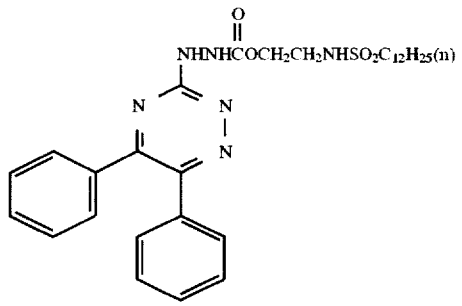
(53)
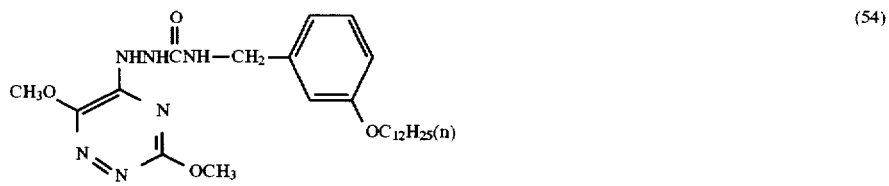
(54)
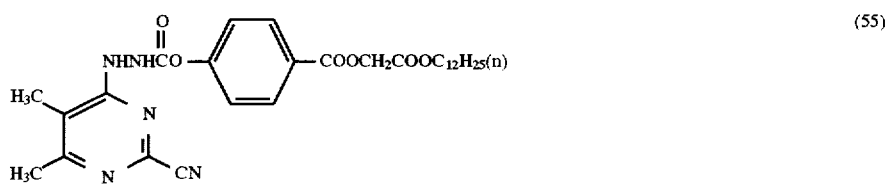
(55)
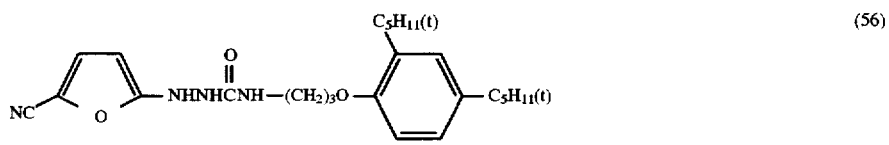
(56)
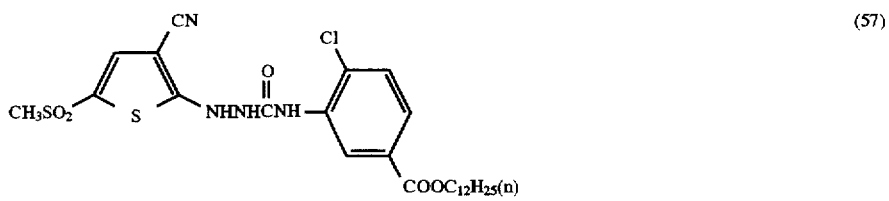
(57)
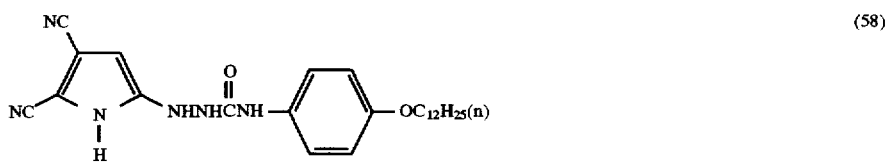
(58)
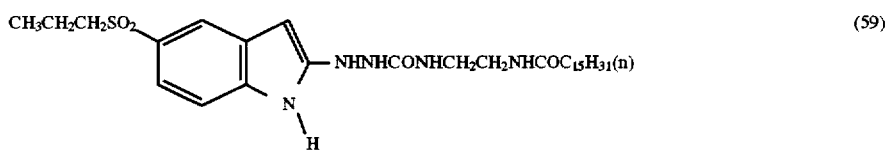
(59)
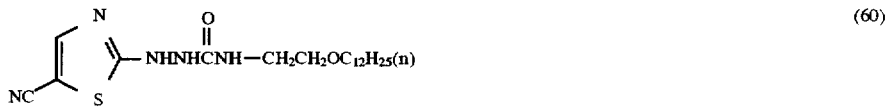
(60)
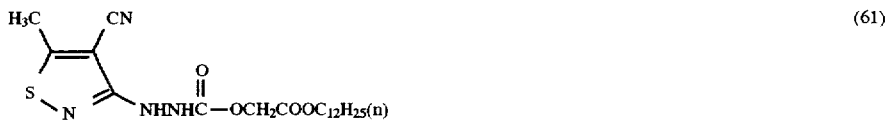
(61)

-continued
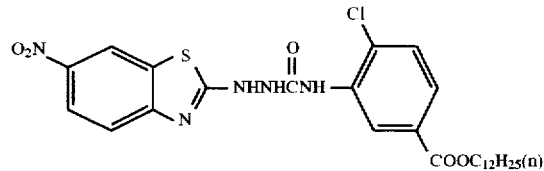
(62)
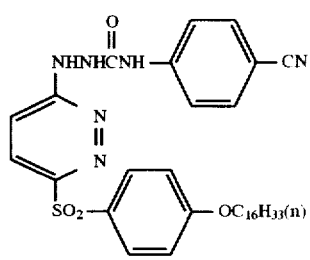
(63)
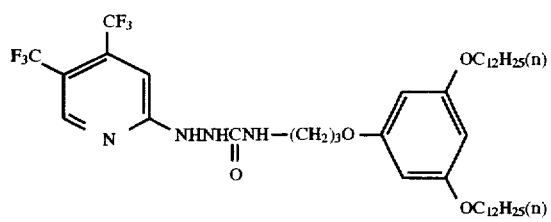
(64)
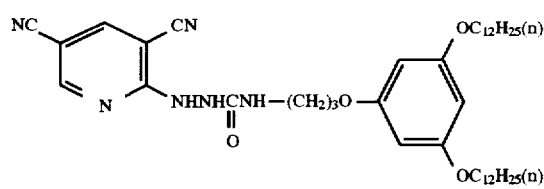
(65)
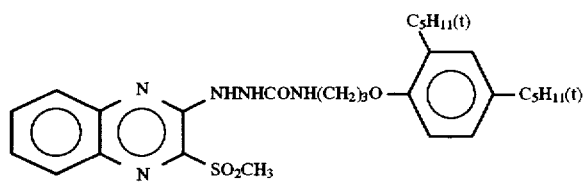
(66)
(67)
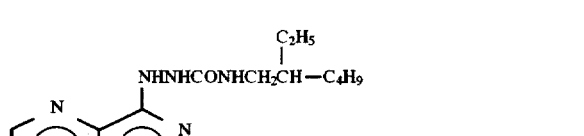
(68)
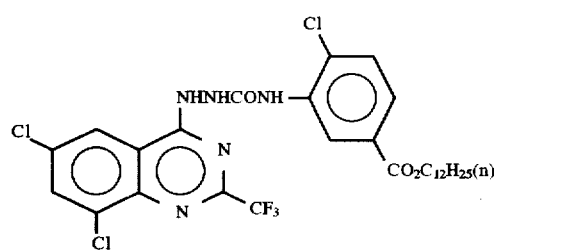
(69)

-continued
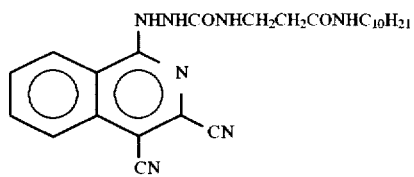
(70)
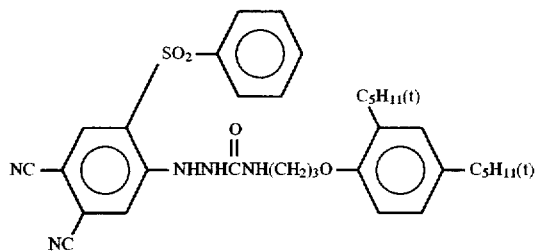
(71)
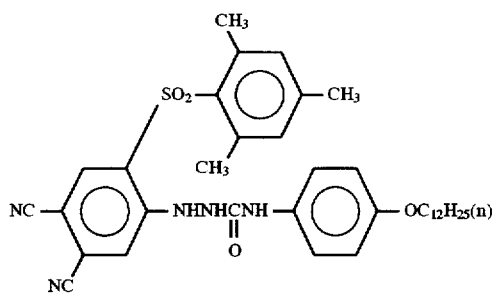
(72)
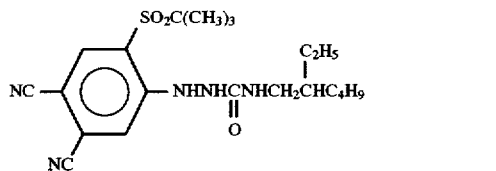
(73)
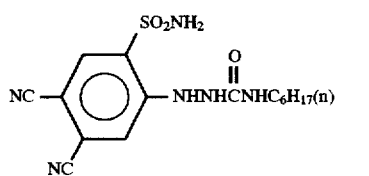
(74)
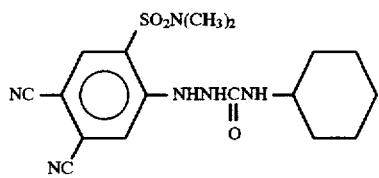
(75)
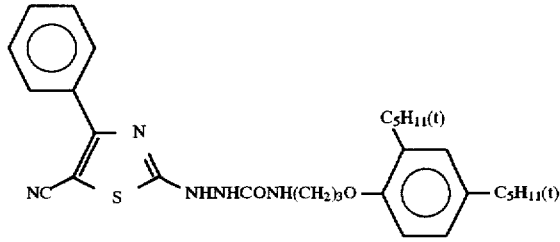
(76)

27

-continued

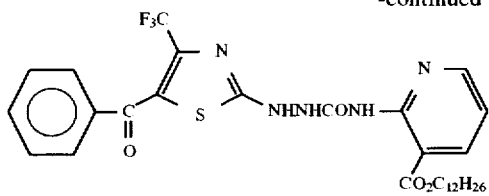
(77)

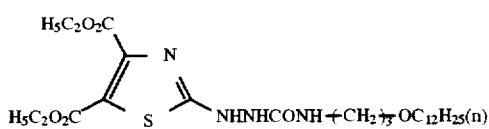
(78)

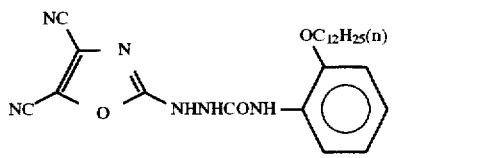
(79)

(80)

Now, general methods of synthesizing compounds of the present invention are described. These compounds can be synthesized, for example, by reacting compound represented by formula (VIII-1), (VIII-2), (VIII-3), (VIII-4), or (VIII-5) with compound represented by formula (IX-1) or (IX-2) or compound represented by formula (X-1), (X-2), or (X-3), wherein $R^1$, $R^2$, $R^3$, $R^4$, $R^5$, $X^1$ to $X^{10}$, $Q^1$, and $Q^2$ have the same meanings as those defined in formulae (I) to (VII), and Z represents $Z^1$ or $Z^2$.

Formula (VIII-1):

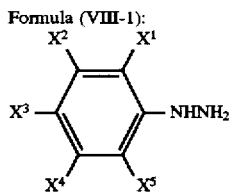

Formula (VIII-2):
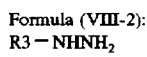

Formula (VIII-3):

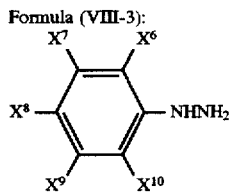

Formula (VIII-4):
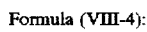
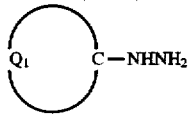

Formula (VIII-5):
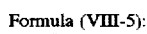
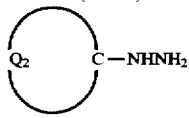

28

-continued

Formula (IX-1):
$O=C=N-R^1$

Formula (IX-2):
$O=C=N-R^4$

Formula (X-1):
$L-Z$

Formula (X-2):

$$L-\overset{O}{\underset{\|}{C}}-N\overset{R^1}{\underset{R^2}{\diagdown}}$$

Formula (X-3):

$$L-\overset{O}{\underset{\|}{C}}-N\overset{R^4}{\underset{R^5}{\diagdown}}$$

wherein L represents a group that is capable of coupling split-off by nucleophilic attack with a nucleophilic agent, such as an aryloxy group and a chlorine atom.

Typical synthetic examples of some compounds out of the compounds used in the present invention are shown below. Other compounds can also be synthesized in the same way as that for the following examples.

SYNTHETIC EXAMPLE 1

Synthesis of Exemplified Compound (5)

The synthesis is carried out by following the below-shown synthesis route:

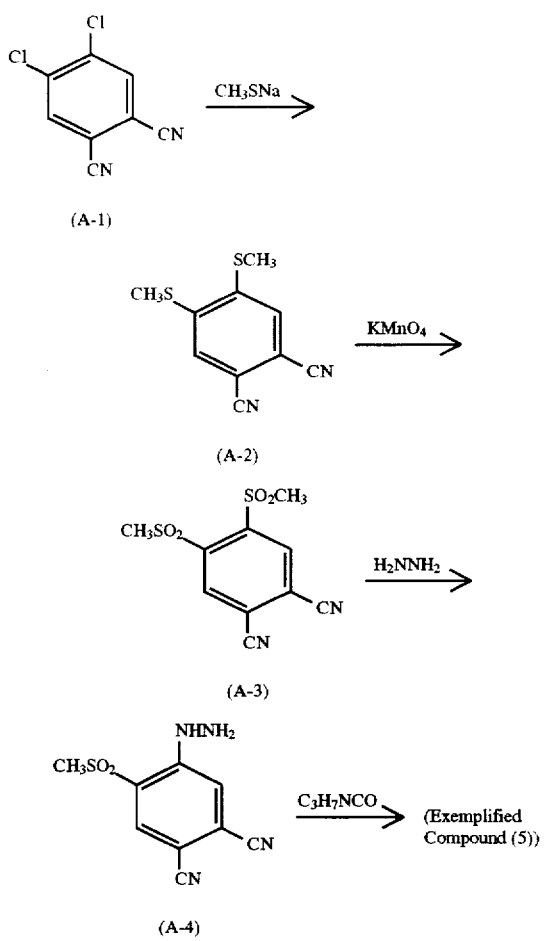

Synthesis of Compound (A-2)

53.1 g of 1,2-dichloro-4,5-dicyanobenzene (A-1) (CAS Registry No. 139152-08-2) was dissolved in 1.1 liters of N,N-dimethylformamide (DMF), and then 268 g of an aqueous methyl mercaptan sodium salt solution (15%) was added, dropwise, to the solution, at room temperature over 1 hour, followed by stirring at 60° C. for 1 hour. The reaction liquid was cooled to room temperature and water was poured thereinto, followed by stirring for 30 min. The produced white solid was filtered, washed with water, and dried. Yield: 46.5 g (78.1%).

Synthesis of Compound (A-3)

41.1 g of Compound (A-2) was suspended in 400 ml of acetic acid, and then a solution of 89.3 g of potassium permanganate in 400 ml of water was added, dropwise, over 1 hour under cooling with water. After the reaction mixture was allowed to stand overnight at room temperature, 2 liters of water and 2 liters of ethyl acetate were added thereto, and the mixture was Celite-filtered. The filtrate was separated, and the organic layer was washed with water, an aqueous sodium hydrosulfite solution, an aqueous sodium bicarbonate solution, and then brine, followed by drying over anhydrous magnesium sulfate. After filtering the dried organic layer, the solvent was distilled off, and an ethyl acetate/ hexane mixed solvent was added to the residue, to effect crystallization, to obtain 29.4 g of a white solid of Compound (A-3). Yield: 55.0%.

Synthesis of Compound (A-4)

29.4 g of Compound (A-3) was dissolved in 200 ml of dimethylsulfoxide (DMSO), and 8.7 g of hydrazine monohydrate was added, dropewise, to the solution, over 15 min under cooling with water, followed by stirring for 10 min under cooling with water. The reaction liquid was poured into water, and the produced yellow solid was filtered, washed with water, and dried. Yield: 17.4 g (70.9%).

Synthesis of Exemplified Compound (5)

11.8 g of Compound (A-4) was dissolved in 50 ml of tetrahydrofuran, and 4.7 g of propyl isocyanate was added, dropwise, to the solution, at room temperature over 30 min, followed by stirring for 1 hour. The reaction mixture was poured into water, and extraction was effected with ethyl acetate. The organic layer was washed with hydrochloric acid and then brine; then it was dried over anhydrous magnesium sulfate, filtered, and the solvent was distilled off. The residue was crystallized from an ethyl acetate/hexane mixed solvent (1:10), to obtain 14.5 g of a white solid of Exemplified Compound (5). Yield: 90.2%.

SYNTHETIC EXAMPLE 2

Synthesis of Exemplified Compound (2)

The synthesis was made by following the below-shown synthesis route:

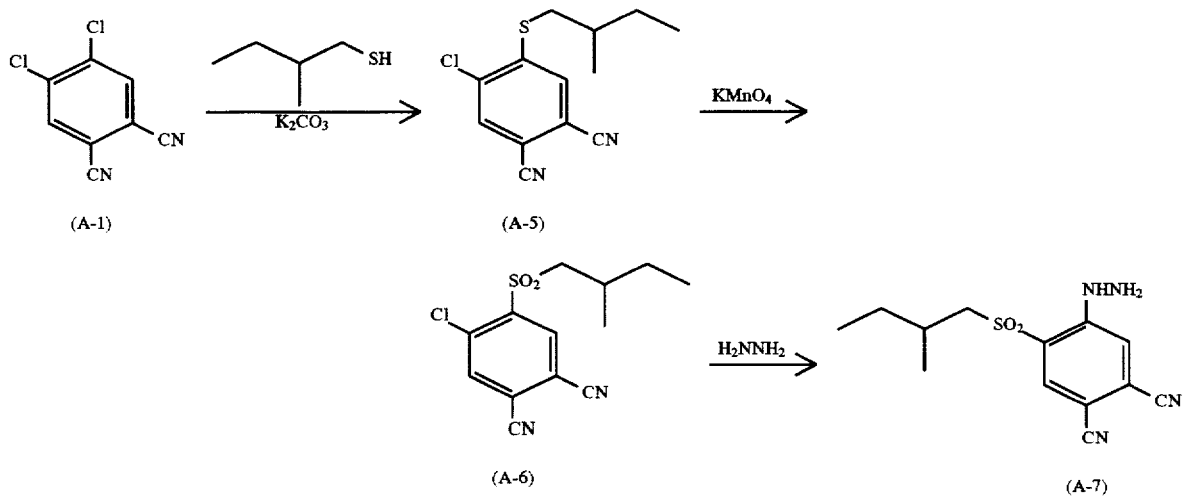

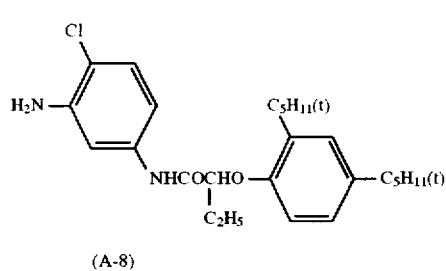

(A-8)

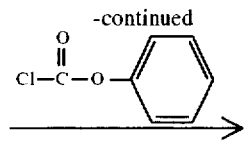

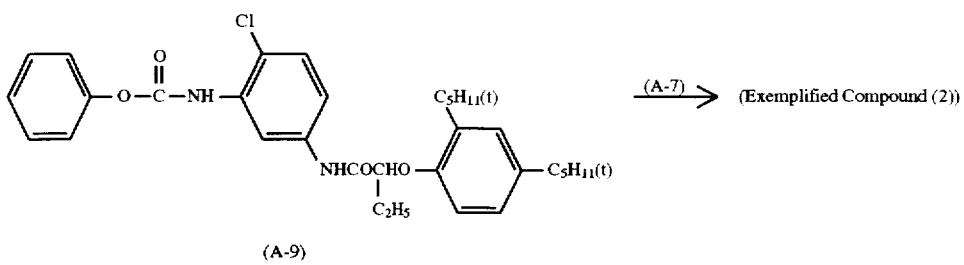

(A-9)     (A-7) → (Exemplified Compound (2))

Synthesis of Compound (A-5)

84.7 g of Compound (A-1) and 89.8 g of potassium carbonate were suspended in 600 ml of DMF, and then 60.3 ml of 2-methylbutylmercaptan was added, dropwise, to the suspension, at room temperature over 1 hour, followed by stirring at room temperature for 1 hour. The reaction mixture was poured into water and stirred for 10 min. The produced white solid was filtered, washed with water, and dried. Yield: 100.8 g (88.5%).

Synthesis of Compound (A-6)

98.0 g of Compound (A-5) was suspended in 500 ml of acetic acid and 500 ml of water, and to the suspension was added, dropwise, a solution of 88.5 g of potassium permanganate in 500 ml of water, at room temperature over 1 hour, followed by stirring at room temperature for 2 hours. Then 2 liters of water and 2 liters of ethyl acetate were added to the reaction mixture, followed by Celite-filtering. The filtrate was separated, and the organic layer was washed with water, an aqueous hydrosulfite solution, an aqueous sodium bicarbonate solution, and brine, followed by drying over anhydrous magnesium sulfate. After filtering the dried organic layer, the solvent was distilled off, and isopropyl alcohol was added to the residue, to effect crystallization, to obtain 53.2 g of a white solid of Compound (A-6). Yield: 48.4%.

Synthesis of Compound (A-7)

50.5 g of Compound (A-6) was dissolved in 100 ml of DMSO, and then 17.0 g of hydrazine monohydrate was added, dropwise, thereto, over 10 min under cooling with ice, followed by stirring at room temperature for 30 min. The reaction mixture was poured into water, and extraction was carried out with ethyl acetate. The organic layer was washed with water and dried over anhydrous magnesium sulfate. After filtering the dried organic layer, the solvent was distilled off, and the residue was purified by silica gel chromatography, using methylene chloride as an eluent. Crystallization was carried out from ethyl acetate/hexane (1:2), to obtain 31.4 g of a yellow solid of Compound (A-7). Yield: 63.2%.

Synthesis of Compound (A-9)

44.5 g of Compound (A-8) (CAS Registry No. 51461-11-1) was dissolved in 500 ml ethyl acetate, and then a solution of 25 g of sodium bicarbonate in 500 ml of water was added to the solution. To the resulting solution was added, dropwise, 16.4 g of phenyl chlorocarbonate, at room temperature over 30 min, followed by stirring for a further 1 hour. The layers were separated, the organic Layer was washed with brine and dried over anhydrous magnesium sulfate, and after filtering the dried organic layer, the solvent was distilled off, to obtain 54.0 g of a pale yellow oil of Compound (A-9). Yield: 95.6%.

Synthesis of Exemplified Compound (2)

5.8 g of Compound (A-7), 11.3 g of Compound (A-9), and 0.60 g of DMAP (N,N-dimethylaminopyridine) were dissolved in 100 ml of acetonitrile, and the solution was stirred at 60° C. for 3 hours. The reaction mixture was poured into water, and extraction with ethyl acetate was carried out. The organic layer was washed with an aqueous sodium bicarbonate solution, hydrochloric acid, and then brine; then it was dried over anhydrous magnesium sulfate, and after filtration of the dried organic layer was carried out, the solvent was distilled off. The residue was purified by silica gel column chromatography (eluent: ethyl acetate/hexane= 1/2), and crystallization from hexane was carried out, to obtain 8.0 g of a white solid of Exemplified Compound (2). Yield: 52.4%.

SYNTHETIC EXAMPLE 3

Synthesis of Exemplified Compound (1)

The synthesis was carried out by following the synthesis route shown below:

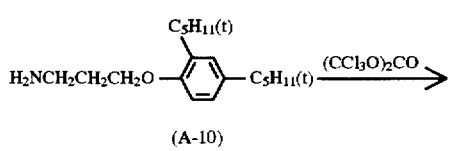

(A-10)

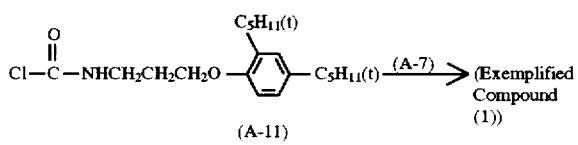

(A-11)

Synthesis of Exemplified Compound (1)

4.6 g of tripliosgene was dissolved in 100 ml of THF, and to the solution were added, dropwise, 13.6 g of Compound (A-10) (CAS Registry No. 61053-26-7), at room temperature over 10 min. and then 18.7 ml of triethylamine, at room temperature over 10 min. Reaction was carried out for 30 min. to obtain a solution of Compound (A-11). To this solution was added 13.0 g of Compound (A-7), in portions, at room temperature over 10 min. After the reaction mixture was stirred for a further 1 hour, the reaction mixture was poured into water, and extraction with ethyl acetate was carried out. After the organic layer was washed with an aqueous sodium bicarbonate solution, hydrochloric acid, and then brine, the organic layer was dried over anhydrous magnesium sulfate. After the dried organic layer was filtered, the solvent was distilled off. The residue was purified by silica gel column chromatography, and crystallization from ethyl acetate/hexane 1:10 mixture was carried out, to obtain a white solid of Exemplified Compound (1). Yield: 17.0 g (61.3%).

SYNTHETIC EXAMPLE 4
Synthesis of Exemplified Compound (37)

The synthesis was carried out by following the synthesis route given below:

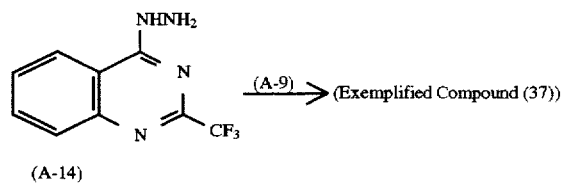

Similarly to Synthetic Example 2, the synthesis was carried out by using 6.0 g of Compound (A-14) (European Patent No. 545491A1), 14.98 g of Compound (A-9), and 0.5 g of DMAP, to obtain a white solid of Exemplified Compound (37). Yield: 12.0 g (65.3%).

SYNTHETIC EXAMPLE 5
Synthesis of Exemplified Compound (36)

Similarly to Synthetic Example 3, the synthesis was carried out by using Compound (A-11), prepared similarly to Synthetic Example 3 from 5.8 g of Compound (A-10) and 4.3 g of Compound (A-14), to obtain a white solid of Exemplified Compound (36). Yield: 6.7 g (61.5%).

SYNTHETIC EXAMPLE 6
Synthesis of Exemplified Compound (67)

The synthesis course was as follows:

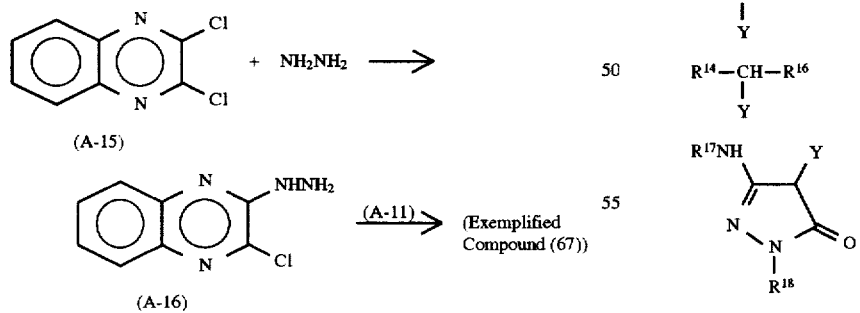

Synthesis of Compound (A-16)

20.0 g of Compound (A-15) (manufactured by Aldrich) was dissolved in 200 ml of DMSO, and the solution was added, dropwise over 10 min, to a solution of 20 g of hydrazine monohydrate in 200 ml of ethanol, under cooling with ice, followed by stirring at room temperature for 30 min. The reaction mixture was poured into water; extraction with ethyl acetate was carried out, and after the extract was washed with water, the extract was dried over anhydrous magnesium sulfate. After filtering, the solvement was distilled off under reduced pressure and the residue was crystallized from a mixed solvent of ethyl acetate and hexane to obtain 13.3 g of yellow crystals of Compound (A-16). Yield: 68.0%.

Synthesis of Exemplified Compound (67)

Synthetic Example 3 was repeated, except that Compound (A-11), which was prepared from 15.1 g of Compound (A-10) and 5.14 g of triphosgene similarly to Synthesis Example 3, 15.0 ml of trithylamine, and 7.8 g of Compound (A-16), thereby preparing 17.1 g of a yellow solid of Exemlified Compound (67). Yield: 83.7%

The color-developing agent of the present invention is used together with a compound that can form a dye by oxidation coupling reaction (a coupler). The coupler may be a four-equivalent coupler or a two-equivalent coupler, but in the present invention a two-equivalent coupler is preferred. Specific examples of the couplers, both four-equivalent couplers and two-equivalent couplers, are described in detail, for example, in "Theory of Photographic Process" (4th edition, Ed., T. H. James, Macmillan, 1977), pages 291 to 334 and 354 to 361, and in JP-A Nos. 12353/1983, 149046/1983, 149047/1983, 11114/1984, 124399/1984, 174835/1984, 231539/1984, 231540/1994, 2951/1985, 14242/1985, 23474/1985, and 66249/1985.

Examples of couplers that are preferably used in the present invention are listed below:

As couplers that are preferably used in the present invention, compounds having structures described by the following formulae (1) to (12) are mentioned. They are compounds collectively generally referred to as active methylenes, pyrazolones, pyrazoloazoles, phenols, naphthols, and pyrrolotriazoles, respectively, which are compounds known in the art.

 (1)

 (2)

 (3)

 (4)

 (5)

 (6)

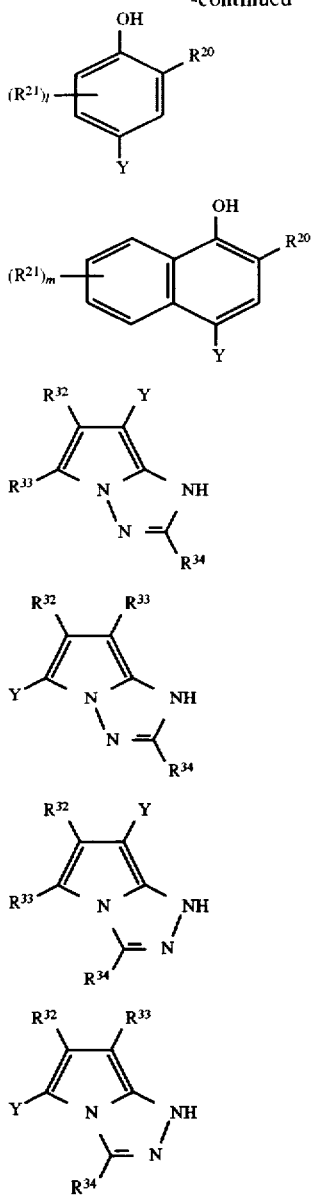

Formulae (1) to (4) represent couplers that are called active methylene couplers, and, in the formulae, $R^{14}$ represents an acyl group, a cyano group, a nitro group, an aryl group, a heterocyclic residue, an alkoxycarbonyl group, an aryloxycarbonyl group, a carbamoyl group, a sulfamoyl group, an alkylsulfonyl group, or an arylsulfonyl group, optionally substitued.

In formulae (1) to (3), $R^{15}$ represents an optionally substituted alkyl group, aryl group, or heterocyclic residue. In formula (4), $R^{16}$ represents an optionally substituted aryl group or heterocyclic residue. Examples of the substituent that may be possessed by $R^{14}$, $R^{15}$, and $R^{16}$ include those mentioned for $X^1$ to $X^5$.

In formulae (1) to (4), Y represents a hydrogen atom or a group capable of coupling split-off by coupling reaction with the oxidized product of the developing agent. Examples of Y are a heterocyclic group (a saturated or unsaturated 5-membered to 7-membered monocyclic or condensed ring having as a hetero atom at least one nitrogen atom, oxygen atom, sulfur atom, or the like, e.g. succinimido, maleinimido, phthalimido, diglycolimido, pyrrole, pyrazole, imidazole, 1,2,4-triazole, tetrazole, indole, benzopyrazole, benzimidazole, benzotriazole, imidazolin-2,4-dione, oxazolidin-2,4-dione, thiazolidin-2,4-dione, imidazolidin-2-one, oxazolin-2-one, thiazolin-2-one, benzimidazolin-2-one, benzoxazolin-2-one, benzthiazolin-2-one, 2-pyrrolin-5-one, 2-imidazolin-5-one, indolin-2,3-dione, 2,6-dioxypurine, parabic acid, 1,2,4-triazolidin-3,5-dione, 2-pyridone, 4-pyridone, 2-pyrimidone, 6-pyridazone, 2-pyrazone, 2-amino-1,3,4-thiazolidine, and 2-imino-1,3,4-thiazolidin-4-one), a halogen atom (e.g. a chlorine atom and a bromine atom), an aryloxy group (e.g. phenoxy and 1-naphthoxy), a heterocyclic oxy group (e.g. pyridyloxy and pyrazolyloxy), an acyloxy group (e.g. acetoxy and benzoyloxy), an alkoxy group (e.g. methoxy and dodecyloxy), a carbamoyloxy group (e.g. N,N-diethylcarbamoyloxy and morpholinocarbonyloxy), an aryloxycarbonyloxy group (e.g. phenylcarbonyloxy), an alkoxycarbonyloxy group (e.g. methoxycarbonyloxy and ethoxycarbonyloxy), an arylthio group (e.g. phenylthio and naphthylthio), a heterocyclic thio group (e.g. tetrazolylthio, 1,3,4-thiadiazolylthio, 1,3,4-oxadiazolylthio, and benzimidazolylthio), an alkylthio group (e.g. methylthio, octylthio, and hexadecylthio), an alkylsulfonyloxy group (e.g. methanesulfonyloxy), an arylsulfonyloxy group (e.g. benzenesulfonyloxy and toluenesulfonyloxy), a carbonamido group (e.g. acetamido and trifluoroacetamido), a sulfonamido group (e.g. methanesulfonamido and benzenesulfonamido), an alkylsulfonyl group (e.g. methanesulfonyl), an arylsulfonyl group (e.g. benzenesulfonyl), an alkylsulfinyl group (e.g. methanesulfinyl), an arylsulfinyl group (e.g. benzenesulfinyl), an arylazo group (e.g. phenylazo and naphthylazo), and a carbamoylamino group (e.g. N-methylcarbamoylamino).

Y may be substituted, and examples of the substituent that may be possessed by Y include those mentioned for $X^1$ to $X^5$.

Preferably Y represents a halogen atom, an aryloxy group, a heterocyclic oxy group, an acyloxy group, an aryloxycarbonyloxy group, an alkoxycarbonyloxy group, or a carbamoyloxy group.

In formulae (1) to (4), $R^{14}$ and $R^{15}$, and $R^{14}$ and $R^{16}$, may bond together to form a ring.

Formula (5) represents a coupler that is called a 5-pyrazolone coupler, and in the formula, $R^{17}$ represents an alkyl group, an aryl group, an acyl group, or a carbamoyl group. $R^{18}$ represents a phenyl group or a phenyl group that is substituted by one or more halogen atoms, alkyl groups, cyano groups, alkoxy groups, alkoxycarbonyl groups, or acylamino groups.

Preferable 5-pyrazolone couplers represented by formula (5) are those wherein $R^{17}$ represents an aryl group or an acyl group, and $R^{18}$ represents a phenyl group that is substituted by one or more halogen atoms.

With respect to these preferable groups, more particularly, $R^{17}$ is an aryl group, such as a phenyl group, a 2-chlorophenyl group, a 2-methoxyphenyl group, a 2-chloro-5-tetradecaneamidophenyl group, a 2-chloro-5-(3-octadecenyl-1-succinimido)phenyl group, a 2-chloro-5-octadecylsulfonamidophenyl group, and a 2-chloro-5-[2-(4-hydroxy-3-t-butylphenoxy)tetradecaneamido]phenyl group; or $R_{17}$ is an acyl group, such as an acetyl group, a 2-(2,4-di-t-pentylphenoxy)butanoyl group, a benzoyl group, and a 3-(2,4-di-t-amylphenoxyacetamidobenzoyl group, any of which may have a substituent, such as a halogen atom or an organic substituent that is bonded through a carbon atom, an oxygen atom, a nitrogen atom, or a sulfur atom. Y has the same meaning as defined above.

Preferably $R^{18}$ represents a substituted phenyl group, such as a 2,4,6-trichlorophenyl group, a 2,5-dichlorophenyl group, and a 2-chlorophenyl group.

Formula (6) represents a coupler that is called a pyrazoloazole coupler, and, in the formula, $R^{19}$ represents a hydrogen atom or a substituent. $Q^3$ represents a group of nonmetal atoms required to form a 5-membered azole ring having 2 to 4 nitrogen atoms, which azole ring may have a substituent (including a condensed ring).

Preferable pyrazoloazole couplers represented by formula (6), in view of spectral absorption characteristics of the color-formed dyes, are imidazo[1,2-b]pyrazoles described in U.S. Pat. No. 4,500,630, pyrazolo[1,5-b]-1,2,4-triazoles described in U.S. Pat. No. 4,500,654, and pyrazolo[5,1-c]-1,2,4-triazoles described in U.S. Pat. No. 3,725,067.

Details of substituents of the azole rings represented by the substituents $R^{19}$ and $Q^3$ are described, for example, in U.S. Pat. No. 4,540,654, the second column, line 41, to the eighth column, line 27. Preferable pyrazoloazole couplers are pyrazoloazole couplers having a branched alkyl group directly bonded to the 2-, 3-, or 6-position of the pyrazolotriazole group, as described in JP-A No. 65245/1986; pyrazoloazole couplers containing a sulfonamido group in the molecule, as described in JP-A No. 65245/1986; pyrazoloazole couplers having an alkoxyphernylsulfonamido ballasting group, as described in JP-A No. 147254/1986; pyrazolotriazole couplers having an alkoxy group or an aryloxy group at the 6-position, as described in JP-A No. 209457/1987 or 307453/1988; and pyrazolotriazole couplers having a carbonamido group in the molecule, as described in Japanese Patent Application No. 22279/1989. Y has the same meaning as defined above.

Formulae (7) and (8) are respectively called phenol couplers and naphthol couplers, and in the formulae $R^{20}$ represents a hydrogen atom or a group selected from the group consisting of —$CONR^{22}R^{23}$, —$SO_2NR^{22}R^{23}$, —$NHCOR^{22}$, —$NHCONR^{22}R^{23}$, and —$NHSO_2NR^{22}R^{23}$. $R^{22}$ and $R^{23}$ each represent a hydrogen atom or a substituent. In formulae (7) and (8), $R^{21}$ represents a substituent, l is an integer selected from 0 to 2, and m is an integer selected from 0 to 4. When l and m are 2 or more, $R^{21}$'s may be different. The substituents of $R^{21}$ to $R^{23}$ include those mentioned above as examples for $X^1$ to $X^5$. Y has the same meaning as defined above.

Preferable examples of the phenol couplers represented by formula (7) include 2-acylamino-5-alkylphenol couplers described, for example, in U.S. Pat. Nos. 2,369,929, 2,801,171, 2,772,162, 2,895,826, and 3,772,002; 2,5-diacylaminophenol couplers described, for example, in U.S. Pat. Nos. 2,772,162, 3,758,308, 4,126,396, 4,334,011, and 4,327,173, West Germany Patent Publication No. 3,329,729, and JP-A No. 166956/1984; and 2-phenylureido-5-acylaminophenol couplers described, for example, in U.S. Pat. Nos. 3,446,622, 4,333,999, 4,451,559, and 4,427,767. Y has the same meaning as defined above.

Preferable examples of the naphthol couplers represented by formula (8) include 2-carbamoyl-1-naphthol couplers described, for example, in U.S. Pat. Nos. 2,474,293, 4,052,212, 4,146,396, 4,282,233, and 4,296,200; and 2-carbamoyl-5-amido-1-naphthol couplers described, for example, in U.S. Pat. No. 4,690,889. Y has the same meaning as defined above.

Formulas (9) to (12) are couplers called pyrrolotriazoles, and $R^{32}$, $R^{33}$, and $R^{34}$ each represent a hydrogen atom or a substituent. Y has the same meaning as defined above. Examples of the substituent of $R^{32}$, $R^{33}$, and $R^{34}$ include those mentioned for $X^1$, $X^2$, $X^3$, $X^4$, and $X^5$. Preferable examples of the pyrrolotriazole couplers represented by formulae (9) to (12) include those wherein at least one of $R^{32}$ and $R^{33}$ is an electron-attracting group, which specific couplers are described in European Patent Nos. 488,248A1, 491,197A1, and 545,300. Y has the same meaning as defined above.

Further, couplers having such structures as a fused-ring phenol, an imidazole, a pyrrole, a 3-hydroxypyridine, an active methylene, an active methine, a 5,5-fused-ring heterocyclic ring, and a 5,6-fused-ring heterocyclic ring, can be used.

As the fused phenol couplers, those described, for example, in U.S. Pat. Nos. 4,327,173, 4,564,586, and 4,904,575 can be used.

As the imidazole couplers, those described, for example, in U.S. Pat. Nos. 4,818,672 and 5,051,347 can be used.

As the 3-hydroxypyridine couplers, those described, for example, in JP-A No. 315736/1989 can be used.

As the active nethylene and active methine couplers, those described, for example, in U.S. Pat. Nos. 5,104,783 and 5,162,196 can be used.

As the 5,5-fused-ring heterocyclic ring couplers, for example, pyrrolopyrazole couplers described in U.S. Pat. No. 5,164,289, and pyrroloimidazole couplers described in JP-A No. 174429/1992, can be used.

As the 5,6-fused ring heterocyclic ring couplers, for example, pyrazolopyrimidine couplers described in U.S. Pat. No. 4,950,585, pyrrolotriazine couplers described in JP-A No. 204730/1992, and couplers described in European Patent No. 556,700, can be used.

In the present invention, in addition to the above couplers, use can be made of couplers described, for example, in West Germany Patent Nos. 3,819,051A and 3,823,049, U.S. Pat. Nos. 4,840,883, 5,024,930, 5,051,347, and 4,481,268, European Patent Nos. 304,856A2, 329,036, 354,549A2, 374,781A2, 379,110A2, and 386,930A1, and JP-A Nos. 141055/1988, 32260/1989, 32261/1989, 297547/1990, 44340/1990, 110555/1990, 7938/1991, 160440/1991, 172839/1991, 172447/1992, 179949/1992, 182645/1992, 184437/1992, 188138/1992, 188139/1992, 194847/1992, 204532/1992, 204731/1992, and 204732/1992.

Specific examples of the couplers that can be used in the present invention are shown below, but, of course, the present invention is not limited to them:

(C-1)

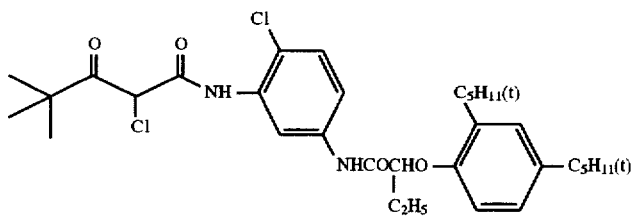

-continued
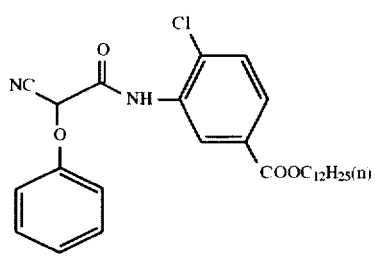
(C-2)
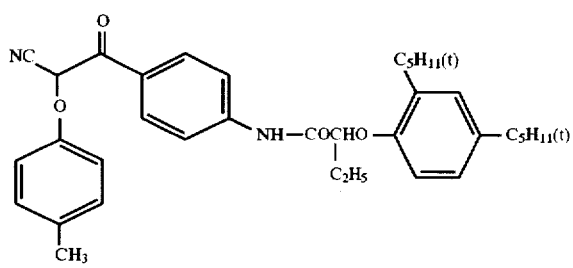
(C-3)
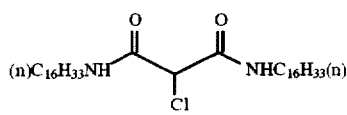
(C-4)
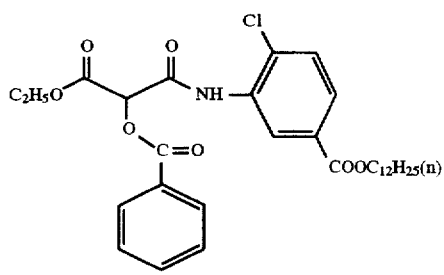
(C-5)
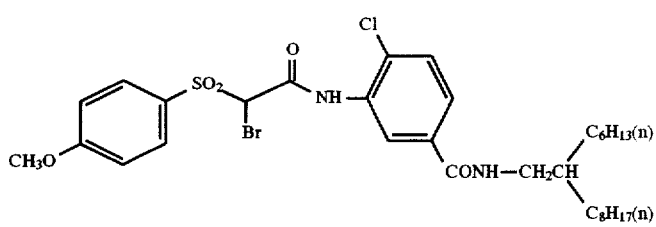
(C-6)
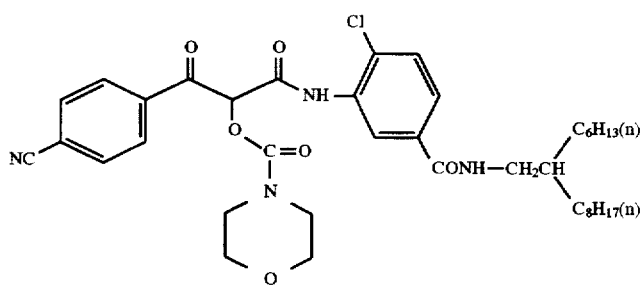
(C-7)

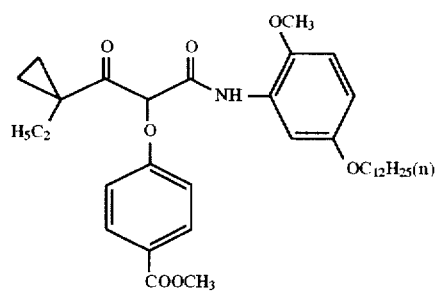
(C-8)
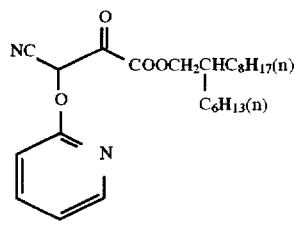
(C-9)
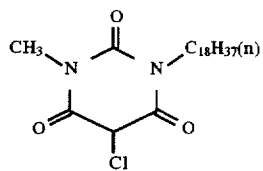
(C-10)
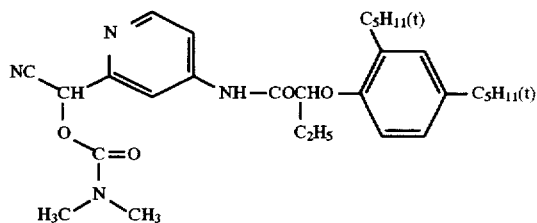
(C-11)
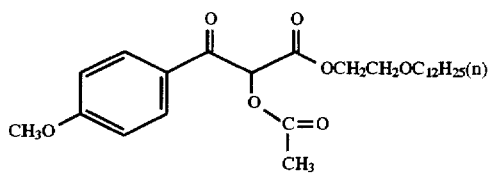
(C-12)
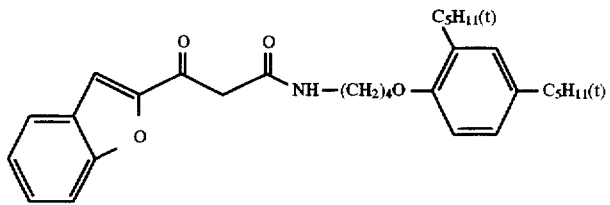
(C-13)
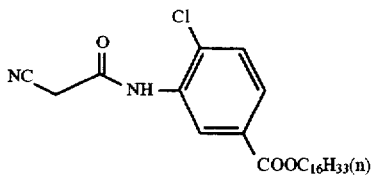
(C-14)

(C-15)
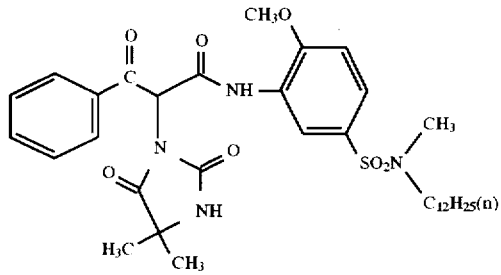
(C-16)
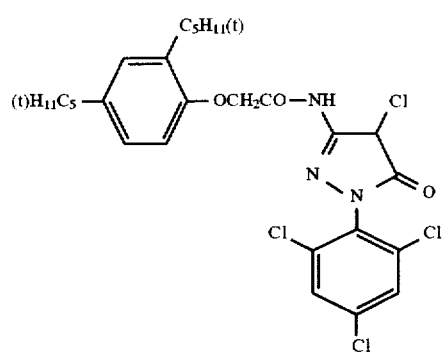
(C-17)
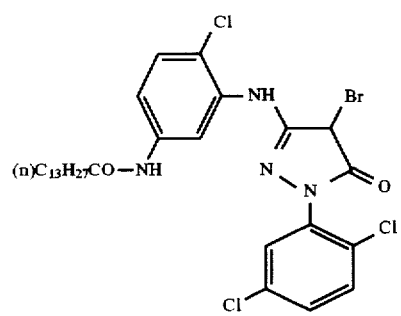
(C-18)
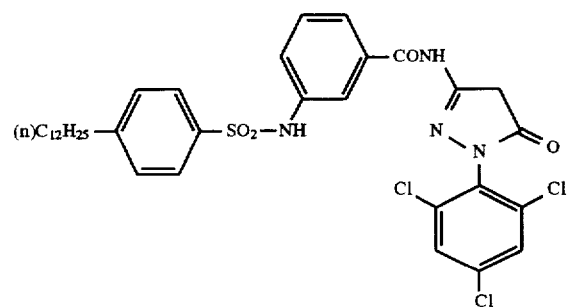
(C-19)
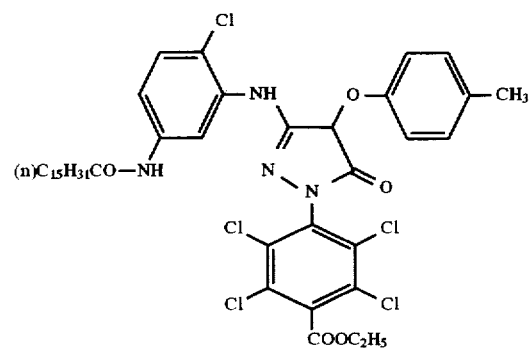

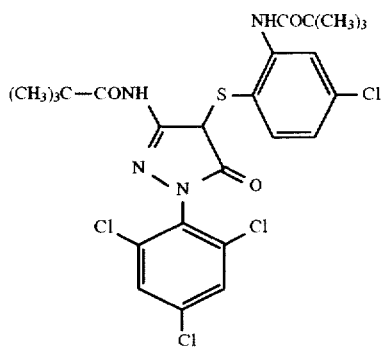
(C-20)
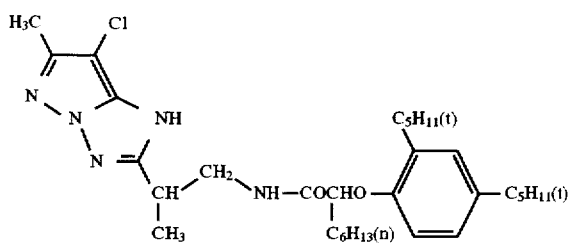
(C-21)
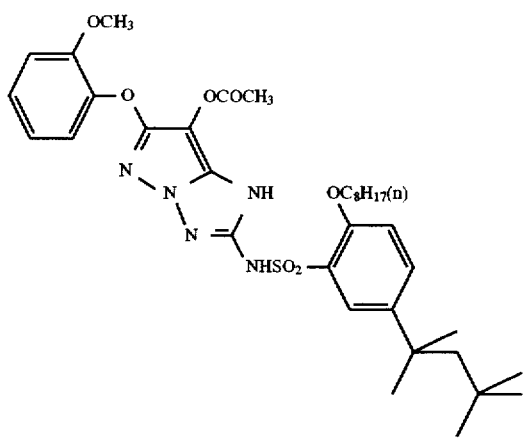
(C-22)
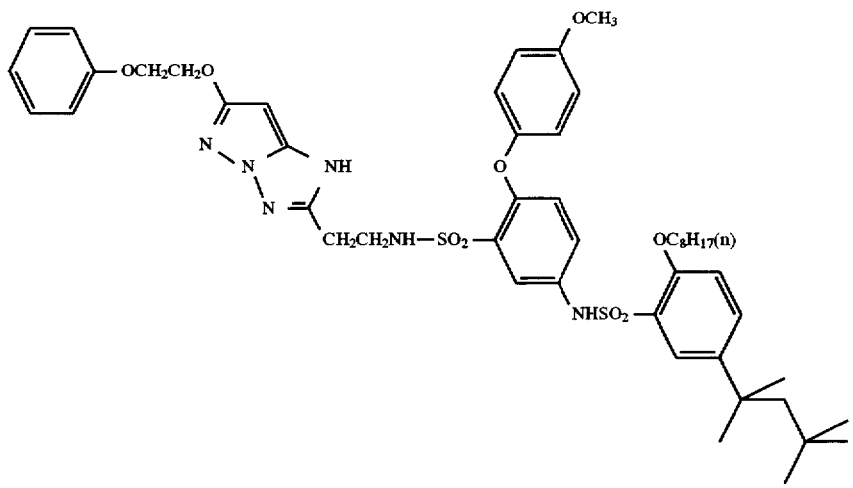
(C-23)

-continued
(C-24)
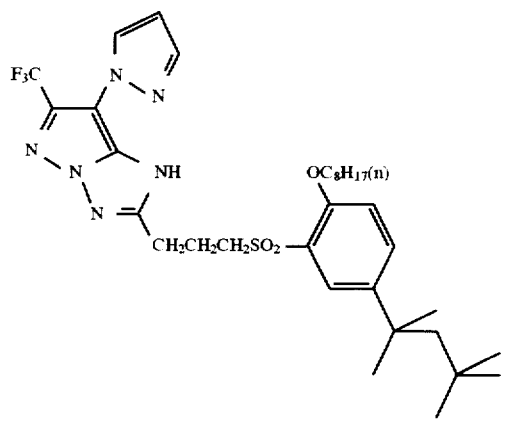
(C-25)
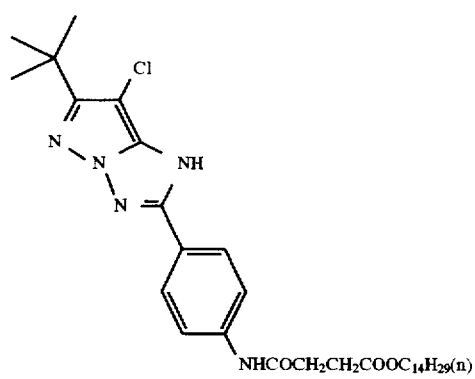
(C-26)
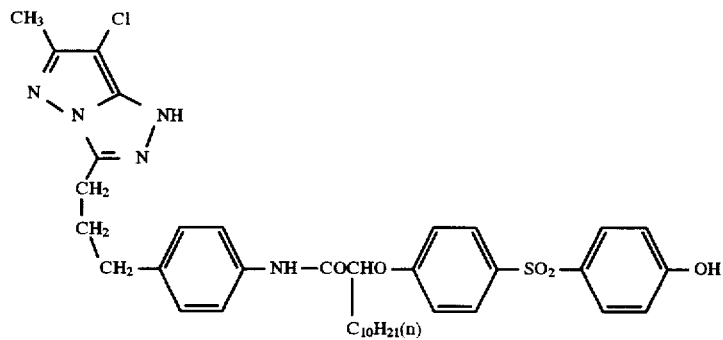

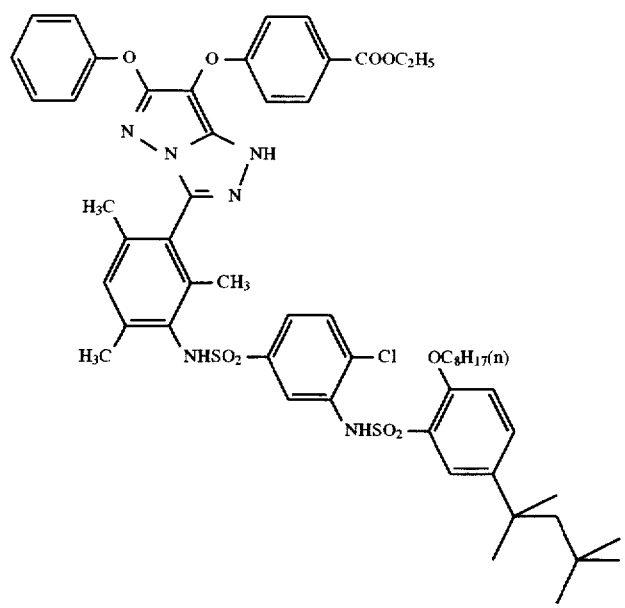
(C-27)
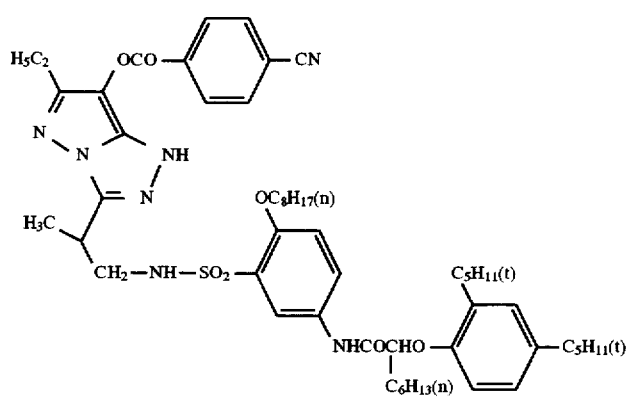
(C-28)
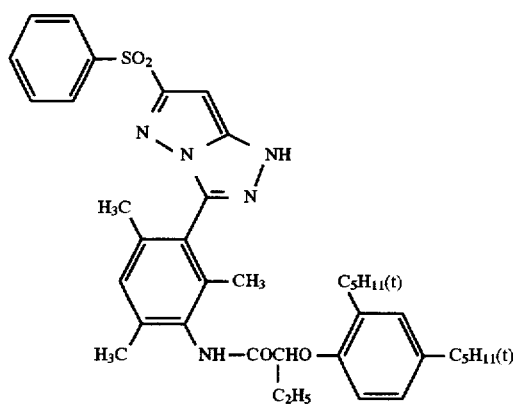
(C-29)

-continued
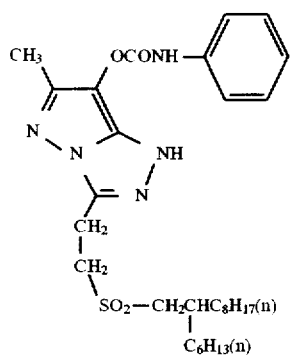
(C-30)
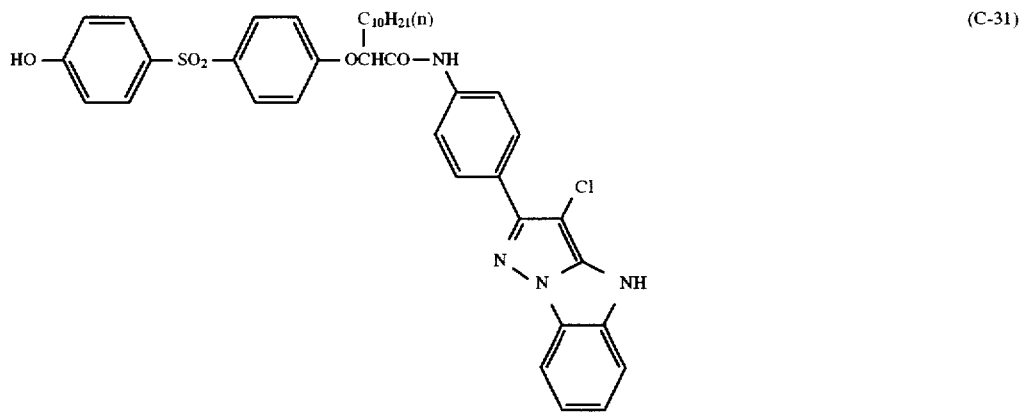
(C-31)
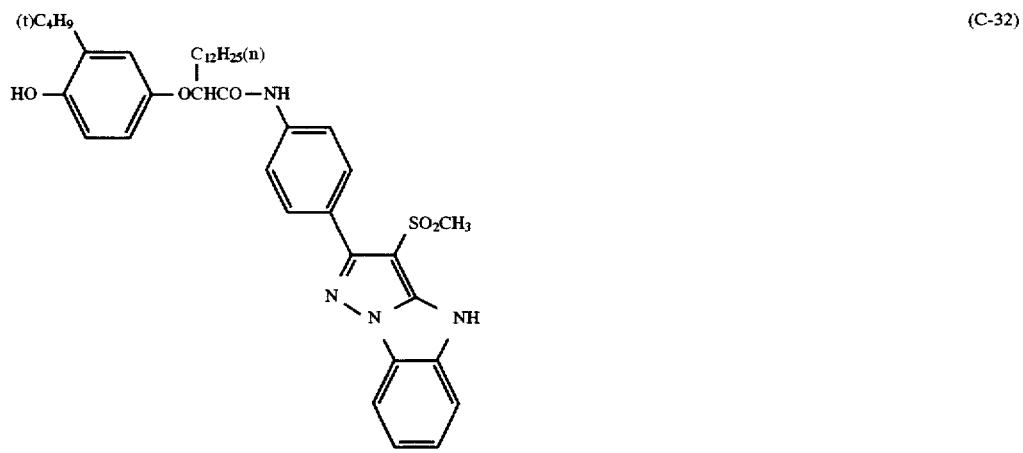
(C-32)
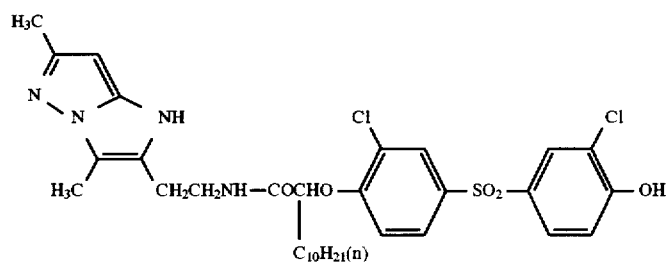
(C-33)

-continued
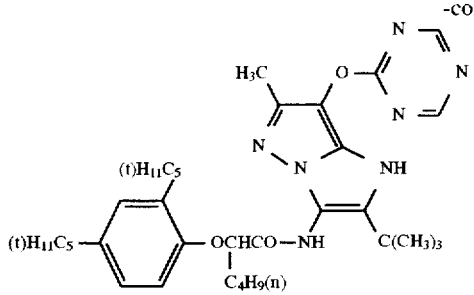 (C-34)
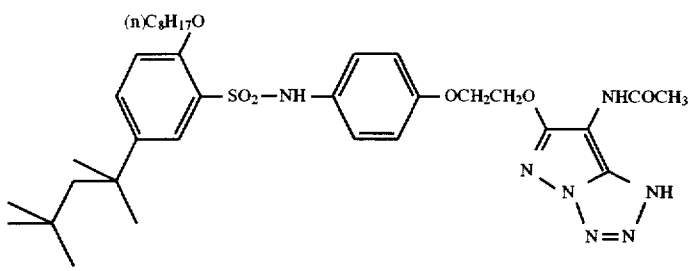 (C-35)
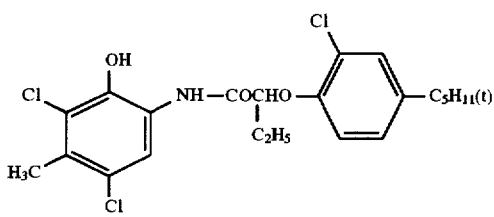 (C-36)
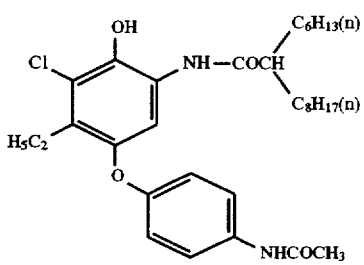 (C-37)
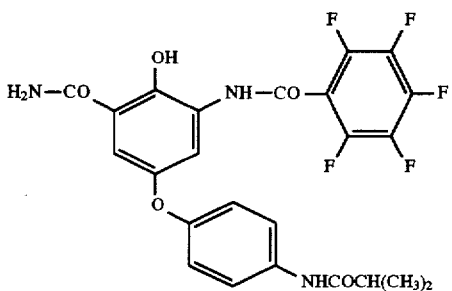 (C-38)
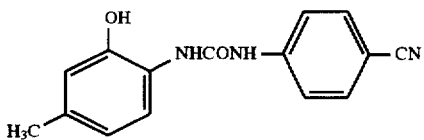 (C-39)
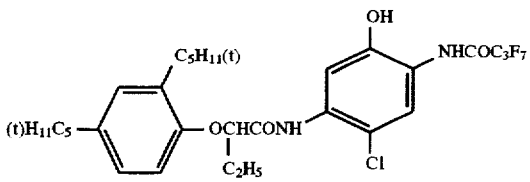 (C-40)

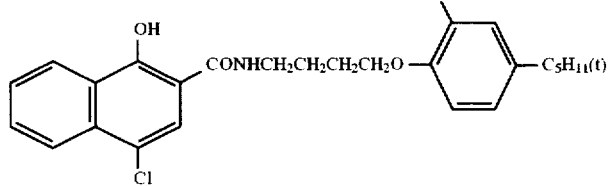 (C-41)
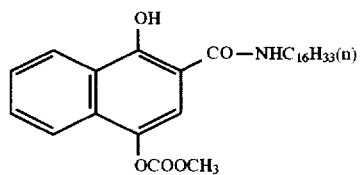 (C-42)
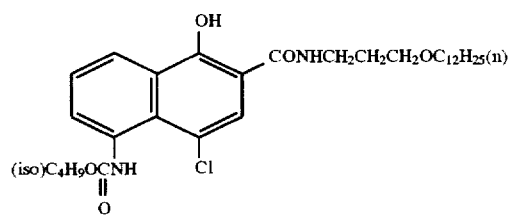 (C-43)
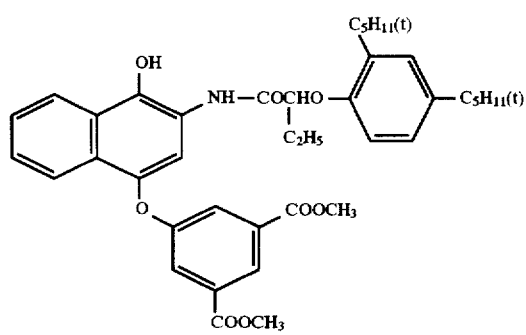 (C-44)
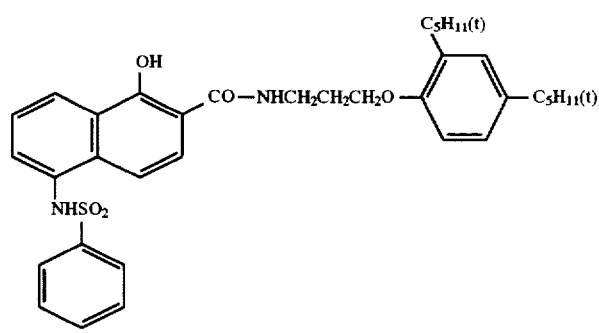 (C-45)

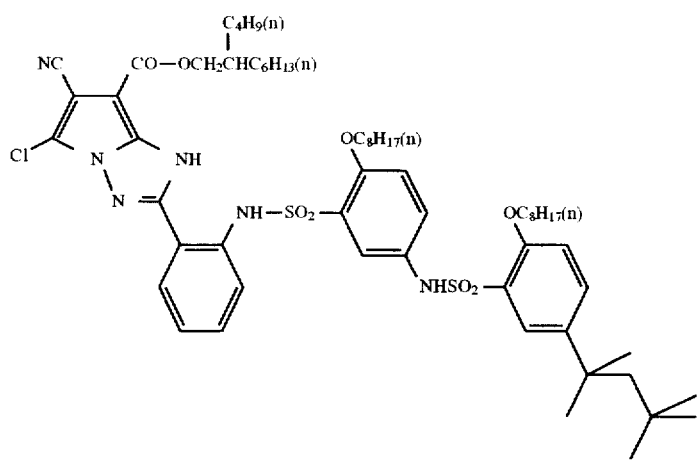
(C-46)
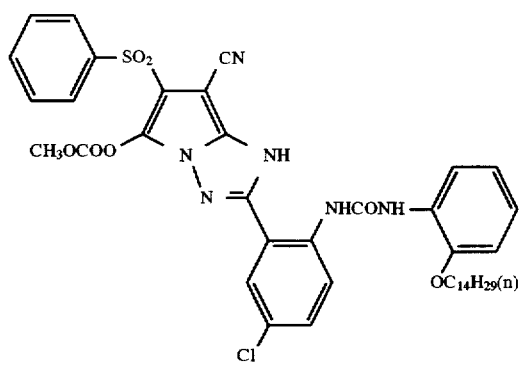
(C-47)
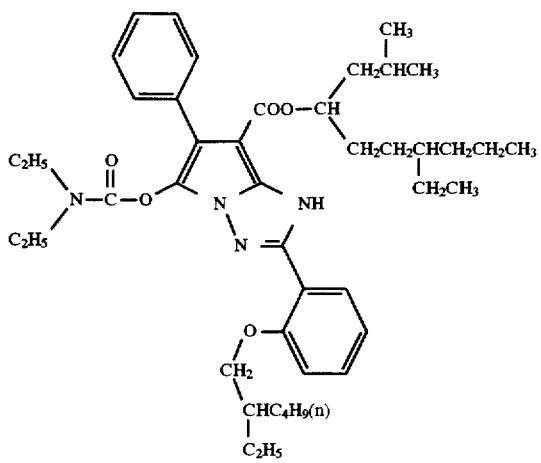
(C-48)
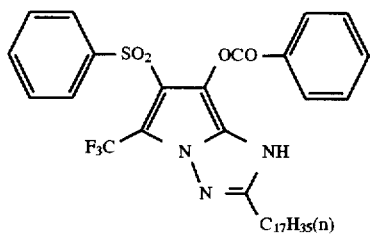
(C-49)

-continued
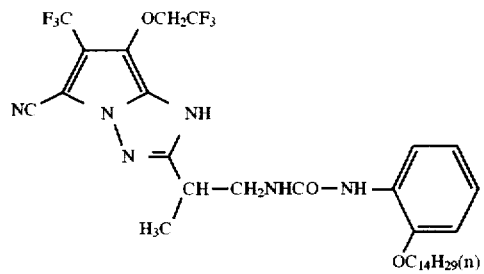
(C-50)
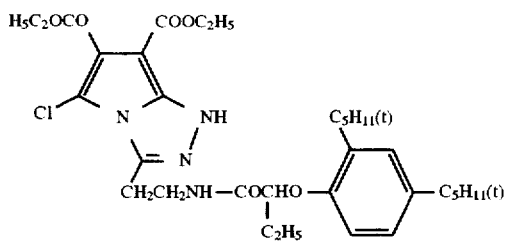
(C-51)
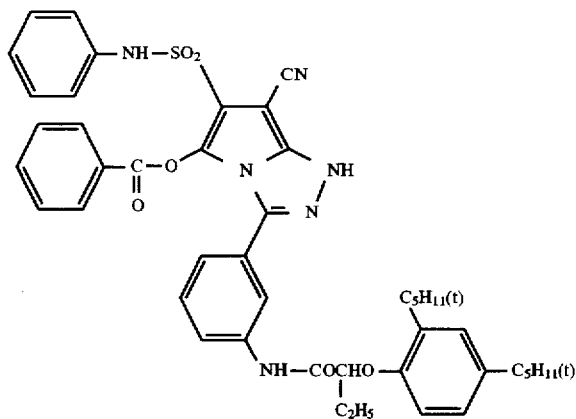
(C-52)
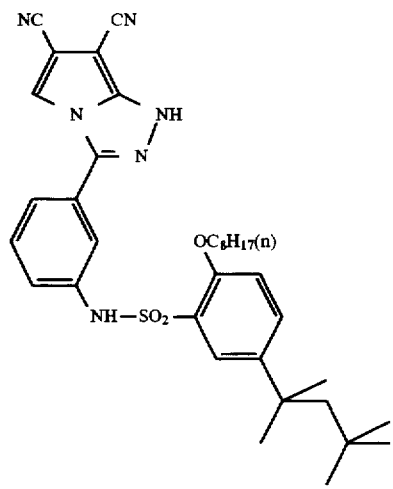
(C-53)

-continued
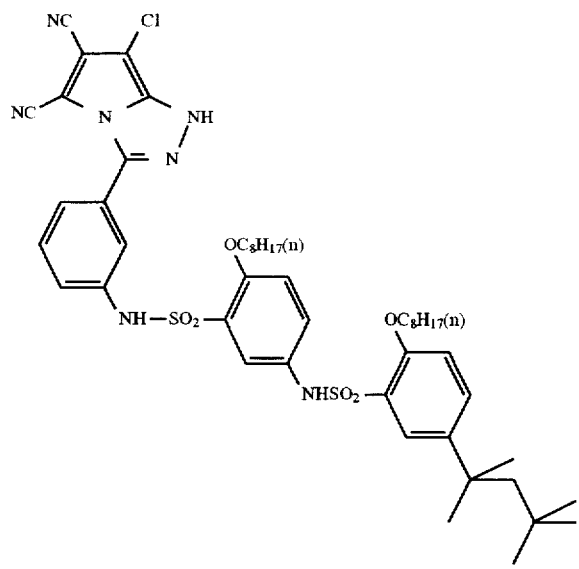
(C-54)
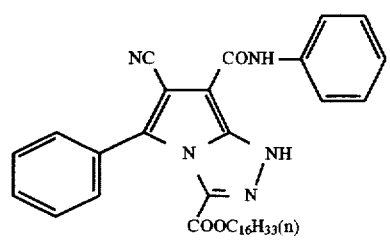
(C-55)
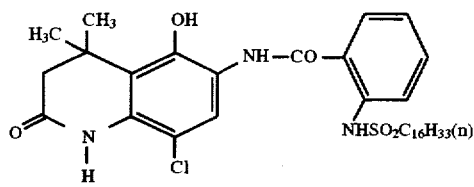
(C-56)
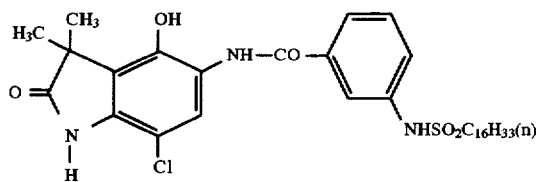
(C-57)
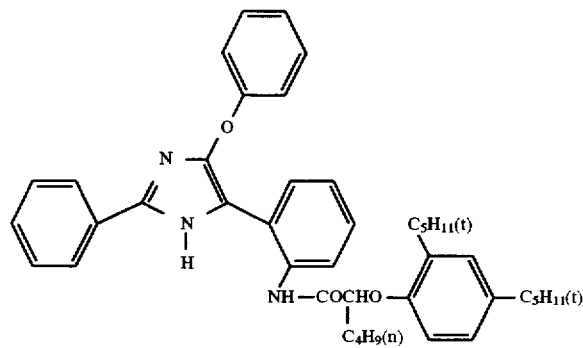
(C-58)

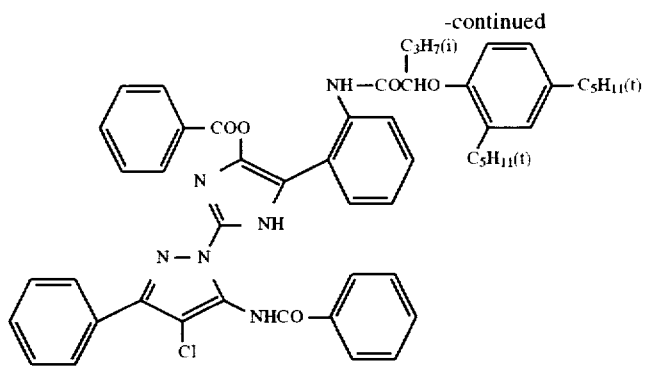
(C-59)
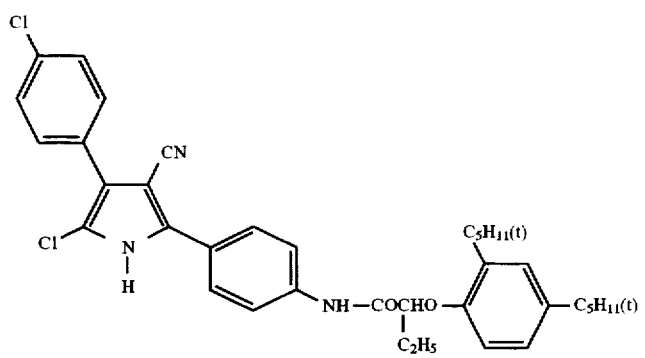
(C-60)
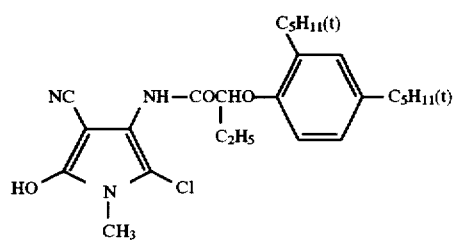
(C-61)
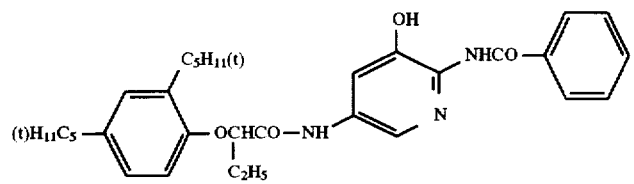
(C-62)
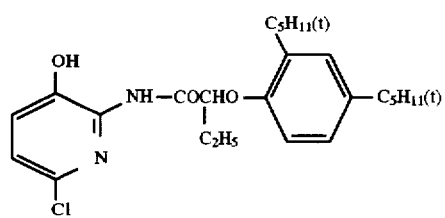
(C-63)
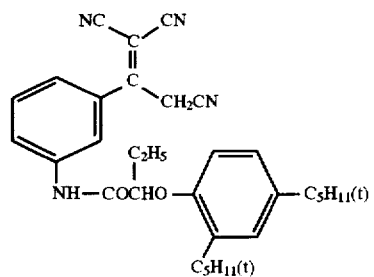
(C-64)

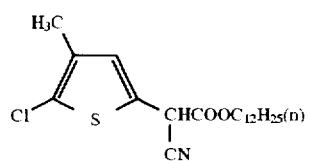
(C-65)
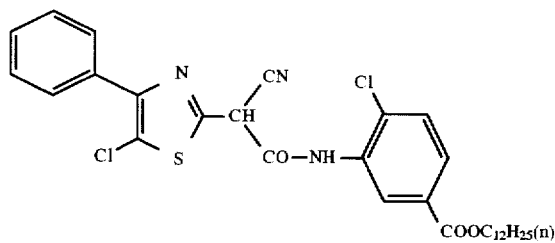
(C-66)
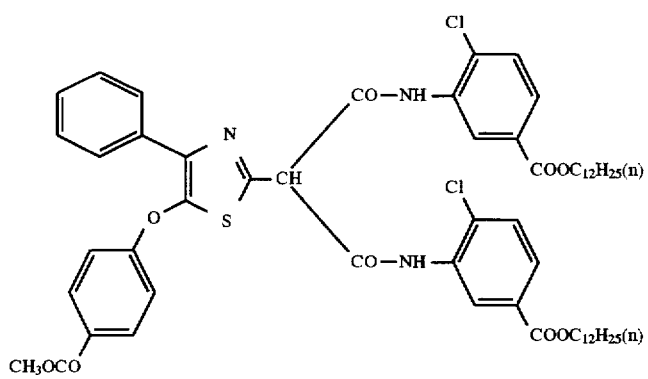
(C-67)
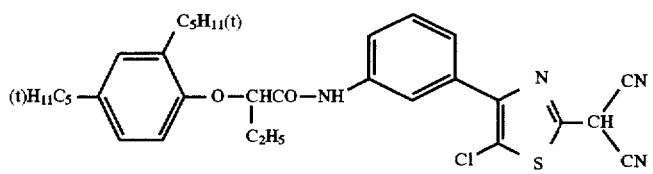
(C-68)
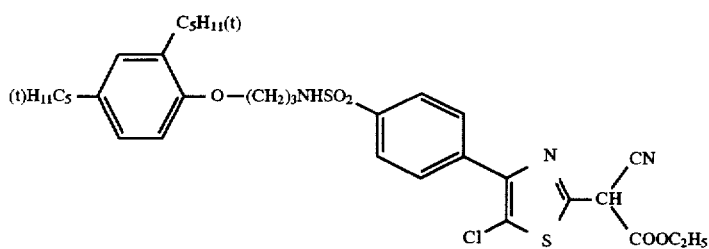
(C-69)
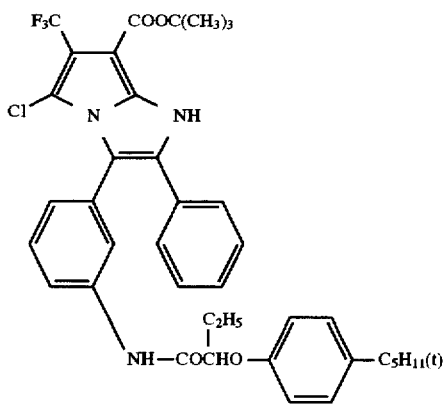
(C-70)

-continued
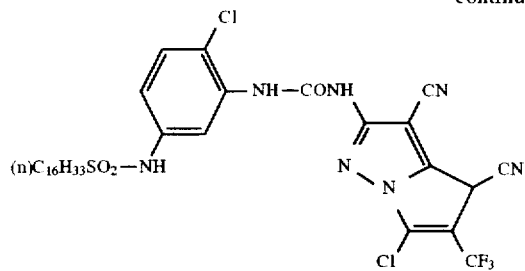
(C-71)
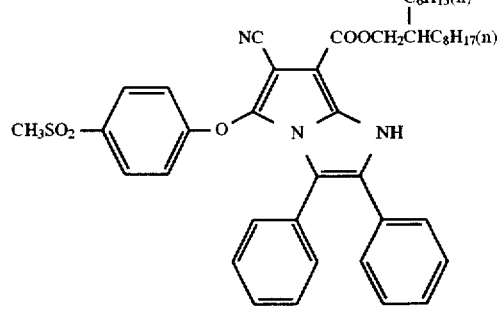
(C-72)
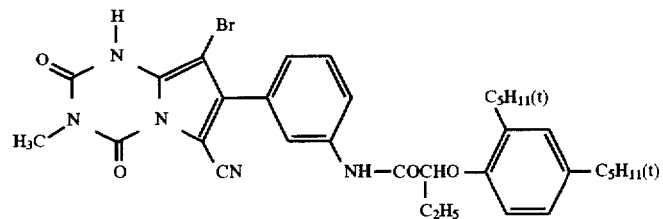
(C-73)
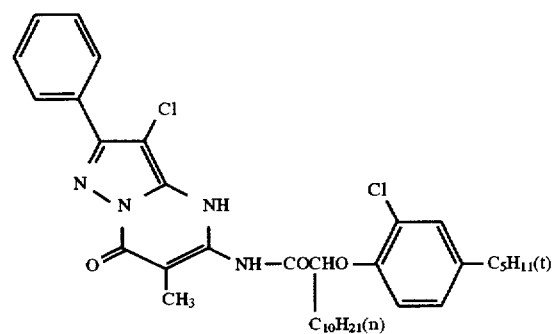
(C-74)
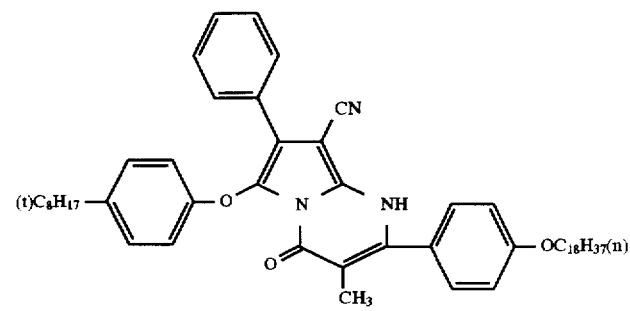
(C-75)
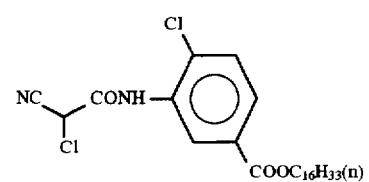
(C-76)

-continued

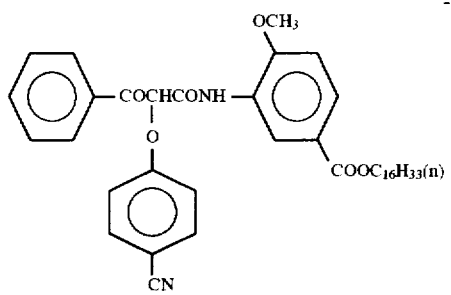 (C-77)

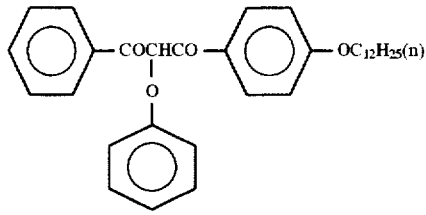 (C-78)

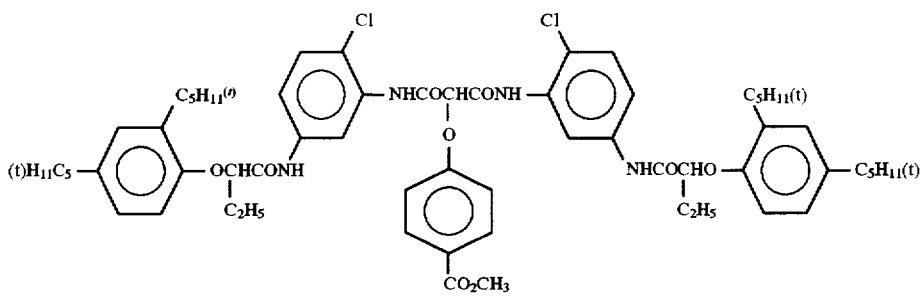 (C-79)

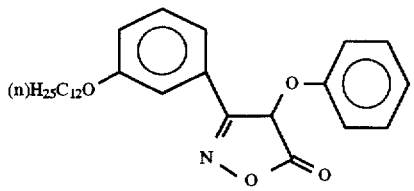 (C-80)

Although the amount to be added, of the couplers that are used in the present invention, varies according to the molar extinction coefficient (ε), in order to obtain an image density of 1.0 or more in terms of reflection density, in the case of couplers wherein the ε of the dye that will be produced by coupling is of the order of 5,000 to 500,000, suitably the amount to be added, of the couplers That are used in the present invention, is of the order of 0.001 to 100 mmol/m$^2$, preferably 0.01 to 10 mmol/m$^2$, and more preferably 0.05 to 5 mmol/m$^2$, in terms of the coated amount.

When the color-developing agent of the present invention is to be contained in a light-sensitive material, it may be contained in any layer (e.g. an emulsion layer and an intermediate layer), and preferably it is contained in an emulsion layer. If there are multiple emulsion layers, preferably the color-developing agent is contained in each of the emulsion layers.

The amount of the color-developing agent of the present invention to be added is 0.01 to 100 times, preferably 0.1 to 10 times, and more preferably 0.2 to 5 times, the amount of the coupler.

The color-developing agent of the present invention can be contained in, instead of a photographic material, a processing solution. In this case, preferably the amount is 0.1 g to 100 g, and more preferably 1 g to 20 g, per liter.

In the present invention, an auxiliary developing agent is preferably used. Herein the term "an auxiliary developing agent" means a substance that promotes the transfer of electrons from the color-developing agent to silver halides in the development process of the silver halide development; and in the present invention, preferably the auxiliary developing agent is a compound capable of releasing electrons according to the Kendall-Pelz rule, which compound is represented preferably by formula (B-1) or (B-2).

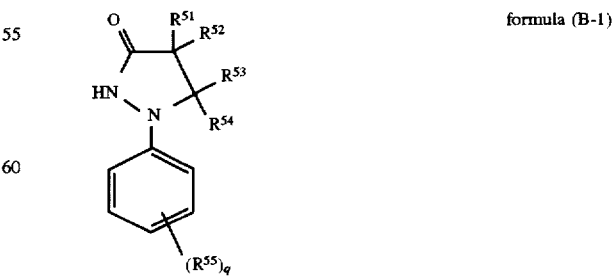

formula (B-1)

formula (B-2)

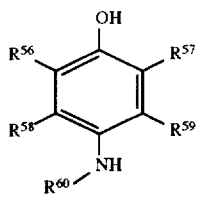

In formulae (B-1) and (B-2), $R^{51}$ to $R^{54}$ each represent a hydrogen atom, an alkyl group, a cycloalkyl group, an alkenyl group, an aryl group, or a heterocyclic group.

$R^{55}$ to $R^{59}$ each represent a hydrogen atom, a halogen atom, a cyano group, an alkyl group, a cycloalkyl group, an alkenyl group, an aryl group, a heterocyclic group, an alkoxy group, a cycloalkyloxy group, an aryloxy group, a heterocyclic oxy group, a silyloxy group, an acyloxy group, an amino group, an anilino group, a heterocyclicamino group, an alkylthio group, an arylthio group, a heterocyclicthio group, a silyl group, a hydroxyl group, a nitro group, an alkoxycarbonyloxy group, a cycloalkyloxycarbonyloxy group, an aryloxycarbonyloxy group, a carbamoyloxy group, a sulfamoyloxy group, an alkanesulfonyloxy group, an arylenesulfonyloxy group, an acyl group, an alkoxycarbonyl group, a cycloalkyloxycarbonyl group, an aryloxycarbonyl group, a carbamoyl group, a carbonamido group, a ureido group, an imido group, an alkoxycarbonylamino group, an aryloxycarbonylamino group, a sulfonamido group, a sulfamoylamino group, an alkylsulfinyl group, an arenesulfinyl group, an alkanesulfonyl group, an arenesulfonyl group, a sulfamoyl group, a sulfo group, a phosphinoyl group, or a phosphinoylamino group.

q is an integer of 0 to 5, and when q is 2 or more, $R^{55}$'s may be different. $R^{60}$ represents an alkyl group or an aryl group.

Compounds represented by formula (B-1) or (B-2) are shown specifically below, but the auxiliary developing agent used in the present invention is not limited to these specific examples.

(ETA-1)

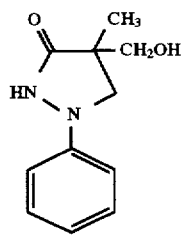

(ETA-2)

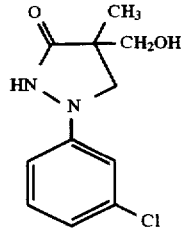

(ETA-3)

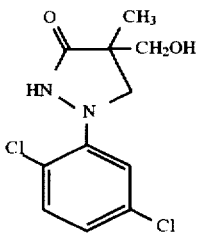

(ETA-4)

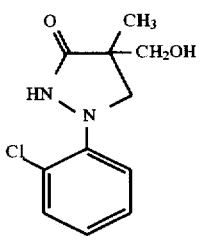

(ETA-5)

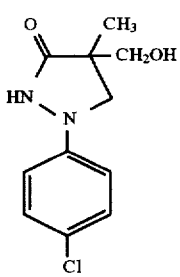

(ETA-6)

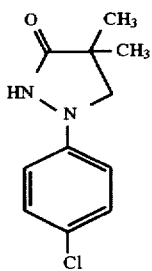

(ETA-7)

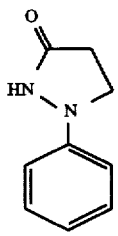

(ETA-8)

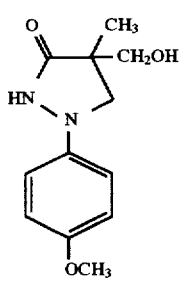

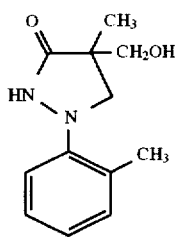
(ETA-9)
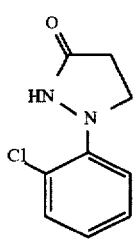
(ETA-10)
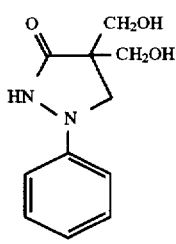
(ETA-11)
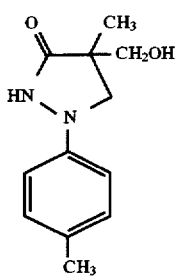
(ETA-12)
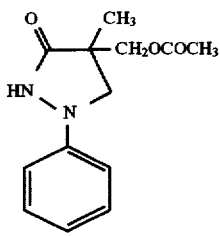
(ETA-13)
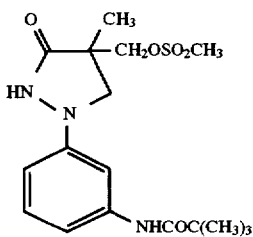
(ETA-14)
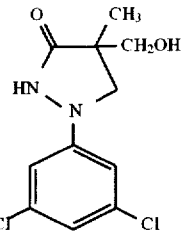
(ETA-15)
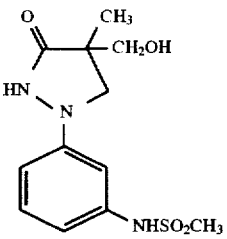
(ETA-16)
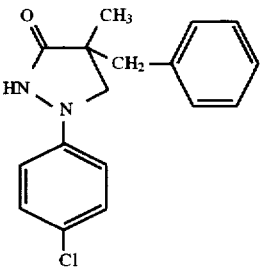
(ETA-17)
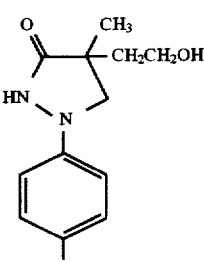
(ETA-18)
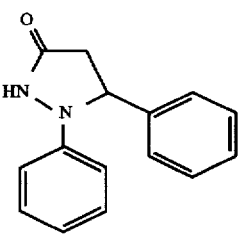
(ETA-19)
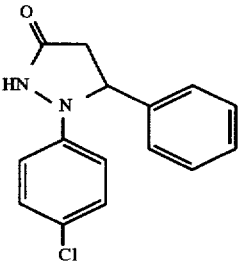
(ETA-20)

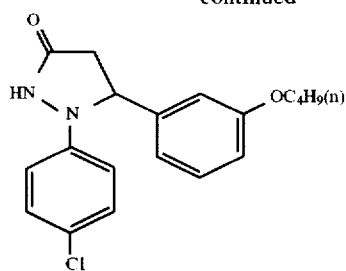
(ETA-21)
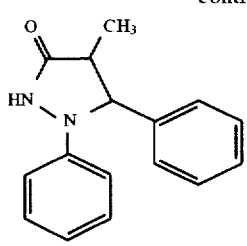
(ETA-27)
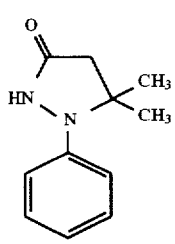
(ETA-28)
(ETA-22)
(ETA-23)
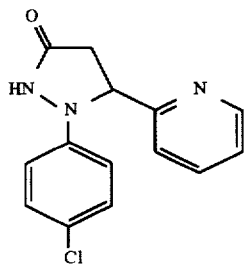
(ETA-29)
(ETA-24)
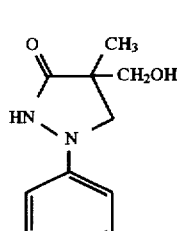
(ETA-30)
(ETA-25)
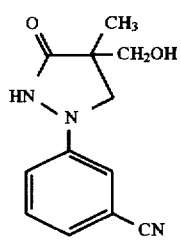
(ETA-31)
(ETA-26)
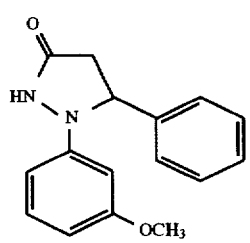
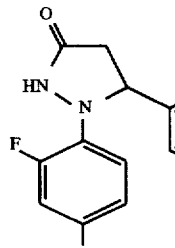
(ETA-32)

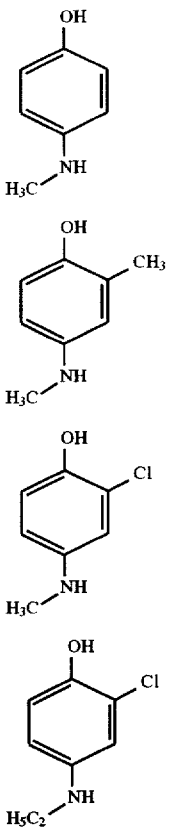

(ETA-33)

(ETA-34)

(ETA-35)

(ETA-36)

In the present invention, a blocked photographic reagent, represented by formula (A), that will release a photographically useful group at the time of processing, can be used:

Formula (A):

A—(L)$_n$-PUG

A represents a blocking group whose bond to (L)$_n$-PUG will be split off at the time of development processing; L represents a linking group whose right bond (in the above formula (A)) will be split off after the bond on the left of L is split off; n is an integer of 0 to 3; and PUG represents a photographically useful group.

Groups represented by formula (A) will now be described.

As the blocking group represented by A, the following already known groups can be used: blocking groups described, for example, in JP-B No. 9968/1973, JP-A Nos. 8828/1977 and 82834/1982, U.S. Pat. No. 3,311,476, and JP-B No. 44805/1972 (U.S. Pat. No. 3,615,617), such as an acyl group and a sulfonyl group; blocking groups that use the reverse Michael reaction, as described, for example, in JP-B Nos. 17369/1980 (U.S. Pat. No. 3,888,677), 9696/1980 (U.S. Pat. No. 3,791,830), and 34927/1980 (U.S. Pat. No. 4,009,029), and JP-A Nos. 77842/1981 (U.S. Pat. No. 4,307,175), 105640/1984, 105641/1984, and 105642/1984; blocking groups that use the formation of quinone methide, or a compound similar to quinone methide, by intramolecular electron transfer, as described, for example, in JP-B No. 39727/1979, U.S. Pat. Nos. 3,674,478, 3,932,480, and 3,993,661, and JP-A Nos. 135944/1982, 135,945/1982 (U.S. Pat. No. 4,420,554), 136640/1982, 196239/1986, 196240/1986 (U.S. Pat. No. 4,702,999), 185743/1986, 124941/1986 (U.S. Pat. No. 4,639,408), and 280140/1990; blocking groups that use intramolecular nucleophilic replacement reaction, as described, for example, in U.S. Pat. Nos. 4,358, 525 and 4,330,617, and JP-A Nos. 53330/1980 (U.S. Pat. No. 4,310,612), 121328/1984, 218439/1984, and 318555/1988 (European Publication Patent No. 0295729); blocking groups that use ring cleavage of a 5-membered ring or 6-membered ring, as described, for example, in JP-A Nos. 76541/1982 (U.S. Pat. No. 4,335,200), 135949/1982 (U.S. Pat. No. 4,350,752), 179842/1982, 137945/1984, 140445/1984, 219741/1984, 202459/1984, 41034/1985 (U.S. Pat. No. 4,618,563), 59945/1987 (U.S. Pat. No. 4,888,268), 65039/1987 (U.S. Pat. No. 4,772,537), 80647/1987, 236047/1991, and 238445/1991; blocking groups that use the addition reaction of a nucleophilic reagent to a conjugated unsaturated bond, as described, for example, in JP-A Nos. 201057/1984 (U.S. Pat. No. 4,518,685), 95346/1986 (U.S. Pat. No. 4,690,885), 95347/1986 (U.S. Pat. No. 4,892,811), 7035/1989, 42650/1989 (U.S. Pat. No. 5,066,573), 245255/1989, 207249/1990, 235055/1990 (U.S. Pat. No. 5,118,596), and 186344/1992; blocking groups that use the β-elimination reaction, as described, for example, in JP-A Nos. 93442/1984, 32839/1986, and 163051/1987, and JP-B No. 37299/1993; blocking groups that use the nucleophilic replacement reaction of diarylmethanes, as described in JP-A No. 188540/1986; blocking groups that uses the Lossen rearrangement reaction, as described in JP-A No 187850/1987; blocking groups that use the reaction between the N-acylated product of thiazolidin-2-thion and amines, as described in JP-A Nos. 80646/1987, 144163/1987, and 147457/1987; and blocking groups that have two nucleophilic groups to react with two nucleophilic agents, as described in JP-A Nos. 296240/1990 (U.S. Pat. No. 5,019, 492), 177243/1992, 177244/1992, 177245/1992, 177246/1992, 177247/1992, 177248/1992, 177249/1992, 179948/1992, 184337/1992, and 184338/1992, International Publication Patent No. 92/21064, JP-A No. 330438/1992, International Publication Patent No. 93/03419, and JP-A No. 45816/1993, as well as JP-A Nos. 236047/1991 and 238445/1991.

The group represented by L in the compound represented by formula (A) may be any linking group that can be split off from the group represented by A, at the time of development processing, and that then can split (L)$_n$-1-PUG. Examples are groups that use the split of a hemi-acetal ring, as described in U.S. Pat. Nos. 4,146,396, 4,652,516, and 4,698,297; timing groups that bring about an intramolecular nucleophilic substitution reaction, as described in U.S. Pat. Nos. 4,248,962, 4,847,185, or 4,857,440; timing groups that use an electron transfer reaction to bring about a cleavage reaction, as described in U.S. Pat. No. 4,409,323 or 4,421, 845; groups that use the hydrolysis reaction of an iminoketal to bring about a cleavage reaction, as described in U.S. Pat. No. 4,546,073; groups that use the hydrolysis reaction of an ester to bring about a cleavage reaction, as described in West German Publication Patent No. 2,626,317; or groups that use a reaction with sulfite ions to bring about a cleavage reaction, as described in European Patent No. 0572084.

PUG in formula (A) will now be described.

PUG in formula (A) represents a group photographically useful for an antifoggant, a photographic dye, and the like, and in the present invention the auxiliary developing agents represented by formula (B-1) or (B-2) are particularly preferably used for PUG.

When the auxiliary developing agents represented by formula (B-1) or (B-2) correspond to PUG of formula (A), the bonding position is at the oxygen atom or nitrogen atom of the auxiliary developing agent.

The photographic material (light-sensitive material) of the present invention, basically, has on a base, a photosensitive silver halide, a color-developing agent, couplers, a binder, and, if required, an organic metal salt oxidant, and the like. In many cases, these components are added to the same layer, but they can be separated added to different layers if they are in reactive states.

Hydrophobic additives used in the present invention, such as couplers and the color-developing agent, can be introduced into layers of a photographic material by a known method, such as the one described in U.S. Pat. No. 2,322,027. In this case, use is made of a high-boiling organic solvent as described, for example, in U.S. Pat. Nos. 4,555,470, 4,536,466, 4,536,467, 4,587,206, 4,555,476, and 4,599,296, and JP-B No. 62,256/1991, if necessary, in combination with a low-boiling organic solvent having a boiling point of 50° to 160° C. These dye-donative compounds, diffusion-proof reducing agents, high-boiling organic solvents, and the like can be used in the form of a combination of two or more.

The high-boiling organic solvent is used in an amount of 10 g or less, preferably 5 g or less, and more preferably 1 g to 0.1 g, per g of the compound for forming a color image. The amount is also suitably 1 cc or less, particularly 0.5 cc or less, and more particularly 0.3 cc or less, per g of the binder.

A dispersion method that use a polymer, as described in JP-B No. 39,853/1976 and JP-A No. 59,943/1976, and a method wherein the addition is made with them in the form of a dispersion of fine particles, as described, for example, in JP-A Nos. 30,242/1987 and 271339/1988, can also be used.

If the compounds are substantially insoluble in water, besides the above methods, a method can be used wherein the compounds may be made into fine particles to be dispersed and contained in a binder.

In dispersing the hydrophobic compound in a hydrophilic colloid, various surface-active agents can be used; examples are listed in JP-A No. 157,636/1984, pages 37 to 38, and in the RD publication shown in a table below.

In the photographic material of the present invention, use can be made of a compound that can activate the development and make the image stable. Preferable specific compounds for use are described in U.S. Pat. No. 4,500,626, the 51st column to the 52nd column.

In order to obtain colors ranging widely on the chromaticity diagram by using three primary colors: yellow, magenta, and cyan, use is made of a combination of at least three silver halide emulsion layers photosensitive to respectively different spectral regions. For examples, a combination of three layers of a blue-sensitive layer, a green-sensitive layer, and a red-sensitive layer, and a combination of a green-sensitive layer, a red-sensitive layer, and an infrared-sensitive layer, can be mentioned. The photosensitive layers can be arranged in various orders known generally for color photographic materials. Further, each of these layers can be divided into two or more layers if necessary.

In the photographic material, various auxiliary layers can be provided, such as a protective layer, an underlayer, an intermediate layer, an antihalation layer, and a back layer. Further, in order to improve the color separation, various filter dyes can be added.

The silver halide grains used in the present invention are made of silver bromide, silver chloride, silver chlorobromide, silver chloroiodide, silver iodobromide, or silver chloroiodobromide. Other silver salts, such as silver rhodanate, silver sulfide, silver selenide, silver carbonate, silver phosphate, or a silver salt of an organic acid, may be contained in the form of independent grains or as part of silver halide grains. If it is desired to make the development/desilvering (bleaching, fixing, and bleach-fix) step rapid, silver halide grains having a high silver chloride content are desirable. Further, if the development is to be restrained moderately, it is preferable to contain silver iodide. The preferable silver iodide content varies depending on the intended photographic material. For example, in the case of X-ray photographic materials, the preferable silver iodide content is in the range of 0.1 to 15 mol %, and in the case of graphic art and micro photographic materials, the preferable silver iodide content is in the range of 0.1 to 5 mol %. In the case of photographic materials represented by color negatives, preferably silver halide contains 1 to 30 mol %, more preferably 5 to 20 mol %, and particularly preferably 8 to 15 mol %, of silver iodide. It is preferable to incorporate silver chloride in silver iodobromide grains, because the lattice strain can be made less intense.

The grains of the silver halide emulsion of the present invention preferably have a distribution or a structure with respect to the halogen composition. Typical examples thereof are grains having a double structure, or core-shell-type grains wherein the halogen composition is different; in the surface layer and the inside part of the grains, as disclosed, respectively, in JP-B No. 13162/1968 and in JP-A Nos. 215540/1986, 222845/1985, and 75337/1986. Instead of a simple double structure, a triple structure, as described in JP-A No. 222844/1985, an even larger-number multilayer structure, or a structure wherein the surface of grains having a core-shell double structure has a thin silver halide layer different in composition from that of the said surface, can be used.

In order to make the inside of grains have a structure, not only the enclosing structure, as mentioned above, but also a so-call junctioned structure can be used to form grains. Examples thereof are disclosed, for example, in JP-A Nos. 133540/1984 and 108526/1983, European Patent No. 199, 290A2, JP-B No. 24772/1983, and JP-A No. 16254/1984. Crystals to be junctioned have a composition different from that of host crystals, and they can be junctioned and formed at the edges, corners, or planes of the host crystals. Such junctioned crystals can be formed if host crystals have a uniform halogen composition or a core-shell-type structure.

In the case of a junctioned structure, not only a combination of silver halides but also a combination of a silver halide with a silver salt compound having no rock salt structure, such as silver rhodanate and silver carbonate, can be used for the Functioned structure. A non-silver salt compound, such as lead oxide, may be used if a junctioned structure is possible.

In the case of grains of silver iodobromide or the like having these structures, a preferable mode is that the core part is higher in silver iodide content than the shell part. Reversely, in some cases, grains having a lower silver iodide content in the core part than in the shell part are preferable. Similarly, in the case of grains having a junctioned structure, the silver iodide content of the host crystals is relatively higher than that of the junctioned crystals, or this may be reversed. The boundary part of the grains having these structures in which different halogen compositions are present, may be distinct or indistinct. Also preferable is a mode wherein the composition is continuously changed positively.

It is important that in the case of that two or more silver halides are present as mixed crystals, or as silver halide grains having structures, the halogen composition distribution between grains is controlled. The method of measuring the halogen composition distribution between grains is described in JP-A No. 254032/1985. A desirable property is that the halogen distribution between grains is uniform. In particular, a highly uniform emulsion having a deviation coefficient of 20% or below is preferable. Another preferable mode is an emulsion in which the grain size and the halogen composition are correlated. An example correlation is a larger grain size with a larger iodine content, and vice versa (smaller grain size, lower iodine content). Depending on the purpose, the reversed correlation or a correlation using some other halogen composition can be used. For this purpose, it is preferable to mix two or more emulsions different in composition.

It is important to control the silver halide composition near the surface of grains. An increase in the silver iodide content or the silver chloride content at the part near the surface changes the adsorption of a dye or the developing speed. Therefore the silver halide composition can be chosen in accordance with the purpose. To change the halogen composition at the part near the surface, either the structure enclosing the whole of a grain or the structure wherein only part of a grain is attached another silver halide different in halogen composition, can be chosen. For example, in the case of a tetradecahedral grain having (100) and (111) planes, only one plane is changed in halogen composition, or in another case, one of the main plane and the side plane of a tabular grain is changed in halogen composition.

In the silver halide grains used in the present invention, in accordance with the purpose, any of regular crystals having no twin plane, and those described in "Shashin Kogyo no Kiso, Ginen Shashin-hen", edited by Nihon Shashin-gakkai (Corona Co.), page 163, such as single twins having one twin plane, parallel multiple twins having two or more parallel twin planes, and nonparallel multiple twins having two or more nonparallel twin planes, can be chosen and used. An example in which grains different in shape are mixed is disclosed in U.S. Pat. No. 4,865,964, and if necessary this method can be chosen. In the case of regular crystals, cubes having (100) planes, octahedrons having (111) planes, and dodecahedral grains having (110) planes, as disclosed in JP-B No. 42737/1980 and JP-A No. 222842/1985, can be used. Further, (h11) plane grains represented by (211), (hh1) plane grains represented by (331), (hk0) plane grains represented by (210) planes, and (hk1) plane grains represented by (321) planes, as reported in "Journal of Imaging Science", Vol. 30, page 247 (1986), can be chosen and used in accordance with the purpose, although the preparation is required to be adjusted. Grains having two or more planes in one grain, such as tetradecahedral grains having (100) and (111) planes in one grain, grains having (100) and (110) planes in one grain, or grains having (111) and (110) planes in one grain, can be chosen and used in accordance with the purpose.

The value obtained by dividing the diameter of the projected area, which is assumed to be a circle, by the thickness of the grain, is called an aspect ratio, which defines the shape of tabular grains. Tabular grains having an aspect ratio of 1 or more can be used in the present invention. Tabular grains can be prepared by methods described, for example, by Cleav in "Photography Theory and Practice" (1930), page 131; by Gutof in "Photographic Science and Engineering", Vol. 14, pages 248 to 257 (1970); and in U.S. Pat. Nos. 4,434,226, 4,414,310, 4,433,048, and 4,439,520, and British Patent No. 2,112,157. When tabular grains are used, such merits are obtained that the covering power is increased and the color sensitization efficiency due to a sensitizing dye is increased, as described in detail in the above-mentioned U.S. Pat. No. 4,434,226. The average aspect ratio of 80% or more of all the projected areas of grains is desirably 1 or more but less than 100, more preferably 2 or more but less than 20, and particularly preferably 3 or more but less than 10. As the shape of average grains, a triangle, a hexagon, a circle, and the like can be chosen. A regular hexagonal shape having six approximately equal sides, described in U.S. Pat. No. 4,798,354, is a preferable mode.

In many cases, the grain size of average grains is expressed by the diameter of the projected area assumed to be a circle, and grains having an average diameter of 0.6 microns or below, as described in U.S. Pat. No. 4,748,106, are preferable, because the quality of the image is made high. An emulsion having a narrow grain size distribution, as described in U.S. Pat. No. 4,775,617, is also preferable. It is preferable to restrict the shape of tabular grains so that the thickness of the grains may be 0.5 microns or below, and more preferably 0.3 microns or below, because the sharpness is increased. Further, an emulsion in which the grains are highly uniform in thickness, with the deviation coefficient of grain thickness being 30% or below, is also preferable. Grains in which the thickness of the grains and the plane distance between twin planes are defined, as described in JP-A No. 163451/1988, are also preferable.

In the case of tabular grains, the dislocation lines can be observed by a transmission electron microscope. In accordance with the purpose, it is preferable to choose grains having no dislocation lines, grains having several dislocation lines, or grains having many dislocation lines. Dislocation introduced straight in a special direction in the crystal orientation of grains, or curved dislocation, can be chosen, and it is possible to choose from, for example, dislocation introduced throughout grains, dislocation introduced in a particular part of grains, and dislocation introduced limitedly to the fringes of grains. In addition to the case of introduction of dislocation lines into tabular grains, also preferable is the case of introduction of dislocation lines into regular crystalline grains or irregular grains, represented by potato grains. In this case, a preferable mode is that introduction is limited to a particular part of grains, such as vertexes and edges.

The silver halide emulsion used in the present invention may be subjected to a treatment for making grains round, as disclosed, for example, in European Patent No. 96,412B1, or it may be improved in the surface, as disclosed in West Germany Patent No. 2,306,447C2 and JP-A No. 221320/1985.

Generally, the grain surface has a flat structure, but it is also preferable in some cases to make the grain surface uneven intentionally. Examples are a technique in which part of crystals, for example, vertexes and the centers of planes, are formed with holes, as described in JP-A Nos. 106532/1983 and 221320/1985, and ruffled grains, as described in U.S. Pat. No. 4,643,966.

The grain size of the emulsion used in the present invention is evaluated, for example, by the diameter of the projected area equivalent to a circle using an electron microscope; by the diameter of the grain volume equivalent to a sphere, calculated from the projected area and the grain thickness; or by the diameter of a volume equivalent to a sphere, using the Coulter Counter method. A selection can be made from ultrafine grains having a sphere-equivalent diameter of 0.05 microns or below, and coarse grains having a sphere-equivalent diameter of 10 microns or more. Preferably grains of 0.1 microns or more but 3 microns or below are used as photosensitive silver halide grains.

As the emulsion used in the present invention, an emulsion having a wide grain size distribution, that is, a so-called polydisperse emulsion, or an emulsion having a narrow grain size distribution, that is, a so-called monodisperse emulsion, can be chosen and used in accordance with the purpose. As the scale for representing the size distribution, the diameter of the projected area of the grain equivalent to a circle, or the deviation coefficient of the sphere-equivalent diameters, is used. If a monodisperse emulsion is used, it is good to use an emulsion having such a size distribution that the deviation coefficient is 25% or below, more preferably 20% or below, and further more preferably 15% or below.

In some cases, a monodisperse emulsion is defined by the average grain size distribution based on the weight or number of grains. Further, in order to allow the photographic material to satisfy the intended gradation, in an emulsion layer having substantially the same color sensitivity, two or more monodisperse silver halide emulsions different in grain size are mixed and applied to the same layer or are applied as overlaid layers. Further, two or more polydisperse silver halide emulsions can be used as a mixture; or they can be used to form overlaid layers; or a combination of a monodisperse emulsion and a polydisperse emulsion can be used as a mixture; or the combination can be used to form overlaid layers.

As an emulsion used in the present invention, use can be made of an emulsion containing the above grains. One mode of carrying out the present invention is that the color-developing agent of the present invention and the emulsion comprising tabular grains whose silver chloride content is 50 mol % or more, are not used in combination.

As the photographic emulsion used in the present invention, any silver halide emulsion prepared by a method described, for example, by P. Glafkides in "Chemie et Phisique Photographique," Paul Montel, 1967; by G. F. Duffin in "Photographic Emulsion Chemistry," Focal Press, 1966; or by V. L. Zelikman et al. in "Making and Coating Photographic Emulsion," Focal Press, 1964, can be used. That is, any of the acid process, the neutral process, the ammonia process, and the like can be used; and to react a soluble silver salt with a soluble halogen salt, any of the single-jet method, the double-jet method, a combination thereof, and the like can be used. A method wherein grains are formed in the presence of excess silver ions (the so-called reverse precipitation process) can also be used. As one type of the double-jet method, a method wherein pAg in the liquid phase, in which a silver halide will be formed, is kept constant, that is, the so-called controlled double-jet method, can also be used. According to this method, a silver halide emulsion wherein the crystals are regular in shape and whose grain size is approximately uniform, can be obtained.

A method in which previously precipitated silver halide grains are added to a reaction vessel for the preparation of an emulsion, and the methods described, for example, in U.S. Pat. Nos. 4,334,012, 4,301,241, and 4,150,994, are preferable in some cases. These can be used as seed crystals, or they are effective when they are supplied as a silver halide for growth. In the latter case, it is preferable to add an emulsion whose grains are small in size, and as an addition method, one of the following can be chosen: all of the volume is added at one stroke, or the volume is separated and added in portions, or it is added continuously. Further, in some cases, it is also effective to add grains having different halogen compositions in order to modify the surface.

The method in which a large part or only a small part of the halogen composition of silver halide grains is converted by the halogen conversion method is disclosed, for example, in U.S. Pat. Nos. 3,477,852 and 4,142,900, European Patent Nos. 273,429 and 273,430, and West German Publication Patent No. 3,819,241, and it is an effective method for forming grains. To convert to a more hardly soluble silver salt, it is possible to add a solution of a soluble halogen or to add silver halide grains. Selection can be made from respective methods in which the conversion is made at one stroke, in several steps, and continuously.

In addition to the method in which the grain growth is made by adding a soluble silver salt and a halogen salt at constant concentrations and at constant flow rates, grain formation methods wherein the concentration is changed or the flow rate is changed, as described in British Patent No. 1,469,480 and U.S. Pat. Nos. 3,650,757 and 4,242,445, are preferable methods. By changing the concentration or increasing the flow rate, the amount of the silver halide to be supplied can be changed as a linear function, a quadratic function, or a more complex function, of the addition time. Further, if required, the amount of the silver halide to be supplied is decreased, which is preferable in some cases. Also effective is an addition method wherein, when several soluble silver salts different in solution composition are added, or when several soluble halogen salts different in solution composition are added, one of them is increased and the other is decreased.

A mixing vessel that is used when a solution of a soluble silver salt and a solution of a soluble halogen salt are reacted can be selected for use from methods described in U.S. Pat. Nos. 2,996,287, 3,342,605, 3,415,650, and 3,785,777, and West German Publication Patent Nos. 2,556,885 and 2,555,364.

For the purpose of promoting the ripening, a silver halide solvent is useful. For example, it is known to allow an excess amount of halide ions to be present in the reaction vessel, to promote the ripening. Further, other ripening agent can be used. All of the amount of these ripening agents may be blended in the dispersion medium in the reaction vessel before silver and halide salts are added, or their introduction into the reaction vessel may be carried out together with the addition of a halide, a silver salt, or a peptitizer. As another modified mode, a method is possible wherein a ripening agent is added independently at the step of adding a halide salt and a silver salt.

For example, ammonia, thiocyanates (e.g. potassium rhodanate and ammonium rhodanate), organic thioether compounds (e.g. compounds described, for example, in U.S. Pat. Nos. 3,574,628, 3,021,215, 3,057,724, 3,038,805, 4,276,374, 4,297,439, 3,704,130, and 4,782,013, and JP-A No. 104926/1982), thion compounds (e.g. tetra-substituted thioureas described, for example, in JP-A Nos. 82408/1978 and 77737/1980, and U.S. Pat. No. 4,221,863; and compounds described in JP-A No. 144319/1978), mercapto compounds capable of promoting the growth of silver halide grains, as described in JP-A No. 202531/1982, and amine compounds (e.g. described in JP-A No. 100717/1979), can be mentioned.

As a protective colloid and as a binder of other hydrophilic colloid layers that are used when the emulsion according to the present invention is prepared, gelatin is used advantageously, but another hydrophilic colloid can also be used.

Use can be made of, for example, a gelatin derivative, a graft polymer of gelatin with another polymer, a protein, such as albumin and casein; a cellulose derivative, such as hydroxycellulose, carboxymethylcellulose, and cellulose sulfate; sodium alginate, a starch derivative, acacia, a saccharide derivative of a natural compound, such as a polysaccharide, including dextran and pullulan; and many synthetic hydrophilic polymers, including homopolymers and copolymers, such as a polyvinyl alcohol, a polyvinyl alcohol partial acetal, a poly-N-vinylpyrrolidone, a polyacrylic acid, a polymethacrylic acid, a polyacrylamide, a polyvinylimidazole, and a polyvinylpyrazole. Further, use can be made of a high-water-absorptive polymer described, for example, in U.S. Pat. No. 4,960,681 and JP-A No. 245,260/1987, that is, a copolymer of a vinyl monomer having —COOM or —$SO_3M$ (wherein M represents a hydrogen atom or an alkali metal), or a copolymer of these vinyl monomers, or a copolymer of this vinyl monomer with another vinyl monomer (e.g. sodium methacrylate, ammonium methacrylate, and Sumikagel L-5H [trade name; manufactured by Sumitomo Chemical Co., Ltd.]). Two or more of these binders can be used in combination. A combination of gelatin with these binders is also preferable.

As the gelatin, one of lime-processed gelatin, acid-processed gelatin, and so-called de-ashed gelatin wherein the content of calcium or the like is reduced, can be selected, or a combination of them is also preferable. Enzyme-processed gelatin described in Bull. Soc. Sci. Photo. Japan, No. 16, page 30 (1966), may also be used, and a hydrolyzate or enzymolyzate of gelatin can also be used. For the preparation of tabular grains, it is preferable to use a low-molecular-weight gelatin described in JP-A No. 158426/1989.

In the case of a heat-processable photographic material, an organic silver salt oxidizing agent may be used together with a photosensitive silver halide emulsion, and, as organic compounds capable of being used to form it, there are benzotriazoles described in U.S. Pat. No. 4,500,626, columns 52 to 53, aliphatic acids, and other compounds. An acetylene silver described in U.S. Pat. No. 4,775,613 is also useful. It is possible to use the organic silver salts in the form of a combination of two or more.

These organic silver salts are used in an amount of 0.01 to 10 mol, and preferably 0.01 to 1 mol, per mol of the photosensitive silver halide. The total coating amount of the photosensitive silver halide emulsion and the organic silver salt is suitably 0.05 to 10 $g/m^2$, and more preferably 0.1 to 4 $g/m^2$, in terms of silver.

Preferably, the emulsion according to the present invention is washed with water for desalting and is dispersed in a freshly prepared protective colloid. The temperature at which the washing with water is carried out can be selected in accordance with the purpose, and preferably the temperature is selected in the range of 5° to 20° C. The pH at which the washing is carried out can be selected in accordance with the purpose, and preferably the pH is selected in the range of 2 to 10, and more preferably in the range of 3 to 8. The pAg at which the washing is carried out can be selected in accordance with the purpose, and preferably the pAg is selected in the range of 5 to 10. As a method of washing with water, one can be selected from the noodle washing method, the dialysis method using a diaphragm, the centrifugation method, the coagulation settling method, and the ion exchange method. In the case of the coagulation settling method, selection can be made from, for example, the method wherein sulfuric acid is used, the method wherein an organic solvent is used, the method wherein a water-soluble polymer is used, and the method wherein a gelatin derivative is used.

When the emulsion according to the present invention is prepared, in accordance with the purpose, it is preferable to allow a salt of a metal ion to be present, for example, at the time when grains are formed, in the step of desalting, at the time when the chemical sensitization is carried out, or before the application. When the grains are doped, the addition is preferably carried out at the time when the grains are formed; or after the formation of the grains, when the surface of the grains is modified or when the salt of a metal ion is used as a chemical sensitizer; or before the completion of the chemical sensitization. As to the doping of grains, selection can be made from a case in which the whole grains are doped, one in which only the core parts of the grains are doped, one in which only the shell parts of the grains are doped, one in which only the epitaxial parts of the grains are doped, and one in which only the substrate grains are doped. For example, Mg, Ca, Sr, Ba, Al, Sc, Y, La, Cr, Mn, Fe, Co, Ni, Cu, Zn, Ga, Ru, Rh, Pd, Re, Os, Ir, Pt, Au, Cd, Hg, Tl, In, Sn, Pb, and Bi can be used. These metals can be added if they are in the form of a salt that is soluble at the time when grains are formed, such as an ammonium salt, an acetate, a nitrate, a sulfate, a phosphate, a hydroxide, a six-coordinate complex, and a four-coordinate complex. Examples include $CdBr_2$, $CdCl_2$, $Cd(NO_3)_2$, $Pd(NO_3)_2$, $Pb(CH_3COO)_2$, $K_3[Fe(CN)_6]$, $(NH_4)_4[Fe(CN)_6]$, $K_3IrCl_6$, $(NH_4)_3RhCl_6$, and $K_4Ru(CN)_6$. As a ligand of the coordination compound, one can be selected from halo, aquo, cyano, cyanate, thiocyanate, nitrosyl, thionitrosyl, oxo, and carbonyl. With respect to these metal compounds, only one can be used, but two or more can also be used in combination.

In some cases, a method wherein a chalcogen compound is added during the preparation of the emulsion, as described in U.S. Pat. No. 3,772,031, is also useful. In addition to S, Se, and Te, a cyanate, a thiocyanate, a selenocyanate, a carbonate, a phosphate, or an acetate may be present.

The silver halide grains according to the present invention can be subjected to at least one of sulfur sensitization, selenium sensitization, tellurium sensitization (these three are called chalcogen sensitization, collectively), noble metal sensitization, and reduction sensitization, in any step of the production for the silver halide emulsion. A combination of two or more sensitizations is preferable. Various types of emulsions can be produced, depending on the steps in which the chemical sensitization is carried out. There are a type wherein chemical sensitizing nuclei are embedded in grains, a type wherein chemical sensitizing nuclei are embedded at parts near the surface of grains, and a type wherein chemical sensitizing nuclei are formed on the surface. In the emulsion according to the present invention, the location at which chemical sensitizing nuclei are situated can be selected in accordance with the purpose, and generally preferably at least one type of chemical sensitizing nucleus is formed near the surface.

Chemical sensitizations that can be carried out preferably in the present invention are chalcogen sensitization and noble metal sensitization, which may be used singly or in combination; and the chemical sensitization can be carried out by using active gelatin as described by T. H. James in "The Photographic Process," 4th edition, Macmillan, 1997, pages 67 to 76, or by using sulfur, selenium, tellurium, gold, platinum, palladium, or iridium, or a combination of these sensitizing agents, at a pAg of 5 to 10, a pH of 5 to 8, and a temperature of 30° to 80° C., as described in Research Disclosure, Item 12008 (April 1974); Research Disclosure, Item 13452 (June 1975); Research Disclosure, Item 307105 (November 1989); U.S. Pat. Nos. 2,642,361, 3,297,446, 3,772,031, 3,857,711, 3,901,714, 4,266,018, and 3,904,415, and British Patent No. 1,315,755.

In the sulfur sensitization, an unstable sulfur compound is used, and specifically, thiosulfates (e.g. hypo), thioureas (e.g. diphenylthiourea, triethylthiourea, and allylthiourea), rhodanines, mercaptos, thioamides, thiohydantoins, 4-oxooxazolidin-2-thions, di- or polysulfides, polythionic acids, and elemental sulfur, and known sulfur-containing compounds described in U.S. Pat. Nos. 3,857,711, 4,266,018, and 4,054,457, can be used. In many cases, sulfur sensitization is used in combination with noble metal sensitization.

A preferable amount of a sulfur sensitizing agent used for the silver halide grains according to the present invention is $1\times10^{-7}$ to $1\times10^{-3}$ mol, and more preferably $5\times10^{-7}$ to $1\times10^{-4}$ mol, per mol of the silver halide.

In the selenium sensitization, known unstable selenium compounds are used, such as those described, for example, in U.S. Pat. Nos. 3,297,446 and 3,297,447, specific such selenium compounds are colloidal metal selenium, selenoureas (e.g. N,N-dimethylselenourea and tetramethylselenourea), selenoketones (e.g. selenoacetone), selenoainides (e.g. selenoacetamide), selenocarboxylic acids and esters, isoselenocyanates, selenides (e.g. diethylselenides and triphenylphosphine selenide), and selenophosphates (e.g. tri-p-tolylselenophosphate). In some cases, preferably the selenium sensitization is used in combination with one or both of sulfur sensitization and noble metal sensitization.

The amount of the selenium sensitizing agent to be used varies depending on the selenium compound, the silver halide grains, the chemical ripening conditions, and the like that are used, and the amount is generally of the order of $10^{-8}$ to $10^{-4}$ mol, and preferably $10^{-7}$ to $10^{-5}$ mol, per mol of the silver halide.

As the tellurium sensitizing agent used in the present invention, compounds described in Canadian Patent No. 800,958, British Patent Nos. 1,295,462 and 1,396,696, and JP-A Nos. 333819/1990 and 131598/1991 can be used, and specific tellurium sensitizing agents include colloidal tellurium, telluroureas (e.g. tetramethyltellurourea, N-carboxylethyl-N',N'-dimethyltellurourea, and N,N'-dimethylethylenetellurourea), isotellurocyanates, telluroketones, telluroimides, tellurohydrazides, telluroesters, phosphine tellurides (e.g. tributylphosphine telluride and butylisopropylphosphine telluride), and other tellurium compounds (e.g. potassium tellurocyanate and sodium telluropentathionate).

The amount of the tellurium sensitizing agent to be used is of the order of $10^{-7}$ to $5\times10^{-2}$ mol, and more preferably $5\times10^{-7}\times10^{-3}$ mol, per mol of the silver halide.

In the noble metal sensitization, a salt of a noble metal, such as platinum, gold, palladium, and iridium, can be used, and specifically gold sensitization, palladium sensitization, and a combination thereof are particularly preferable. In the case of gold sensitization, a known compound, such as chloroauric acid, potassium chloroaurate, potassium auriothiocyanate, gold sulfide, and gold selenide, can be used. The palladium compound means salts of divalent or tetravalent palladium salt. A preferable palladium compound is represented by $R_2PdX_6$ or $R_2PdX_4$, wherein R represents a hydrogen atom, an alkali metal atom, or an ammonium radical; and X represents a halogen atom, i.e. a chlorine atom, a bromine atom, or an iodine atom.

Specifically, $K_2PdCl_4$, $(NH_4)_2PdCl_6$, $NaPdCl_4$, $(NH_4)_2PdCl_4$, $Li_2PdCl_4$, $Na_2PdCl_6$, or $K_2PdBr_4$ is preferable. Preferably a gold compound and a palladium compound are used in combination with a thiocyanate or a selenocyanate.

Preferably the emulsion according to the present invention is used in combination with gold sensitization. A preferable amount of the gold sensitizing agent is $1\times10^{-7}$ to $1\times10^{-3}$ mol, and more preferably $5\times10^{-7}$ to $5\times10^{-4}$ mol, per mol of the silver halide. A preferable amount of the palladium compound is in the range of $5\times10^{-7}$ to $1\times10^{-3}$ mol. A preferable amount of the thiocyan compound and the selenocyan compound is in the range of $1\times10^{-6}$ to $5\times10^{-2}$ mol.

Preferably that the silver halide emulsion according to the present invention is subjected to reduction sensitization during the formation of the grains, after the formation of the grains but before the chemical sensitization, or during or after the chemical sensitization.

Herein, the reduction sensitization can be selected from a method wherein a reduction sensitizer is added to a silver halide emulsion; a method called silver ripening, wherein the growth or ripening is made in an atmosphere having a pAg as low as 1 to 7; and a method called high-pH ripening, wherein the growth or ripening is made in an atmosphere having a pH as high as 8 to 11. Two or more methods can also be used in combination.

The method wherein a reduction sensitizer is added is preferable, because the level of reduction sensitization can be adjusted subtly.

As the reduction sensitizer, known reduction sensitizers can be selected and used, such as stannous salts, ascorbic acid and its derivatives, amines and polyamines, hydrazine and its derivatives, formamidinesufinic acid, silane compounds, and boran compounds; and two or more compounds can be used in combination. As the reduction sensitizer, preferable compounds are stannous chloride, aminoiminomethanesulfinic acid (popularly called thiourea dioxide), dimethylaminoboran, and ascorbic acid and its derivatives. Since the amount of the reduction sensitizer to be added depends on the conditions of the production of the emulsion, the amount must be selected, but suitably it is in the range of $10^{-7}$ to $10^{-3}$ mol per mol of the silver halide.

The chemical sensitization can be carried out in the presence of a so-called chemical sensitization auxiliary. As a useful chemical sensitization auxiliary, a compound is used that is known to suppress fogging and to increase the sensitivity in the process of chemical sensitization, such as azaindene, azapyridazine, and azapyrimidine. Examples of chemical sensitization auxiliary improvers are described in U.S. Pat. Nos. 2,131,038, 3,411,914, and 3,554,757, JP-A No. 126526/1983, and by G. F. Duffin in "Photographic Emulsion Chemistry" mentioned above, pages 138 to 143.

Preferably an oxidizing agent for silver is added during the process of the production of the emulsion according to the present invention. The oxidizing agent for silver refers to a compound that acts on metal silver to convert it to silver ions. Particularly useful is a compound that converts quite fine silver grains, which are concomitantly produced during the formation of silver halide grains and during the chemical sensitization, to silver ions. The thus produced silver ions may form a silver salt that is hardly soluble in water, such as a silver halide, silver sulfide, and silver selenide, or they may form a silver salt that is readily soluble in water, such as silver nitrate. The oxidizing agent for silver may be inorganic or organic. Example inorganic oxidizing agents include ozone, hydrogen peroxide and its adducts (e.g. $NaBO_2 \cdot H_2O_2 \cdot H_2O$, $2NaCO_3 \cdot H_2O_2$, $Na_4P_2O_7 \cdot H_2O_2$, and $2NaSO_4 \cdot H_2O_2 \cdot 2H_2O$); oxygen acid salts, such as peroxyacid salts (e.g. $K_2S_2O_8$, $K_2C_2O_6$, and $K_2P_2O_8$), peroxycomplex compounds (e.g. $K_2[Ti(O_2)C_2O_4] \cdot 3H_2O$, $4K_2SO_4 \cdot Ti(O_2)OH \cdot SO_4 \cdot 2H_2O$, and $Na_3[VO(O_2)(C_2O_4)_2] \cdot 6H_2O$), permanganates (e.g. $KMnO_4$), and chromates (e.g. $K_2CrO_7$); halogen elements, such as iodine and bromine; perhalates (e.g. potassium periodate), salts of metals having higher valences (e.g. potassium hexacyanoferrate(III), and thiosulfonates.

Examples of the organic oxidizing agents include quinones, such as p-quinone; organic peroxides, such as peracetic acid and perbenzoic acid; and compounds that can release active halogen (e.g. N-bromosuccinimido, chloramine T, and chloramine B).

Preferable oxidizing agents used in the present invention are such inorganic oxidizing agents as ozone, hydrogen peroxide and its adducts, halogen elements, and thiosulfonates, and such organic oxidizing agents as quinones. Use of a combination of the above reduction sensitization with the oxidizing agent for silver is a preferable mode. Use is made of one selected from a method wherein after an oxidizing agent is used, reduction sensitization is carried out; a method wherein after reduction sensitization is carried out, an oxidizing agent is used; and a method wherein an oxidizing agent and a reduction sensitizer are present simultaneously. These methods can be used in the step of forming grains or in the step of chemical sensitization, which step will be chosen.

In the photographic emulsion used in the present invention, various compounds can be incorporated for the purpose of preventing fogging during the process of the production of the photographic material, during the storage of the photographic material, or during the photographic processing, or for the purpose of stabilizing the photographic performance. That is, compounds known as antifoggants or stabilizers can be added, such as thiazoles including benzothiazolium salts, nitroimidazoles, nitrobonzimidazoles, chlorobenzimidazoles, bromobenzimidazoles, mercaptothiazoles, mercaptobenzothiazoles, mercaptobenzimidazoles, mercaptothiadiazoles, aminotriazoles, benzotrtazoles, nitrobenzotriazoles, mercaptotetrazoles (particularly 1-phenyl-5-mercaptotetrazole), mercaptopyrimidine, mercaptotriazine; thioketo compounds, such as oxazolinthione; and azaindenes, such as triazaindenes; tetraazaindenes (particularly 4-hydroxy-6-methyl-1,3,3a,7-tetraazaindenes), and pentaazaindenes. For examples, those described in U.S. Pat. Nos. 3,954,474 and 3,982,947, and JP-B No. 28660/1987, can be used. A preferable compound is a compound described in Japanese Patent Application No. 47225/1987. In accordance with the purpose, the antifoggant and the stabilizer can be added at various times, for example, before the formation of the grains, during the formation of the grains, after the formation of the grains, in the step of washing with water, at the time of dispersion after the washing with water, before the chemical sensitization, during the chemical sensitization, after the chemical sensitization, and before the application. In addition to the case wherein the antifoggant and the stabilizer are added during the preparation of the emulsion, so that the antifogging effect and the stabilizing effect, which are their essential effects, may be achieved, they can be used for various other purposes, for example, for controlling the habit of the crystals, for making the grain size small, for reducing the solubility of the grains, for controlling the chemical sensitization, and for controlling the arrangement of the dyes.

When the photosensitive silver halide used in the present invention is made to have color sensitivities of green sensitivity, red sensitivity, and infrared sensitivity, the photosensitive silver halide emulsion is spectrally sensitized with methine dyes or the like. If required, the blue-sensitive emulsion may be spectrally sensitized in the blue region.

Dyes that can be used include a cyanine dye, a merocyanine dye, a composite cyanin dye, a composite merocyanine dye, a halopolar cyanine dye, a hemicyanine dye, a styryl dye, and a hemioxonol dye. Particularly useful dyes are those belonging to a cyanine dye, a merocyanine dye, and a composite merocyanine dye. In these dyes, any of nuclei generally used in cyanine dyes as base heterocyclic ring nuclei can be applied. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, and a pyridine nucleus; and a nucleus formed by fusing an cyctoaliphatic hydrocarbon ring or an aromatic hydrocarbon ring to these nuclei, that is, 5- to 64-hydroxy-6-methyl-hetnrocyclic ring nuclei, such as an indolenine nucleus, a benzindolenine nucleus, an indole nucleus, a benzoxazole nucleus, a naphthooxazole nucleus, a benzothiazole nucleus, a naphthothiazole nucleus, a benzoselenazole nucleus, a benzimidazole nucleus, a rhodanine nucleus, and a thiobarbituric acid nucleus, can be applied. These nuclei may be substituted on the carbon atom. Specifically, sensitizing dyes described, for example, in U.S. Pat. No. 4,617,257 and JP-A Nos. 180, 550/1984, 13,546/1989, 45,828/1993, and 45,834/1983 can be mentioned.

In the merocyanine dye or the composite merocyanine dye, as a nucleus having a ketomethylene structure, a 5- to 6-membered heterocyclic ring nucleus, such as a pyrazolin-5-one nucleus, a thiohydantoine nucleus, a 2-thiooxazolidin-2,4-dione nucleus, a thiazolidin-2,4-dione nucleus, a rhodanine nucleus, and a thiobarbituric acid nucleus, can be applied.

These dyes can be used singly or in combination, and a combination of these sensitizing dyes is often used, particularly for the purpose of adjusting the wavelength of the spectral sensitivity, and for the purpose of supersensitization. Typical examples thereof are described in U.S. Pat. Nos. 2,688,545, 3,397,060, 2,977,229, 3,522,052, 3,527,64, 3,617,293, 3,628,964, 3,672,898, 3,679,428, 3,703,377, 3,769,301, 3,814,609, 3,837,862, and 4,026,707. British Patent Nos. 1,344,281 and 1,507,803, JP-B Nos. 4,936/1968 and 12,375/1978, and JP-A Nos. 110,618/1977 and 109,925/1977.

Together with the sensitizing dye, a dye having no spectral sensitizing action itself, or a compound that does not substantially absorb visible light and that exhibits supersensitization, may be included in the emulsion (e.g. those described, for example, in U.S. Pat. No. 3,615,641 and JP-A No. 23,145/1988).

The time when these sensitizing dyes are added to the emulsion may be at any stage of the preparation of the emulsion that is known to be useful.

Most usually, the sensitizing dye is added at a time after the completion of chemical sensitization but before the application, but the sensitizing dye may be added at the same time is the addition of the chemical sensitizing dye, to carry out spectral sensitization and chemical sensitization simultaneously, as described in U.S. Pat. Nos. 3,628,969 and 4,225,666, or the sensitizing dye may be added before the chemical sensitization, as described in JP-A No. 113,928/1983. Further, the sensitizing dye may be added before the completion of the precipitation of the silver halide grains, to start the spectral sensitization. Further, the sensitizing dye may be added before or after the formation of nuclei of the silver halide grains, in accordance with U.S. Pat. Nos. 4,183,756 and 4,225,666, or it may be added in portions, such that part of the sensitizing dye is added before the chemical sensitization, and the rest is added after the chemical sensitization.

Further, these sensitizing dyes and supersensitizing dyes may be added in the form of a solution of an organic solvent, such as methanol, or in the form of a dispersion of gelatin, or in the form of a solution of a surface-active agent.

Generally the amount of the sensitizing dye to be added is of the order of $4\times10^{-6}$ to $8\times10^{-3}$ mol per mol of the silver halide, but when the silver halide grain size is 0.2 to 1.2 μm, which is more preferable, the amount of the sensitizing dye to be added is more effectively about $5\times10^{-5}$ to $2\times10^{-3}$ mol per mol of the silver halide.

To the photographic material related to the present technique, may be added the above-mentioned various additives, and also other various additives in accordance with the purpose.

These additives are described in more detail in Research Disclosure, Item 17643 (December 1978); Research Disclosure, Item 18176 (November 1979); and Research Disclosure, Item 307105 (November 1989), and the particular parts are given below in a Table.

| Additives | RD 17643 | RD 18716 | RD 307105 |
|---|---|---|---|
| 1. Chemical Sensitizer | p. 23 | p. 648, right column | p. 996 |
| 2. Sensitivity Increasing Agent | | p. 648, right column | |
| 3. Spectral Sensitizer, Supersensitizer | pp. 23–24 | p. 648, right column to p. 649, right column | pp. 996–998 |
| 4. Brightening Agent | p. 24 | p. 647, right column | p. 998 |
| 5. Light Absorber, Filter Dye, Ultraviolet ray Absorber | pp. 25–26 | p. 649, right column to p. 650, left column | p. 1003 |
| 6. Binder | p. 26 | p. 651, | pp. 1003–1004 |
| 7. Plasticizer, Lubricant | pp. 27 | p. 650, | p. 1006 |
| 8. Coating Aid, Surface Active Agent | pp. 26–27 | p. 650, | p. 1005, left column to p. 1006, right column |
| 9. Antistatic Agent | p. 27 | p. 650 right column | pp. 1006–1007 |
| 10. Antifoggant and Stabilizer | pp. 24–25 | p. 649 | pp. 998–1000 |
| 11. Antistaining Agent | p. 25 right column | p. 650 right to left column | |
| 12. Dye image stabilizer | p. 25 | | |
| 13. Hardener | p. 26 | p. 651 left column | p. 1004 right colum to p. 1005 left column |

In addition to the above hardeners, other hardeners are described, for example, in U.S. Pat. No. 4,678,739, 41st column; U.S. Pat. No. 4,791,042, and JP-A Nos. 116,655/1984, 245,261/1987, 18,942/1986, and 218,044/1992. More specifically, aldehyde hardeners (e.g. formaldehyde), aziridine hardeners, epoxy hardeners, vinyl sulfone hardeners (e.g. N,N'-ethylene-bis(vinylsulfonylacetamide)ethane), N-methylol hardeners (e.g. dimethylol urea), or polymer hardeners (e.g. compounds described, for example, in JP-A No. 234,157/1987) can be mentioned.

These hardeners are used in an amount of 0.001 to 1 g, and preferably 0.005 to 0.5 g, per g of the coated gelatin. The layer into which the hardeners are added may be any of layers that constitute the photographic material or the dye-fixed material, or the hardener may be divided into two or more parts, which are added into two or more layers.

In the photographic material of the present invention, a matting agent can be used for the purpose of adhesion prevention, improvement of slipping property, matting, etc. Example matting agents include silicon dioxide, polyolefins, polymethacrylates, and the like described in JP-A No. 88,256/1986, page 29, as well as compounds, including benzoguanamine resin beads, polycarbonate resin beads, ABS resin beads, and the like, described in JP-A Nos. 274,944/1988 and 274,952/1988. Other matting agents described in the above RD can be used. These matting agents are added into the uppermost layer (protective layer), and also into a lower layer if required.

Further, the constitutional layers of a heat-processable photographic material may contain a heat solvent, an antifoaming agent, a germ-proofing agent, a mildew-proofing agent, colloidal silica, etc. Specific examples of these additives are described, for example, in JP-A No. 88,256/1986, pages 26 to 32; JP-A NO. 11,338/1991, and JP-B No. 51-51,496/1990.

In the constitutional layers of the photographic material of the present invention, use can be made of various surface-active agents for various purposes of, for example, serving as a coating aid, improving releasability and slipping property, preventing electrification, or promoting development. Specific examples of the surface-active agents are described, for example, in the above Research Disclosures and JP-A Nos. 173,463/1987 and 183,457/1987. In the case of a heat-processable photographic material, also preferably an organofluoro compound is contained in the constitutional layer, for example, for the purposes of improving slipping properties, preventing electrification, and improving releasability. Typical examples of the organofluoro compound are hydrophobic fluoro compounds, including solid fluoro compound resins, such as ethylene tetrafluoride resins; oily fluoro compounds, including fluoro oils; or fluorine-containing surface-active agents described, for example, in JP-B No. 9,053/1982, 8th column to the 17th column, and JP-A Nos. 20,944/1986 and 135,836/1987.

In the photographic material of the present invention, known antifading agents can be used. Example organic antifading agents include hydroquinones, 5-hydroxychromans, 5-hydroxycoumarans, paraalkoxyphenols, hindered phenols, including bisphenols; gallic acid derivatives, methylenedioxybenzenes, aminophenols, hindered amines, and ether or ester derivatives produced by silylating or alkylating the phenolic hydroxyl group of these compounds. Further, metal complexes, represented by (bissalicylaldoximato)nickel complex and (bis-N,N-dialyldithiocarbamato)nickel complex, can also be used.

To prevent a yellow dye image from being deteriorated by heat, humidity, and light, the addition of a compound having both the structures of a hindered amine and a hindered phenol in the same molecule, as described in U.S. Pat. No. 4,268,593, gives a good result. Further, to prevent a magenta dye image from being deteriorated particularly by light, spiroindanes described in JP-A No. 159,644/1981, and chromans substituted with a hydroquinone diether or monoether, described in JP-A No. 89,835/1980, give a good result.

In the constitutional layers of the photographic material of the present invention, various antifoggants or photographic stabilizers and their precursors can be used. Specific examples thereof are compounds described, for example, in the above-mentioned Research Disclosures, U.S. Pat. Nos. 5,089,378, 4,500,627, and 4,614,702, JP-A No. 13,546/1989 (pages 7 to 9, 57 to 71, and 81 to 97), U.S. Pat. Nos. 4,775,610, 4,626,500, and 4,983,494, JP-A Nos. 174,747/1987, 239,148/1987, 264,747/1988, 150,135/1989, 110,557/1990, and 178,650/1990, and Research Disclosure No. 17,643 (1978), pages 24 to 25.

These compounds are preferably used in an amount of $5 \times 10^{-6}$ to $1 \times 10^{-1}$ mol, and more preferably $1 \times 10^{-5}$ to $1 \times 10^{-2}$ mol, per mol of silver.

Suitable bases that can be used in the present invention include a synthetic plastic film, for example, made of polyolefins, such as polyethylenes and polypropylenes, polycarbonates, cellulose acetates, polyethylene terephthalates, polyethylene naphthalates, and polyvinyl chlorides; a paper base, for example, made of photographic base paper, printing paper, baryta paper, and resin-coated paper; a base formed by providing the above plastic film with a reflective layer; and a base described in JP-A No. 253,159/1987, pages 29 to 31.

Those described in the above Research Disclosure No. 17643, page 28; Research Disclosure No. 18716, page 647, right column, to page 648, left column; and Research Disclosure No. 307105, page 879, are preferably used. These bases may be subjected to heat treatment at or below Tg, as described in U.S. Pat. No. 4,141,735, so that they may be hardly core-set. The surface of the bases may be surface-treated, to improve the adhesion between the base and the emulsion undercoat layer. In the present invention, the surface treatment can be carried out by glow discharge treatment, ultraviolet-ray-irradiation treatment, corona treatment, or flame treatment.

Further, bases described in Kochi Gijutsu No. 5 (published by Azutekku Yugen-kaisha, Mar. 22, 1991), pages 44 to 149, can also be used.

Transparent bases made, for example, of polyethylenedinaphthalene dicarboxylates, and bases produced by coating these transparent bases with a transparent magnetic product, can also be used.

In a heat-processable photographic material, in order to obtain a constant image all the time against changes in the processing temperature and the processing time at the time of development, various development arrestors can be used. Herein, the term "a development arrestor" means a compound that neutralizes bases quickly or reacts quickly with bases after suitable development, to lower the base concentration in the film, to stop the development; or a compound that interacts with silver and silver salts, to inhibit the development. Specific examples include acid precursors that release an acid when heated, electrophilic compounds that undergo a substitution reaction with coexisting bases when heated, nitrogen-containing heterocyclic compounds, mercapto compounds, and their precursors. Details are described in JP-A No. 253,159/1987, pages 31 to 32.

When the photographic material of the present invention is used as a heat-processable photographic material, to supply a base, a method wherein a base is generated from a base precursor, is preferable.

Preferable base precursors used in the present invention include a salt of a base with an organic acid that is decarboxylated when heated; a compound that is decomposed by such a reaction as an intramolecular nucleophilic substitution reaction, Lossen rearrangement, or Beckmann rearrangement, to release amines; a compound that undergoes some reaction when heated, to release a base; and a compound that undergoes hydrolysis or a complex formation reaction, to generate a base. Examples of the above base precursor that generates a base when heated include bases of trichloroacetic acid described, for example, in British Patent No. 998,959; bases of α-sulfonylacetic acid that are further improved in stability, as described in U.S. Pat. No. 4,060,420; bases of propiolic acid described in Japanese Patent Application No. 55,700/1983; 2-carboxycarbodiamide derivatives described in U.S. Pat. No. 4,088,496; salts of heat-decomposable acids that are formed using, in addition to an organic base, an alkali metal or an alkali earth metal (Japanese Patent Application No. 69,597/1983); hydroxamcarbamates that use Lossen rearrangement, as described in Japanese Patent Application No. 43,860/1983; and aldoximecarbamates that produce nitrite when heated, as described in Japanese Patent Application No. 31,614/1983.

Also useful are base precursors described, for example, in British Patent Nos. 998,945 and 2,079,480, JP-A No. 226,225/1975, U.S. Pat. Nos. 3,220,846, 4,514,493, and 4,657,848, and Kochi Gijutsu No. 5 (published by Azutekku Yugen-kaisha, Mar. 22, 1991), pages 55 to 86.

Examples methods of exposing the photographic material of the present invention with light and recording the image, include a method wherein a landscape, a man, or the like is directly photographed by a camera or the like; a method wherein a reversal film or a negative film is exposed to light using, for example, a printer, or an enlarging apparatus; a method wherein an original picture is subjected to scanning exposure through a slit by using an exposure system of a copying machine or the like; a method wherein light-emitting diodes and various lasers (e.g. laser diodes and gas lasers) are allowed to emit light, to carry out scanning exposure through image information and electrical signals (methods described, for example, in JP-A No. 129,625/1990 and Japanese Patent Application Nos. 338,182/1991, 9,388/1992, and 281,442/1992); and a method wherein image information is outputted to an image display apparatus, such as a CRT, a liquid crystal display, an electroluminescence display, and a plasma display, and exposure is carried out directly or through an optical system.

Light sources that can be used for recording an image on the photographic material, as mentioned above, include natural light and light sources and exposure methods described in U.S. Pat. No. 4,500,626, 56th column, and JP-A Nos. 53,378/1990 and 54,672/1990, such as a tungsten lamp, a light-emitting diode, a laser light source, and a CRT light source.

Image-wise exposure can be carried out by using a wavelength-converting element that uses a nonlinear optical material and a coherent light source, such as laser rays, in combination. Herein the term "nonlinear optical material" refers to a material that can develop nonlinearity of the electric field and the polarization that appears when subjected to a strong photoelectric field, such as laser rays, and inorganic compounds, represented by lithium niobate, potassium dihydrogenphosphate (KDP), lithium iodate, and $BaB_2O_4$; urea derivatives, nitroaniline derivatives, nitropyridine-N-oxide derivatives, such as 3-methyl-4-nitropyridine-N-oxide (POM); and compounds described in JP-A Nos. 53,462/1986 and 210,432/1987 can be preferably used. As the form of the wavelength-converting element, for example, a single crystal optical waveguide type and a fiber type are known, both of which are useful.

The above image information can employ, for example, image signals obtained from video cameras, electronic still cameras, and the like; television signals, represented by Nippon Television Singo Kikaku (NTSC); image signals obtained by dividing an original picture into a number of picture elements by a scanner or the like; and an image produced by a computer, represented by CG or CAD.

The color-developing agent of the present invention can be used for all silver halide photographic materials, including color negatives, color papers, X-ray photographic materials and reproduction photographic materials for color instant photography and color reversal, and X-ray photographic materials and reproduction photographic materials for forming color images. Further, the color-developing agent of the present invention can be added into a silver halide photographic material, and also into a processing solution.

If the color-developing agent of the present invention is added into a silver halide photographic material, the development can be carried out by heating treatment or activator treatment.

The heating treatment of photographic materials is known in the art, and heat-processable photographic materials and the process thereof are described, for example, in "Shashin Kogaku no Kiso" (published by Corona-sha, 1979), pages 553 to 555; "Eizo Joho" (published April 1978), page 40; "Nebletts Handbook of Photography and Reprography," 7th edition (Van Nostrand and Reinhold Company), pages 32 to 33; U.S. Pat. Nos. 3,152,904, 3,301,678, 3,392,020, and 3,457,075, British Patent Nos. 1,131,108 and 1,167,777, and Research Disclosure (June 1978), pages 9 to 15 (RD-17029).

The activator treatment refers to a treatment wherein a color development agent is built in a photographic material and the photographic material is developed with a processing solution free from any color-developing agent. In this case, the processing solution is characterized in that it does not contain a color-developing agent, which is normally contained as a development processing solution component, but the processing solution may contain other components (e.g. an alkali and an auxiliary developing agent). Examples of the activator treatment are shown in known publications, such as European Patent Nos. 545,491A1 and 565,165A1.

In the present invention, the term "a developing solution" means a processing solution containing a color-developing agent and a processing solution not containing a developing agent (for activator).

Processing materials and processing methods used in the case of the activator treatment in the present invention will now be described in detail. In the present invention, the photographic material is developed (silver development/cross oxidation of the built-in color developing agent), desilvered, washed with water, and stabilized. In some cases, after the washing with water or the stabilizing processing, a treatment of alkalinization for color formation intensification (alkali treatment) is carried out.

When the photographic material of the present invention is developed with a developing solution, preferably the developing solution contains a compound that serves as a developing agent of silver halides and/or allows the developing agent oxidation product resulting from the silver development to cross-oxidize the color-developing agent built in the photographic material (auxiliary developing agent). Preferably, pyrazolidones, dihydroxybenzenes, reductones, and aminophenols are used, and particularly preferably pyrazolidones are used.

Among pyrazolidones, 1-phenyl-3-pyrazolidones are preferable, and they include 1-phenyl-3-pyrazolidone, 1-phenyl-4,4-dimethyl-3-pyrazolidone, 1-phenyl-4-methyl-4-hydroxylmethyl-3-pyrazolidone, 1-phenyl-4,4-dihydroxydimethyl-3-pyrazolidone, 1-phenyl-5-methyl-3-pyrazolidone, 1-phenyl-5-phenyl-3-pyrazolidone, 1-p-tolyl-4-methyl-4-hydroxymethyl-3-pyrazolidone, 1-p-chlorophenyl-4-methyl-4-hydroxymethyl-3-pyrazolidone, 1-phenyl-2-hydroxymethyl-4,4-dimethyl-3-pyrazolidone, 1-phenyl-2-acetyl-3-pyrazolidone, 1-phenyl-2-hydroxymethyl-5-phenyl-3-pyrazolidone, and 1-(2-chlorophenyl)-4-hydroxymethyl-4-methyl-3-pyrazolidone.

Dihydroxybenzenes include hydroquinone, chlorohydroquinone, bromohydroquinone, isopropylhydroquinone, methylhydroquinone, 2,3-dichlorohydroquinone, 2,5-dichlorohydroquinone, 2,5-dimethylhydroquinone, and potassium hydroquinonemonosulfonate.

Reductones include N-methyl-p-aminophenol, N-(β-hydroxyethyl)-p-aminophenol, N(4-hydroxyphenyl)glycine, and 2-methyl-p-aminophenol.

Although these compounds are generally used singly, use of two or more of them in combination is also preferable, to enhance the development and cross oxidation activity.

The amount of these compounds to be used in the developing solution is $2.5 \times 10^{-4}$ to 0.2 mol/liter, preferably 0.0025 to 0.1 mol/liter, and more preferably 0.001 to 0.05 mol/liter.

Example preservatives for use in the developing solution according to the present invention include sodium sulfite, potassium sulfite, lithium sulfite, formaldehyde sodium bisulfite, and hydroxylamine.sulfate, which are preferably used in an amount in the range of 0.1 mol/liter or below, and more preferably 0.001 to 0.02 mol/liter. If a high-silver-chloride emulsion is used in the photographic material, the above compound is used in an amount of 0.001 mol/liter or below, and preferably it is not used at all in some cases.

In the present invention, instead of the above hydroxylamine or sulfite ions, an organic preservative can be preferably used.

Herein the term "organic preservatives" refers generally to organic compounds that reduce the deteriotation speed of the above developing agent when added to the developing solution. That is, organic preservatives are organic compounds that have a function of preventing developing agents from being oxidized with air or the like; and particularly effective organic preservatives are other hydroxylamine derivatives (excluding hydroxylamine), hydroxamic acids, hydrazines, phenols, α-hydroxyketones, α-aminoketones, saccharides, monoamines, diamines, polyamines, quaternary ammoniums, nitroxy radicals, alcohols, oximes, diamide compounds, and fused-ring-type amines. These are described, for example, in JP-A Nos. 4235/1988, 5341/1988, 30845/1988, 21647/1988, 44655/1988, 46454/1988, 53551/1988, 43140/1988, 56654/1988, 58346/1988, 43138/1988, 146041/1988, 44657/1988, and 44656/1988, U.S. Pat. Nos. 3,615,503 and 2,494,903, and JP-B No. 30496/1973. Further, other reservatives that may be contained, if required, include, for example, various metals described in JP-A Nos. 44148/1982 and 53749/1982, salicylic acids described in JP-A No. 180588/1984, alkanolamines described in JP-A No. 3532/1979, polyethyleneamines described in JP-A No. 94349/1981, and aromatic polyhydroxy compounds described in U.S. Pat. No. 3,746,544. In particular, preferably contained are alkanolamines described in JP-A No. 97355/1992, pages 631 to 632, and dialkylhydroxylamines described therein, pages 627 to 630. Further, it is also preferable to use a combination of dialkylhydroxylamines and/or hydrazine derivatives with alkanolamines, or a combination of α-amino acids, represented by glycine, with dialkylhydroxylamines, as described in European Patent No. 530,921A1.

These compounds are preferably used in an amount of $1 \times 10^{-3}$ to $5 \times 10^{-1}$ mol, and more preferably $1 \times 10^{-2}$ to $2 \times 10^{-1}$ mol, per liter of the developing solution.

In the present invention, the developing solution contains halide ions, such as chloride ions, bromide ions, and iodide ions. Preferably, when a high silver-chloride emulsion is used, chloride ions are contained in an amount of $3.5 \times 10^{-3}$ to $3.0 \times 10^{-1}$ mol/liter, and more preferably $1 \times 10^{-2}$ to $2 \times 10^{-1}$ mol/liter, and/or bromide ions in an amount of $0.5 \times 10^{-5}$ to $1.0 \times 10^{-3}$ mol/liter, and more preferably $3.0 \times 10^{-5}$ to $5 \times 10^{-4}$ mol/liter.

Herein the halide ions may be added directly to the developing solution, or they may be dissolved out from the photographic material into the developing solution during the development processing.

If the halide ions are added to the developing solution, the halide ion source may be a sodium salt, a potassium salt, an ammonium salt, a lithium salt, or a magnesium salt, of the halide ion.

When the halide ions are dissolved out from the photographic material, the halide ions are supplied mainly from the silver halide emulsion, but they may also be supplied from some other source.

The developing solution used in the present invention preferably has a pH of 8 to 13, and more preferably 9 to 12.

To retain the above pH, it is preferable to use various buffers, examples of which are carbonates, phosphates, brorates, tetraborates, hydroxybenzoates, glycinates, N,N-dimethylglycinates, leucinates, norleucinates, guaninates, 3,4-dihydroxyphenylalaninates, alaninates, aminobutylates, 2-amino-2-methyl-1,3-propandiol salts, valerates, prolinates, trishydroxylaminomethane salts, and lysinates. In particular, carbonates, phosphates, tetraborates, and hydroxybenzoates are excellent in solubility and buffering function at a pH in the range of 9.0 or over, and when they are added to the developing solution, the photographic performance is not adversely affected, so that they are preferably used.

Specific examples of these buffers are lithium carbonate, sodium carbonate, potassium carbonate, potassium bicarbonate, tripotassium phosphate, trisodium phosphate, dipotassium phosphate, disodium phosphate, potassium borate, sodium borate, sodium tetraborate, potassium tetraborate, sodium o-hydroxybenzoate (sodium salicylate), and potassium 5-sulfo-2-hydroxybenzoate (potassium 5-sulfosalicylate).

The amount of the buffers to be added to the developing solution is preferably 0.05 mol/liter or over, and particularly preferably 0.1 to 0.4 mol/liter.

In addition, in the developing solution, as a sediment-preventive agent against calcium and magnesium, or as an agent for stabilizing the developing solution, various chelating agents can be used. Examples are nitrilotriacetic acid, diethylenetriaminepentaacetic acid, ethylenediaminetetraacetic acid, N,N,N-trimethylenephosphonic acid, ethylenediamine-N,N,N',N'-tetramethylenesulfonic acid, 1,2-diaminopropanetetraacetic acid, glycol ether diaminetetraacetic acid, ethylenediamine orthohydroxyphenylacetic acid, 2-phosphonobutane-1,2,4-tricarboxylic acid, 1-hydroxyethylidene-1,1-diphosphonic acid, and 1,2-dihydroxybenzene-4,6-disulfonic acid, and their alkali metal salts. Two or more of these chelating agents may be used in combination, if necessary.

With respect to the amount of these chelating agents to be added, preferably the amount is enough to sequester the metal ions in the developing solution, and, for example, these chelating agents are used in an amount in the order of 0.1 to 10 g per liter.

In the present invention, if required, an arbitrary antifoggant can be added. As the antifoggant, nitrogen-containing heterocyclic compounds, and alkali metal halide, such as sodium chloride, potassium bromide, and potassium iodide, are used. Typical examples of the nitrogen-containing heterocyclic compounds are benzotriazole, 5-nitrobenzotriazole, 5-methylbenzotriazole, 5-nitrobenzimidazole, 5-nitroindazole, 2-thiazolylbenzimidazole, indazole, hydroxyazaindolizine, adenine, and 1-phenyl-5-mercaptotetrazole, or their derivatives.

The amount of the nitrogen-containing heterocyclic compounds to be added is $1 \times 10^{-5}$ to $1 \times 10^{-2}$ mol/liter, and preferably $2.5 \times 10^{-5}$ to $1 \times 10^{-3}$ mol/liter.

In the developing solution, if necessary, an arbitrary development accelerator can be added, examples of which are the following compounds: thioether compounds described, for example, in JP-B Nos. 16088/1962, 5987/1962, 7826/1963, 12380/1969, and 9019/1970, and U.S. Pat. No. 3,813,247; p-phenylenediamine compounds described in JP-A Nos. 49829/1977 and 15554/1975; quaternary ammonium salts described, for example, in JP-A No. 137726/1975, JP-B No. 30074/1969, and JP-A Nos. 156826/1981 and 43429/1977; amine compounds described, for example, in U.S. Pat. Nos. 2,494,903, 3,128,182, 4,230,796, and 3,253,919, JP-B No. 11431/1966, and U.S. Pat. Nos. 2,482,546, 2,596,926, and 3,582,346; and imidazoles and polyalkylene oxides described, for example, in JP-B Nos. 16088/1962 and 25201/1967 and U.S. Pat. No. 3,532,501.

Preferably the developing solution contains a fluorescent whitening agent. In particular, it is preferable to use 4,4-diamino-2,2'-disulfostilbene-type compounds. Specifically, commercially available fluorescent whitening agents, such as compounds described, for example, in "Senshoku Note," 19th edition, pages 165 to 168, and compounds described in JP-A No. 242943/1992, pages 3 to 7, can be used. The amount to be added is 0.1 to 10 g/liter, and preferably 0.5 to 5 g/liter.

The processing temperature of the developing solution to be applied to the present invention is 20° to 50° C., and preferably 30° to 45° C. The processing time is 5 sec to 2 min, and preferably 10 sec to 1 min. With respect to the replenishing rate, although a small amount is preferable, the replenishing rate is 15 to 600 ml, preferably 25 to 200 ml, and more preferably 35 to 100 ml, per m² of the photographic material.

The photographic material of the present invention may be in a form having an electro-conductive heat-generating element layer, which serves as a heating means for heat processing. In this case, as the heat-generating element, those described, for example, in JP-A No. 145,544/1986 can be employed.

The heating temperature in the heat development step is generally about 65° to 180° C., preferably 70° to 180° C., more preferably 75° to 180° C., further more preferably 80° to 150° C., and particularly preferably 80° to 135° C. The heating time is preferably 0.1° to 120° C., more preferably 0.1 to 60 sec, and particulary preferably 0.1 to 30 sec.

Example heating methods in the development step include one wherein the photographic material is brought in contact with a heated block or plate; a method wherein the photographic material is brought in contact with a hot plate, a hot presser, a hot roller, a hot drum, a halogen lamp heater, an infrared lamp heater, or a far-infrared lamp heater; and a method wherein the photographic material is passed through a high-temperature atmosphere. As a method wherein the heat-processable photographic material and a dye-fixing material are placed one upon the other, methods described in JP-A Nos. 253,159/1987 and 147,244/1986 (page 27) can be applied.

After the development, a desilvering process can be carried out. The desilvering process comprises a fixing process, or both bleaching process and a fixing process. When both bleaching and fixing are carried out, the bleaching process and the fixing process may be carried out separately or simultaneously (bleach-fixing process). Also, according to the purpose, the processing may be carried out in a bleach-fixing bath having two successive tanks; or the fixing process may be carried out before the bleach-fixing process; or the bleach-fixing may be carried out after the bleach-fixing process.

In some cases, it is preferable to carry out the stabilizing process, to stabilize silver salts and dye images, without carrying out the desilvering process after the development.

Example bleaching agents for use in the bleaching solution or the bleach-fix solution include, for example, compounds of polyvalent metals, such as iron(III), cobalt(III), cromium(IV), and copper(II); peracids; qunones; and nitro compounds. Typical compounds are iron chloride, ferricyanides, dichromates, organic complex salts of iron (III) (e.g. metal salts of ethylenediaminetetraacetic acid, diethylenetriaminepentaacetic acid, cyclohexanediaminetetraacetic acid, 1,3-diaminopropanetetraacetic acid, methylimiodiacetic acid; and aminopolycarboxylic acids and their salts, as described in JP-A No. 365036/1992, pages 5 to 17), persulfates, permanganates, bromates, hydrogen peroxide and compounds releasing thereof (e.g. percarbonic acid and perboric acid), and nitrobenzenes. Among them, ethylenediaminetetraacetatic acid iron(III) complex salts, aminopolycarboxylic acid iron(III) of 1,3-diaminopropanetetraacetate iron(III) complex salts, hydrogen peroxide, persulfates, and the like are preferred, in view of rapid processing and the prevention of enviromental pollution. The bleaching solution and bleach-fix solution that use these aminopolycarboxylic acid irons(III) are used at a pH of 3 to 8, and preferably 5 to 7. The bleaching solution that uses persulfates and hydrogen peroxide is used at a pH of 4 to 11, and preferably 5 to 10.

In the bleaching solution, the bleach-fix solution, and the bath preceding them, if required, a bleach-accelerating agent can be used. Specific examples of useful bleach-accelerating agents include compounds having a mercapto group or a disulfide bond, as as described, for example, in U.S. Pat. No. 3,893,856, West German Patent No. 1,290,812, JP-A No. 95630/1978, and Research Disclosure No. 17129 (July 1978); thiazolidine derivatives described in JP-A No. 140129/1975; thiourea derivatives described in U.S. Pat. No. 3,706,561; iodide salts described in JP-A No. 16235/1983; polyoxyethylene compounds described in West Germany Patent No. 2,748,430; and iodide ions and polyamine compounds described in JP-B No. 9936/1970.

Above all, compounds having a mercapto group or a disulfide group are preferable, because they are high in accelerating effect. When color photographic materials for photography are desilvered, these bleach-accelerating agents are particularly effective.

With respect to the accelerating agent for persulfate bleaching, complex salts of 2,6-pyridinedicarboxylic acid or 2-pyridinecarboxylic acid with iron (III) ion, as described in JP-A No. 214365/1994 (European Patent No. 0602600A1), are effective. With respect to the accelerating agent for hydrogen peroxide bleaching, metal salts of organic acids, described in JP-B Nos. 16067/1986 and 19024/1986, are effective.

In the bleaching solution, the bleach-fix solution, and the fixing solution, use can be made of known additives, such as a rehalogenating agent, including ammonium bromide and ammonium chloride; a pH buffering agent, including ammonium nitrate, acetic acid, boric acid, citric acid or its salt, tartaric acid or its salt, succinic acid or its salt, and imidazole; and a metal corrosion-preventive agent, including ammonium sulfate. In particular, it is preferable to contain an organic acid, to prevent bleach stain. The organic acid is a compound having an acid dissociation constant (pKa) of 2 to 7, and specifically acetic acid, succinic acid, citric acid, and propionic acid are preferable.

Example fixing angents for use in the fixing solution and the bleach-fix solution include thiosulfates, thiocyanates, thioureas, a large amount of iodide salts, and thioether compounds, metho-ionic compounds, and nitrogen-containing heterocyclic compounds, having a sulfide group, as described in JP-A No. 365037/1992, pages 11 to 21, and JP-A No. 66540/1993, pages 1088 to 1092. Among these, use of thiosulfates is usual, and ammonium thiosulfate is most widely used. A combination of thiosulfates with thiocyanates, thioether compounds, thiourea, or metho-ionic compounds, is also preferable.

Preferable preservatives for the fixing solution and the bleach-fix solution are sulfites, bisulfites, carbonylbisulfite adducts, and sulfinic acid compounds described in European Patent No. 294769A. In the fixing solution, the bleaching solution, and the bleach-fix solution, to stabilize the solutions, it is preferable to add any of various aminopolycarboxylic acids, organic phosphonic acids (e.g. 1-hydroxyethylidene-1,1-diphosphonic acid, N,N,N',N'-ethylenediaminetetraphosphonic acid, and 2-phosphonobutane-1,2,4-tricarboxylic acid) and sodium stannate.

In the fixing solution and the bleach-fix solution, further, for example, any of various fluorescent whitening agents, antifoaming agents, surface-active agents, polyvinylpyrolidones, and methanol can be contained.

The processing temperature of the desilvering step is 20° to 50° C., and preferably 30° to 45° C. The processing time is 5 sec to 2 min, and preferably 5 sec to 1 min. Although a small replenishing rate is preferable, the replenishing rate is 15 to 600 ml, preferably 25 to 200 ml, and more preferably 35 to 100 ml, per $m^2$ of the photographic material. The processing is also preferably carried out without replenishment in such a way that the evaporated amount is supplemented with water.

The photographic material of the present invention is generally passed through a washing (rinsing) step after the desilvering process. If a stabilizing process is carried out, the washing step can be omitted. In such a stabilizing process, processes described in JP-A Nos. 8543/1982, 14834/1983, and 220345/1985, and all known processes described in JP-A Nos. 127926/1983, 137837/1983, and 140741/1983, can be used. A washing-stabilizing process, in which a stabilizing bath containing a dye stabilizer and a surface-active agent typically used for the processing of color photographic materials for photographing is used as a final bath, can be carried out.

In the washing liquid and stabilizing solution, use can be made of a water softener, such as sulfites, inorganic phosphoric acids, polyaminocarboxylic acids, and organic aminophosphoric acids; a metal salt, such as Mg salts, Al salts, and Bi salts; a surface-active agent, a hardener, a pH buffer, a fluorescent whitening agent, and a silver-salt-forming agent, such as nitrogen-containing heterocyclic compounds.

Example dye-stabilizing agents of the stabilizing solution include, for example, aldehydes, such as formaldehyde and glutaraldehyde; N-methylol compounds, hexamethylenetetramine, or aldehyde sulfite adducts.

The pH of the washing liquid and the stabilizing solution is 4 to 9, and preferably 5 to 8. The processing temperature is 15° to 45° C., and preferably 25° to 40°. The processing time is 5 sec to 2 min, and preferably 5 sec to 40 sec.

The overflow liquid associated with the replenishment of the above washing liquid and/or the stabilizing solution, can be reused in other processes, such as the desilvering process.

The amount of the washing liquid and/or the stabilizing solution can be set in a wide range depending on various conditions, and the replenishing rate is preferably 15 to 360 ml, and more preferably 25 to 120 ml, per $m^2$ of the photographic material. To reduce the replenishing rate, it is preferable to use multiple tanks and a multi-stage counter-current system. In particular, it to is preferable to use 2 to 5 tanks. In order to prevent the propagation of bacteria and adhesion stain of suspended matter on the photographic material that will result from reduction in the amount of these solutions, use can be made of bactericides, such as sodium chlorinated isocynurate, cyapentazoles, and isothiazolone compounds described in JP-A No. 8542/1982; other benzotriazoles; and bactericides described by Hiroshi Horiguchi in "Bokin-bobaizai no Kagaku" (1986, Sankyoshuppan); in "Biseibutsu no Mekkin, Sakkin, Bobai Gijutsu," edited by Eisei Bobai-gakkai (1982, Kogyo Gijutsu-kai); and in "Bokin Babai-zai Jiten," edited by Nihon Bokin Bobai-gakkai (1986). Further, a method of reducing Mg and Ca ions, as described in JP-A No. 288838/1987, is particularly preferably used.

In the present invention, in order to save water, water can be used that has been obtained by treating the overflow liquid or the in-tank liquid using a reverse osmosis membrane. For example, the treatment by reverse osmosis is preferably carried out for water from the second tank, or the more latter tank of the multi-stage countercurrent washing process and/or the stabilizing process. Specifically, in the case of a two-tank system, the water in the second tank is treated by a reverse osmosis membrane, and in the case of a four-tank system, the water in the third lank and the fourth tank is treated by a reverse osmosis membrane, and then the passed water is returned to the first tank (the tank from which water for the reverse osmosis treatment has been taken) or is brought to a washing tank and/or a stabilizing tank situated downstream. It is also one mode that the concentrated liquid is returned to a tank situated upstream of that particular tank and further to the desilvering bath.

As the material of the reverse osmosis membrane, for example, cellulose acetates, crosslinked polyamides, polyethers, polysulfons, polyacrylic acids, and polyvinylene carbonates can be used. The pressure of the pumped liquid used for these membranes is preferably 2 to 10 kg/cm² and particularly preferably 3 to 7 kg/cm².

In the present invention, preferably the stirring is intensified as much as possible. To intensify the stirring, specifically a method wherein a jet stream of a processing liquid is caused to impinge on the emulsion surface of a photographic material, as described in JP-A Nos. 183460/1987 and 183461/1987; a method wherein a rotating means is used to increase the stirring effect, as described in JP-A No. 183461/1987; a method wherein a photographic material is moved, with the emulsion surface of the material being in contact with a wiper blade provided in a liquid, so that a turbulent flow may occur near the emulsion surface, to improve the stirring effect; and a method wherein the total amount of a processing solution to be circulated is increased, can be mentioned. These means of improving the stirring are useful in any of the developing solution, the bleaching solution, the bleach-fix solution, the stabilizing solution, and the washing liquid. These methods are effective in that the effective constituents in the solution are supplied to the photographic material and the diffusion of unnecessary components in the photographic material is promoted.

In the present invention, any state of the liquid opening rate |contact area of air (cm²)/liquid volume (cm³)| of any of the baths can exhibit excellent performance, but in view of the stability of the liquid components, preferably the liquid opening rate is 0 to 1.0 $cm^{-1}$. In the continuous processing, from a practical point of view, the liquid opening rate is preferably 0.001 to 0.05 $cm^{-1}$, and more preferably 0.002 to 0.03 $cm^{-1}$.

The automatic developing machine used for the photographic material of the present invention is preferably provided with a means of transporting a photographic material, as described in JP-A No. 191257/1985, 191258/1985, and 191259/1985. Such a transporting means can reduce remarkably the carry-in of the processing solution from a preceding bath to a succeeding bath. Therefore it is high in the effect of preventing the performance of a processing solution from being deteriorated. Such an effect is effective in shortening the processing time of each process and in reducing the process replenishing rate. To shorten the processing time, it is preferable to shorten the crossover time (the aerial time), and a method wherein a photographic material is transported between processes through a blade having a screening effect, as described, for example, in JP-A No. 86659/1992, FIG. 4, 5, or 6, and JP-A No. 66540/1993, FIG. 4 or 5, is preferable.

Further, if each of the processing solutions in the continuous process is concentrated due to evaporated, preferably water is added to compensate for the evaporation.

The processing time in each process according to the present invention means the time required from the start of the processing of the photographic material at any process, to the start of the processing in the next process. The actual processing time in an automatic developing machine is determined generally by the linear speed and the volume of the processing bath, and in the present invention, as the linear speed, 500 to 4,000 mm/min can be mentioned as a guide. Particularly in the case of a small-sized developing machine, 500 to 2,500 mm/min is preferable.

The processing time in the whole processing steps, that is, the processing time from the developing process to the drying process, is preferably 360 sec or below, more preferably 120 sec or below, and particularly preferably 90 to 30 sec. Herein the processing time means the time from the dipping of the photographic material into the developing solution, till the emergence from the drying part of the processor.

By using the compounds according to the present invention, even when two-equivalent couplers are used, images good in color-forming property can be obtained.

EXAMPLES

The present invention will now be described specifically with reference to the Examples, but of course the present invention is not limited to them.

Example 1

A surface of a paper base, both surfaces of which had been laminated with a polyethylene, was subjected to corona discharge treatment; then it was provided with a gelatin undercoat layer containing sodium dodecylbenzensulfonate, and it was coated with two photographic constitutional layers, to produce a photographic printing paper (100) having the two-layer constitution shown below. The coating liquids were prepared as follows.

(First-Layer Coating Liquid)

22.4 g of a coupler (C-22), 16.8 g of a color-developing agent (EXCD-1), and 80 g of a solvent (Solv-1) were dissolved in ethyl acetate, and the resulting solution was emulsified and dispersed into a 16% gelatin solution containing 10% sodium dodecylbenzensulfonate and citric acid, to prepare an emulsified dispersion A.

On the other hand, a silver chlorobromide emulsion A (cubes, a mixture of a large-size emulsion having an average grain size of 0.88 μm, and a small-size emulsion having an average grain size of 0.70 μm (3:7 in terms of mol of silver), the deviation coefficients of the grain size distributions being 0.08 and 0.10 respectively, and each emulsion having 0.3 mol % of silver bromide locally contained in part of the grain surface whose substrate was made up of silver chloride) was prepared. To the large-size emulsion of this emulsion, had been added $1.4 \times 10^{-4}$ mol, per mol of silver, of each of blue-sensitive sensitizing dyes A, B, and C shown below, and to the small-size emulsion of this emulsion, had been added $1.7 \times 10^{-4}$ mol, per mol of silver, of each of blue-sensitive sensitizing dyes A, B, and C shown below. The chemical ripening of this emulsion was carried out with a sulfur sensitizer and a gold sensitizer being added. The above emulsified dispersion A and this silver chlorobromide emulsion A were mixed and dissolved, and a first-layer coating liquid was prepared so that it would have the composition shown below. The coating amount of the emulsion is in terms of silver.

The coating liquid for the second layer was prepared in the similar way as that for the first-layer coating liquid. As the gelatin hardener for each layer, 1-oxy-3,5-dichloro-s-triazine sodium salt was used.

Further, to each layer, were added Cpd-2, Cpd-3, Cpd-4, and Cpd-5, so that the total amounts would be 15.0 mg/m$^2$, 60.01 mg/m$^2$, 50.0 mg/m$^2$, and 10.0 mg/m$^2$, respectively.

For the silver chlorobromide emulsion of the first layer, the following spectral sensitizing dye was used.

Sensitizing dye A

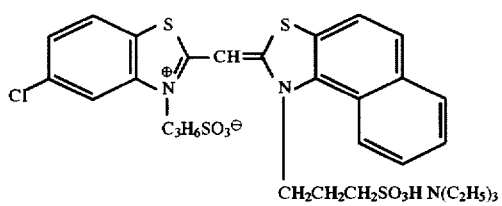

Sensitizing dye B

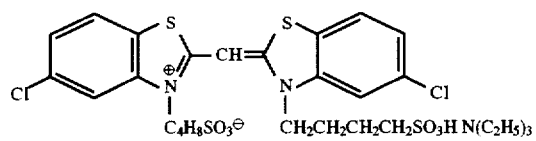

Sensitizing dye C

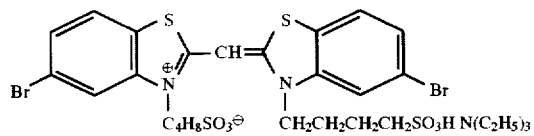

(Layer Constitution)

The composition of each layer is shown below. The numbers show coating amounts (g/m$^2$). In the case of the silver halide emulsion, the coating amount is in terms of silver.

Base

Polyethylene-Laminated Paper

[The polyethylene on the first layer side contained a white pigment (TiO$_2$) and a blue dye (ultramarine)]

| First Layer | |
|---|---|
| The above silver chlorobromide emulsion A | 0.20 |
| Gelatin | 1.50 |
| Yellow coupler (C-21) | 0.22 |
| Color developing agent (EXCD-1) | 0.17 |
| Solvent (Solv-1) | 0.80 |
| Second Layer (protective layer) | |
| Gelatin | 1.01 |
| Acryl-modified copolymer of polyvinyl alcohol (modification degree: 17%) | 0.04 |
| Liquid paraffin | 0.02 |
| Surface-active agent (Cpd-1) | 0.01 |

The procedure for preparing Sample (100) was repeated, except that the coupler and the color-developing agent in the coating liquid of the first layer were changed to the couplers and the color-developing agents, in the same molar amounts, shown in Table 1, thereby preparing Samples (101) to (120).

Further, the procedure for preparing Sample (100) was repeated, except that, in the coating liquid of the first layer, the silver chlorobromide emulsion A was changed to the following silver chlorobromide emulsion B, in the same amount of silver, and the coupler and the color-developing agent were changed to the couplers and the color-developing agents, in the same molar amounts, shown in Table 2, thereby preparing Samples (200) to (220). Further, as the dispersion medium, Solve-2 was used.

A silver chlorobromide emulsion B: cubes, a mixture of a large-size emulsion having an average grain size of 0.55 μm, and a small-size emulsion having an average grain size of 0.39 μm (1:3 in terms of mol of silver). The deviation coefficients of the grain size distributions were 0.10 and 0.08, respectively, and each emulsion had 0.8 mol % of AgBr locally contained in part of the grain surface whose substrate was made up of silver chloride.

For the silver chlorobromide emulsion B, the following spectrally sensitizing dyes were used:

Sensitizing dye D

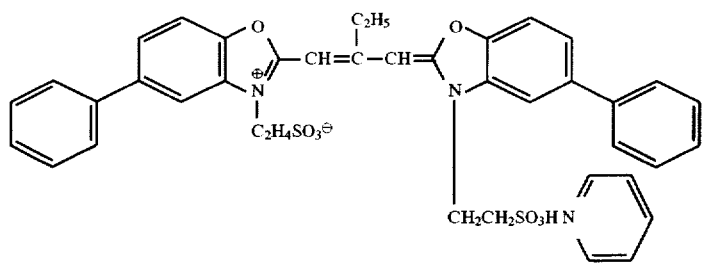

Sensitizing dye E

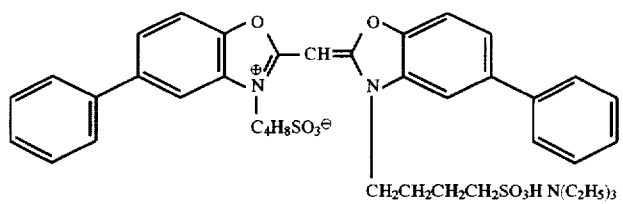

Sensitizing dye F

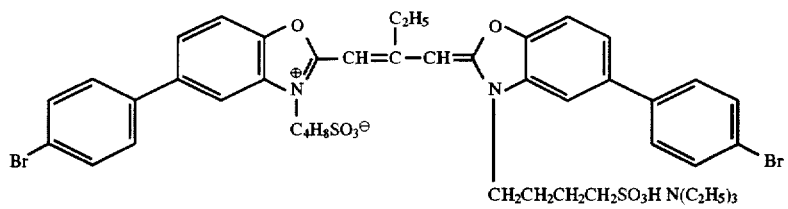

The sensitizing dye D was added to the large-size emulsion in an amount of $3.0 \times 10^{-4}$ mol per mol of the silver halide, and to the small-size emulsion in an amount of $3.6 \times 10^{-4}$ mol per mol of the silver halide; the sensitizing dye E was added to the large-size emulsion in an amount of $4.0 \times 10^{-5}$ mol per mol of the silver halide, and to the small-size emulsion in an amount of $7.0 \times 10^{-5}$ mol per mol of the silver halide; and the sensitizing dye F was added to the large-size emulsion in an amount of $2.0 \times 10^{-4}$ mol per mol of the silver halide, and to the small-size emulsion in an amount of $2.8 \times 10^{-5}$ mol per mol of the silver halide.

Further, the procedure for preparing Sample (100) was repeated, except that, in the coating liquid of the first layer, the silver chlorobromide emulsion A was changed to the following silver chlorobromide emulsion C, in the same amount of silver, and the coupler and the color-developing agent were changed to the couplers and the color-developing agents, in the same molar amounts, shown in Table 3, thereby preparing Samples (300) to (320).

A silver chlorobromide emulsion C: cubes, a mixture of a large-size emulsion having an average grain size of 0.5 μm, and a small-size emulsion having an average grain size of 0.41 μm (1:4 in terms of mol of silver). The deviation coefficients of the grain size distributions were 0.09 and 0.11, respectively, and each emulsion had 0.8 mol % of AgBr locally contained in part of the grain surface whose substrate was made up of silver chloride.

For the silver chlorobromide C, the following spectrally sensitizing dyes were used:

Sensitizing dye G

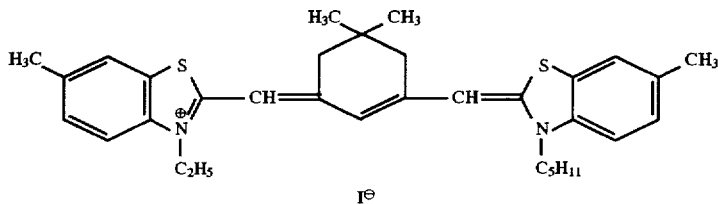

Sensitizing dye H
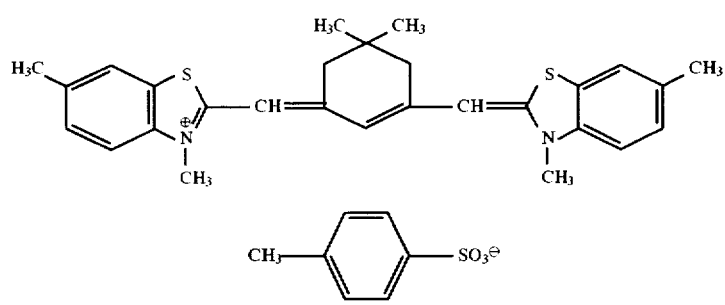
(Each was added to the large-size emulsion in an amount of $5.0\times10^{-5}$ mol per mol of the silver halide, and to the small-size emulsion in an amount of $8.0\times10^{-5}$ per mol of the silver halide.)
(EXCD-1)
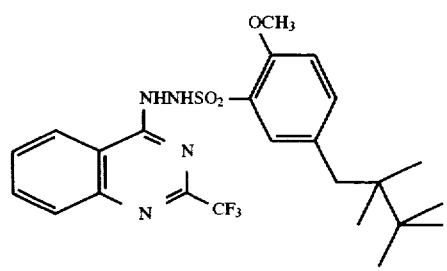
(Compound described in EP Patent No. 545491A1)
(C-21)
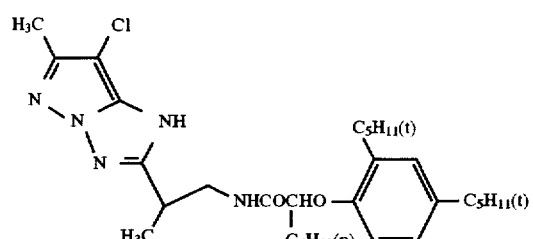
(C-40)
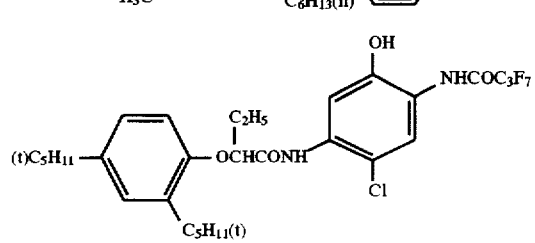
(C-47)
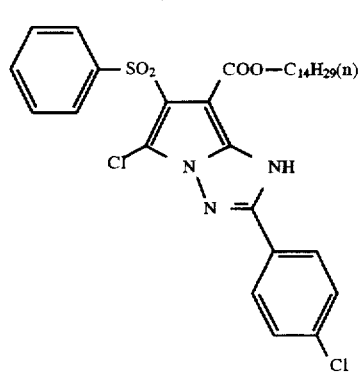
(C-43)
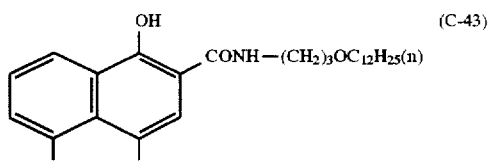
(C-41)
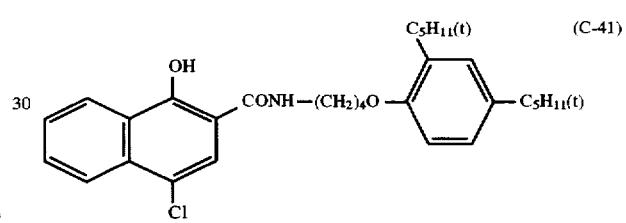
(C-2)
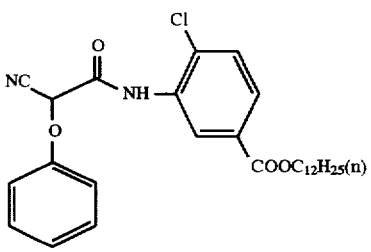
(C-77)
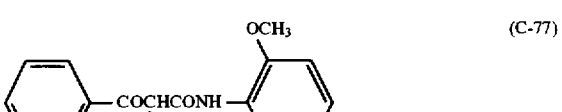
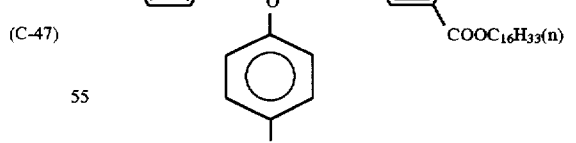

-continued (C-27)

Surface-active agent (Cpd-1)

7:3 mixture (by weight ratio) of

CH₂COOCH₂CHC₄H₉ with C₂H₅
NaO₃S—CHCOOCH₂CHC₄H₉ with C₂H₅ and

C₁₃H₂₇CONH(CH₂)₃—N⁺(CH₃)₂—CH₂COO⁻

Antiseptic (Cpd-2)

Antiseptic (Cpd-3)

Antiseptic (Cpd-4)

-continued

1:1:1:1 mixture of a, b, c, d

| | R₁ | R₂ |
|---|---|---|
| a | —Me | —NHMe |
| b | —Me | —NH₂ |
| c | —H | —NH₂ |
| d | —H | —NHMe |

Antiseptic (Cpd-5)

Solvent (Solv-1)

Solvent (Solv-2)

Using an FWH-type sensitometer (color temperature of the light-source: 3,200° K), manufactured by Fuji Photo Film Co., Ltd., gradation exposure was given to the thus prepared Samples (100) to (120) through a blue filter for sensitometry, to the thus prepared Samples (200) to (220) through a green filter for sensitometry, and to the thus prepared Samples (300) to (320) through a red filter for sensitometry.

The thus exposed Samples were processed with the following processing solutions in the following processing steps:

| Processing step | Temperature | Time |
|---|---|---|
| Development | 40° C. | 15 sec |
| Bleach-fix | 40° C. | 45 sec |
| Rinse | room temperature | 45 sec |
| Alkali processing | room temperature | 30 sec |

(Developing Solution)

| | |
|---|---|
| Water | 800 ml |
| Potassium phosphate | 40 g |
| Disodium N,N-bis (sulfonatoethyl)hydroxylamine | 10 g |
| KCl | 5 g |
| Hydroxyethylidene-1,1-disulfonic acid (30%) | 4 ml |
| 1-phenyl-4-methyl-4-hydroxymethyl-3-pyrazolidone | 1 g |
| Water to make | 1,000 ml |
| pH (at 25° C. by using potassium hydroxide) | 12.0 |

(Bleach-fix Solution)

| | |
|---|---|
| Water | 600 ml |
| Ammonium thiosulfate (700 g/liter) | 93 ml |

-continued

| | |
|---|---|
| Ammonium sulfite | 40 ml |
| Ethylenediaminetetraacetic acid iron(III) ammonium salt | 55 g |
| Ethylenediaminetetraacetic acid | 2 g |
| Nitric acid (67%) | 30 g |
| Water to make | 1,000 ml |
| pH (at 25° C. by using acetic acid and ammonia water) | 5.8 |

(Rinsing Solution)

| | |
|---|---|
| Sodium chlorinated isocyanurate | 0.02 g |
| Deionized water (conductivity: 5 µS/cm or below) | 1,000 ml |
| pH | 6.5 |

(Alkali Processing Solution)

| | |
|---|---|
| Water | 800 ml |
| Potassium carbonate | 30 g |
| Water to make | 1,000 ml |
| pH (at 25° C. by using sulfuric acid) | 10.0 |

The maximum color density part of the processed Samples (100) to (120) was measured using blue light; the maximum color density part of the processed Samples (200) to (220) was measured using green light; and the maximum color density part of the processed Samples (300) to (320) was measured using red light. The results are shown in Tables 1, 2, and 3, respectively.

TABLE 1

| Sample No. | Coupler | Color developing agent | Dmax | Remarks |
|---|---|---|---|---|
| 100 | C-21 | EXCD-1 | 0.16 | Comparative Example |
| 101 | " | (57) | 0.36 | This invention |
| 102 | " | (44) | 0.60 | " |
| 103 | " | (46) | 0.62 | " |
| 104 | " | (36) | 0.76 | " |
| 105 | " | (38) | 0.72 | " |
| 106 | " | (52) | 0.32 | " |
| 107 | " | (14) | 0.39 | " |
| 108 | " | (13) | 0.56 | " |
| 109 | " | (3) | 0.66 | " |
| 110 | " | (2) | 0.68 | " |
| 111 | " | (1) | 0.78 | " |
| 112 | " | (24) | 0.33 | " |
| 113 | C-2 | EXCD-1 | 0.14 | Comparative Example |
| 114 | " | (1) | 1.02 | This invention |
| 115 | " | (36) | 1.05 | " |
| 116 | " | (71) | 0.92 | " |
| 117 | C-77 | EXCD-1 | 0.16 | Comparative Example |
| 118 | " | (1) | 0.90 | This invention |
| 119 | " | (36) | 0.95 | " |
| 120 | " | (73) | 0.81 | " |

TABLE 2

| Sample No. | Coupler | Color developing agent | Dmax | Remarks |
|---|---|---|---|---|
| 200 | C-40 | EXCD-1 | 0.21 | Comparative Example |
| 201 | " | (57) | 0.49 | This invention |
| 202 | " | (44) | 1.03 | " |
| 203 | " | (46) | 1.04 | " |
| 204 | " | (36) | 1.37 | " |
| 205 | " | (38) | 1.30 | " |
| 206 | " | (52) | 0.43 | " |
| 207 | C-47 | EXCD-1 | 0.20 | Comparative |

TABLE 2-continued

| Sample No. | Coupler | Color developing agent | Dmax | Remarks |
|---|---|---|---|---|
| | | | | Example |
| 208 | " | (14) | 0.47 | This invention |
| 209 | " | (13) | 0.71 | " |
| 210 | " | (3) | 1.28 | " |
| 211 | " | (2) | 1.33 | " |
| 212 | " | (1) | 1.38 | " |
| 213 | " | (24) | 0.41 | " |
| 214 | C-27 | EXCD-1 | 0.20 | Comparative Example |
| 215 | " | (1) | 1.45 | This invention |
| 216 | " | (66) | 1.41 | " |
| 217 | " | (75) | 1.35 | " |
| 218 | C-56 | EXCD-1 | 0.18 | Comparative Example |
| 219 | " | (36) | 1.52 | This invention |
| 220 | " | (70) | 1.36 | " |

TABLE 3

| Sample No. | Coupler | Color developing agent | Dmax | Remarks |
|---|---|---|---|---|
| 300 | C-43 | EXCD-1 | 0.18 | Comparative Example |
| 301 | " | (57) | 0.49 | This invention |
| 302 | " | (44) | 0.99 | " |
| 303 | " | (46) | 1.01 | " |
| 304 | " | (36) | 1.46 | " |
| 305 | " | (38) | 1.45 | " |
| 306 | " | (52) | 0.39 | " |
| 307 | C-41 | EXCD-1 | 0.17 | Comparative Example |
| 308 | " | (14) | 0.52 | This invention |
| 309 | " | (13) | 0.70 | " |
| 310 | " | (3) | 1.44 | " |
| 311 | " | (2) | 1.47 | " |
| 312 | " | (1) | 1.49 | " |
| 313 | " | (24) | 0.38 | " |
| 314 | C-43 | (71) | 1.47 | This invention |
| 315 | " | (74) | 1.52 | " |
| 316 | " | (66) | 1.53 | " |
| 317 | " | (68) | 1.58 | " |
| 318 | " | (69) | 1.50 | " |
| 319 | " | (76) | 1.41 | " |
| 320 | " | (80) | 1.57 | " |

As is apparent from Tables 1, 2, and 3, it can be understood that the color-developing agents of the present invention show much higher color densities in comparison with the color-developing agents for comparison. Further, the color-developing agents (1), (2), and (3), represented by formula (V), and the color-developing agents (36) and (38), represented by formula (VII), showed particularly high color-forming properties.

Example 2

A surface of a paper base, both surfaces of which had been laminated with a polyethylene, was subjected to corona discharge treatment; then it was provided with a gelatin undercoat layer containing sodium dodecylbenzensulfonate, and it was coated with various photographic constitutional layers, to produce a multi-layer photographic color printing paper (400) having the layer constitution shown below. The coating liquids were prepared as follows.

(First-Layer Coating Liquid)

22.4 g of a yellow coupler (C-21), 16.8 g of a color-developing agent (EXCD-1), and 80 g of a solvent (Solv-1)

were dissolved in ethyl acetate, and the resulting solution was emulsified and dispersed into a 16% gelatin solution containing 10% sodium dodecylbenzensulfonate and citric acid, to prepare an emulsified dispersion A. On the other hand, a silver chlorobromide emulsion A (cubes, a mixture of a large-size emulsion having an average grain size of 0.88 µm, and a small-size emulsion having an average grain size of 0.70 µm (3:7 in terms of mol of silver), the deviation coefficients of the grain size distributions being 0.08 and 0.10, respectively, and each emulsion having 0.3 mol % of silver bromide locally contained in part of the grain surface whose substrate was made up of silver chloride) was prepared. To the large-size emulsion of this emulsion, had been added $1.4 \times 10^{-4}$ mol, per mol of silver, of each of blue-sensitive sensitizing dyes A, B, and C shown below, and to the small-size emulsion of this emulsion, had been added $1.7 \times 10^{-4}$ mol, per mol of silver, of each of blue-sensitive sensitizing dyes A, B, and C shown below. The chemical ripening of this emulsion was carried out with a sulfur sensitizer and a gold sensitizer being added. The above emulsified dispersion A and this silver chlorobromide emulsion A were mixed and dissolved, and a first-layer coating liquid was prepared so that it would have the composition shown below. The coating amount of the emulsion is in terms of silver.

In the similar way as the method of preparing of the first-layer coating liquid, coating liquids for the second layer to the seventh layer were prepared. As the gelatin hardeners for each layers, 1-oxy-3,5-dichloro-s-triazine sodium salt was used.

Further, to each layer, were added Cpd-2, Cpd-3, Cpd-4, and Cpd-5, so that the total amounts would be 15.0 mg/m², 60.00 mg/m², 50.0 mg/m², and 10.0 mg/m², respectively.

For the silver chlorobromide emulsion of each photosensitive emulsion layer, the following spectral sensitizing dyes were used.

(Blue-Sensitive Emulsion Layer)

Sensitizing dye A

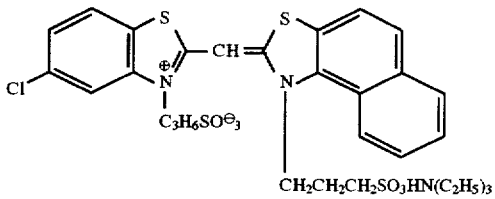

Sensitizing dye B

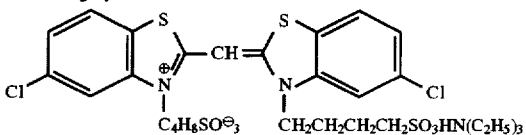

Sensitizing dye C

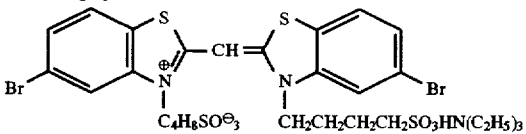

(Red-Sensitive Emulsion Layer)

Sensitizing dye D

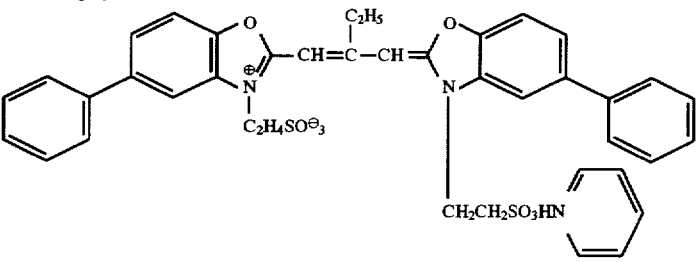

Sensitizing dye E

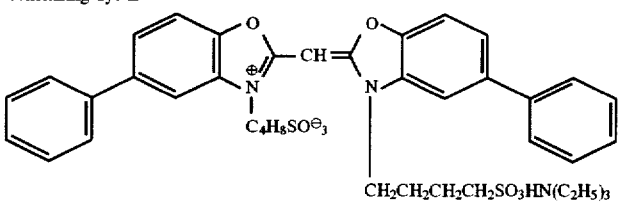

-continued

Sensitizing dye F

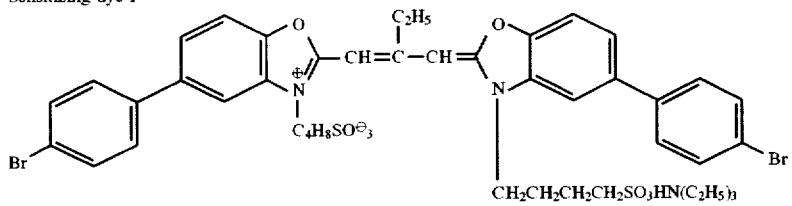

The sensitizing dye D was added to the large-size emulsion in an amount of $3.0\times10^{-4}$ mol per mol of the silver halide, and to the small-size emulsion in an amount of $3.6\times10^{-4}$ mol per mol of the silver halide; the sensitizing dye E was added to the large-size emulsion in an amount of $4.0\times10^{-5}$ mol per mol of the silver halide, and to the small-size emulsion in an amount of $7.0\times10^{-5}$ mol per mol of the silver halide; and the sensitizing dye F was added to the large-size emulsion in an amount of $2.0\times10^{-4}$ mol per mol of the silver halide, and to the small-size emulsion in an amount of $2.8\times10^{-4}$ mol per mol of the silver halide.

(Red-Sensitive Emulsion Layer)

Sensitizing dye G

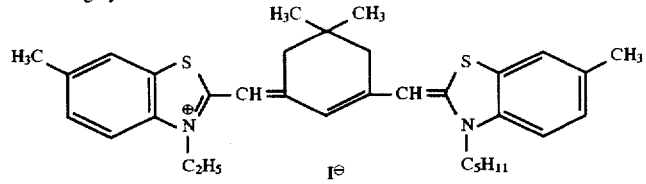

Sensitizing dye H

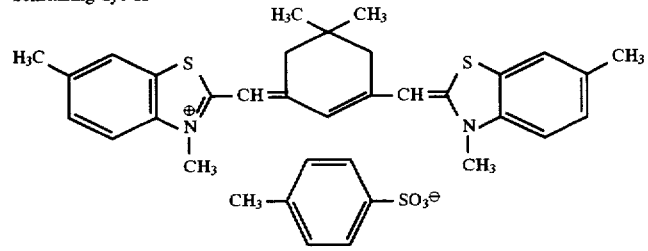

(Each was added to the large-size emulsion in an amount of $5.0\times10^{-5}$ mol per mol of the silver halide, and to the small-size emulsion in an amount of $8.0\times10^{-5}$ per mol of the silver halide.)

The following compound was added in an amount of $2.6\times10^{-2}$ mol per mol of the silver halide.

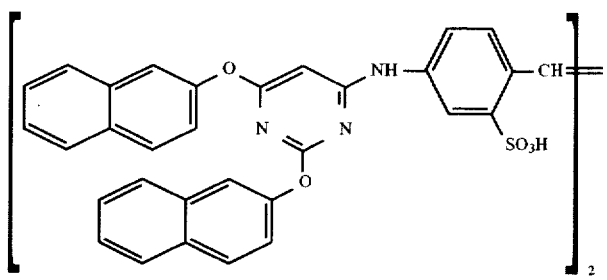

To the blue-sensitive emulsion layer, the green-sensitive emulsion layer, and the red-sensitive emulsion layer, was added 1-(5-methylureidophenyl)-5-mercaptotetrazole in amounts of $3.5\times10^{-4}$ mol, $3.0\times10^{-3}$ mol, and $2.5\times10^{-4}$ mol, respectively, per mol of the silver halide. Further, to the blue-sensitive emulsion layer and the green-sensitive emulsion layer, was added 4-hydroxy-6-methyl-1,3,3a,7-tetrazaindene in amounts of $1\times10^{-4}$ and $2\times10^{-4}$, respectively, per mol of the silver halide.

Further, to prevent irradiation, the following dye was added to the emulsion layers (the coating amount is shown in parentheses).

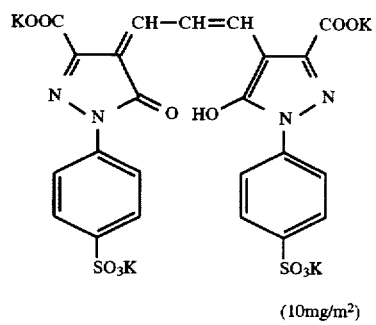

(10mg/m²)

and

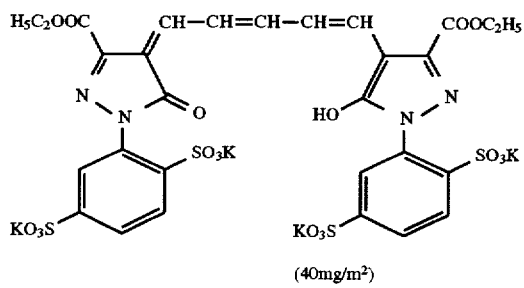

(40mg/m²)

(Layer Constitution)

The composition of each layer is shown below. The numbers show coating amounts (g/m²). In the case of the silver halide emulsion, the coating amount is in terms of silver.

Base

Polyethylene-Laminated Paper

|The polyethylene on the first layer side contained a white pigment (TiO₂) and a blue dye (ultramarine)|

| First Layer (Blue-Sensitive Emulsion Layer) | |
|---|---|
| The above silver chlorobromide emulsion A | 0.40 |
| Gelatin | 3.00 |
| Yellow coupler (C-21) | 0.45 |
| Color developing agent (EXCD-1) | 0.34 |
| Solvent (Solv-1) | 1.60 |
| Second Layer (Color Mixing Inhibiting Layer) | |
| Gelatin | 1.09 |
| Color mixing inhibitor (Cpd-6) | 0.11 |
| Solvent (Solv-1) | 0.19 |
| Solvent (Solv-3) | 0.07 |
| Solvent (Solv-4) | 0.25 |
| Solvent (Solv-5) | 0.09 |

Third Layer (Green-Sensitive Emulsion Layer)

A silver chlorobromide emulsion: cubes, a mixture of a large-size emulsion having an average grain size of 0.55 μm, and a small-size emulsion having an average grain size of 0.39 μm (1:3 in terms of mol of silver. The deviation coefficients of the grain size distributions were 0.10 and 0.08, respectively, and each emulsion had 0.8 mol % of AgBr contained in part of the grain surface whose substrate was made up of silver chloride.

| | |
|---|---|
| Gelatin | 1.50 |
| Magenta coupler (C-40) | 0.26 |
| Color developing agent (EXCD-1) | 0.17 |
| Solvent (Solv-2) | 0.80 |
| Fourth Layer (Color Mixing Inhibiting Layer) | |
| Gelatin | 0.77 |
| Color mixing inhibitor (Cpd-6) | 0.08 |
| Solvent (Solv-1) | 0.14 |
| Solvent (Solv-3) | 0.05 |
| Solvent (Solv-4) | 0.14 |
| Solvent (Solv-5) | 0.06 |

Fifth Layer (Red-Sensitive Emulsion Layer)

A silver chlorobromide emulsion: cubes, a mixture of a large-size emulsion having an average grain size of 0.5 μm, and a small-size emulsion having an average grain size of 0.41 μm (1:4 in terms of mol of silver). The deviation coefficients of the grain size distributions were 0.09 and 0.11, respectively, and each emulsion had 0.8 mol % of silver bromide locally contained in part of the grain surface whose substrate was made up of silver chloride.

| | |
|---|---|
| Gelatin | 0.15 |
| Cyan coupler (C-43) | 0.22 |
| Color developing agent (EXCD-1) | 0.17 |
| Solvent (Solv-1) | 0.18 |

| Sixth Layer (Ultraviolet Absorbing Layer) | |
|---|---|
| Gelatin | 0.64 |
| Ultraviolet absorbing agent (UV-1) | 0.39 |
| Color image stabilizer (Cpd-7) | 0.05 |
| Solvent (Solv-6) | 0.05 |
| Seventh Layer (Protective Layer) | |
| Gelatin | 1.10 |
| Acryl-modified copolymer of polyvinyl alcohol (modification degree: 17%) | 0.04 |
| Liquid paraffin | 0.02 |
| Surface-active agent (Cpd-1) | 0.01 |

(Cpd-6) color mixing inhibitor
mixture (by weight ratio) of (1):(2):(3) = 1:1:1

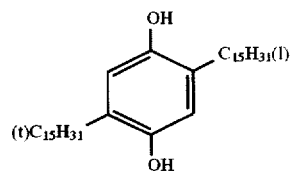
(1)

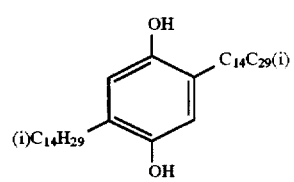
(2)

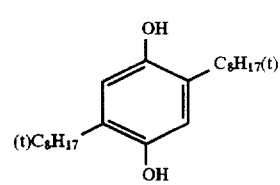
(3)

(Cpd-7) Color image stabilizer

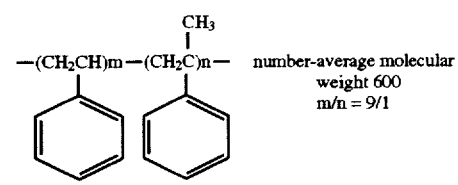
number-average molecular weight 600
m/n = 9/1

(Solv-3) Solvent
$C_8H_{17}CH\underset{O}{\overset{}{\diagdown\diagup}}CH(CH_2)_7COOC_8H_{17}$ (Solv-4) Solvent
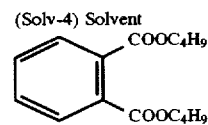

(Solv-5) Solvent
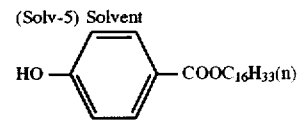

(Solv-6) Solvent
$C_8H_{17}OCO-(CH_2)_8-COOC_8H_{17}$ (UV-1) Ultraviolet absorbent
mixture (by weight ratio) of
(1):(2):(3):(4):(5) = 1:2:2:3:1

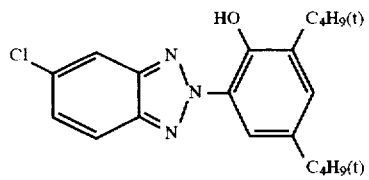
(1)

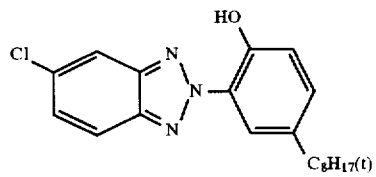
(2)

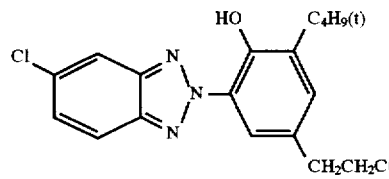
(3)

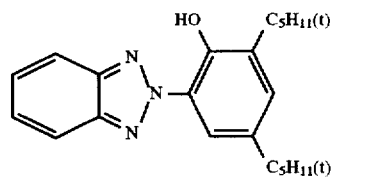
(4)

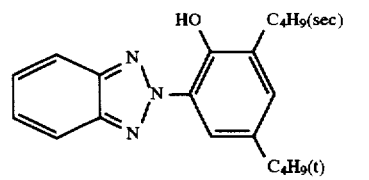
(5)

The procedure for the preparation of Sample (400) was repeated, except that instead of the coupler and the color-developing agent, the couplers and the color developing agents shown in Table 4 were used, in the same molar amounts, thereby preparing Samples (401) to (405).

By using an FWH-type sensitometer (color temperature of the light source: 3,200° K), manufactured by Fuji Photo Film Co., Ltd., gradation exposure was given to all of the thus prepared Samples through a three color separation filter for sensitometry.

The thus exposed Samples were processed with the following processing solutions in the following processing steps:

| Processing step | Temperature | Time |
|---|---|---|
| Development | 40° C. | 15 sec |
| Bleach-fix | 40° C. | 45 sec |
| Rinse | room temperature | 45 sec |
| Alkali processing | room temperature | 30 sec |

| (Developing Solution) | |
|---|---|
| Water | 800 ml |
| Potassium phosphate | 40 g |
| Disodium N,N-bis (sulfonatoethyl)hydroxylamine | 10 g |
| KCl | 5 g |
| Hydroxylethylidene-1,1-disulfonic acid (30%) | 4 ml |
| 1-phenyl-4-methyl-4-hydroxymethyl-3-pyrazolidone | 1 g |
| Water to make | 1,000 ml |
| pH (at 25° C. by using potassium hydroxide) | 12.0 |

-continued (Bleach-fix Solution)

| | |
|---|---|
| Water | 600 ml |
| Ammonium thiosulfate (700 g/liter) | 93 ml |
| Ammonium sulfite | 40 ml |
| Ethylenediaminetetraacetic acid iron (III) ammonium salt | 55 g |
| Ethylenediamintetraacetic acid | 2 g |
| Nitric acid (67%) | 30 g |
| Water to make | 1,000 ml |
| pH (at 25° C. by using acetic acid and ammonia water) | 5.8 |

(Rinsing Solution)

| | |
|---|---|
| Sodium chlorinated isocyanurate | 0.02 g |
| Deionized water (conductivity: 5 μS/cm or below) | 1,000 ml |
| pH | 6.5 |

(Alkali Processing Solubion)

| | |
|---|---|
| Water | 800 ml |
| Potassium cabonate | 30 g |
| Water to make | 1,000 ml |
| pH (at 25° C. by using sulfuric acid) | 10.0 |

The maximum color density part of the processed Samples was measured using red light, green light, and blue light. The results are shown in Table 4.

The liquid (1) and the liquid (2) shown in Table 5 were added simultaneously, at the same flow rate, over 19 min, to an aqueous gelatin solution (prepared by adding 16 g of gelatin, 0.24 g of potassium bromide, 1.6 g of sodium chloride, and 24 mg of a compound (a) to 540 ml of water, followed by heating to 55° C.) that was being stirred well. After 5 min, the liquid (3) and the liquid (4) shown in Table 5 were added simultaneously, over 24 min, in the same liquid amount. The mixture was washed with water and was desalted in a usual manner; then 17.6 g of lime-processed ossein gelatin and 56 mg of a compound (b) were added, the pH and the pAg were adjusted to 6.2 and 7.7, respectively, and then 0.41 g of a ribonucleic acid degradation product and 1.02 mg of trimethylthiourea were added, to carry out optimum chemical sensitization at 60° C. Thereafter, 0.18 g of 4-hydroxy-6-methyl-1,3,3a,7-tetrazaindene, 64 mg of a sensitizing dye (c), and 0.41 g of potassium bromide were added, successively, followed by cooling. Thus, 590 g of a monodisperse cube silver chlorobromide emulsion having an average grain size of 0.30 μm was obtained.

TABLE 4

| Sample No. | Yellow coupler | Magenta coupler | Cyan coupler | Color developing agent | Yellow Dmax | Magenta Dmax | Cyan Dmax | Remarks |
|---|---|---|---|---|---|---|---|---|
| 400 | C-21 | C-40 | C-43 | EXCD-1 | 0.24 | 0.32 | 0.29 | Comparative Example |
| 401 | " | " | " | (36) | 1.48 | 1.32 | 1.40 | This invention |
| 402 | " | " | " | (38) | 1.40 | 1.40 | 1.38 | " |
| 403 | " | C-47 | C-41 | EXCD-1 | 0.20 | 0.20 | 0.22 | Comparative Example |
| 404 | " | " | " | (1) | 1.46 | 1.46 | 1.42 | This invention |
| 405 | " | " | " | (3) | 1.38 | 1.38 | 1.38 | " |

As is apparent from Table 4, the multi-layer photographic materials gave similar results to those of the single-layer photographic materials shown in Example 1.

Example 3

<Preparation Method of Photosensitive Silver Halide Emulsions>

Photosensitive Silver Halide Emulsion (1) [for Red-Sensitive Emulsion Layer]

TABLE 5

| | Liquid (1) | Liquid (2) | Liquid (3) | Liquid (4) |
|---|---|---|---|---|
| AgNO₃ | 24.0 g | — | 56.0 g | — |
| NH₄NO₃ | 50.0 mg | — | 50.0 mg | — |
| KBr | — | 10.9 g | — | 35.3 g |
| NaCl | — | 2.88 g | — | 1.92 g |
| K₂IrCl₆ | — | 0.07 mg | — | — |
| Total amount | Water to make 130 ml | Water to make 200 ml | Water to make 130 ml | Water to make 200 ml |

Compound (a)

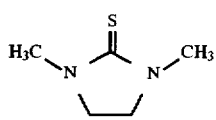

Compound (b)

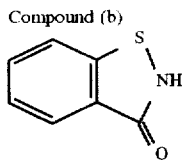

-continued

Sensitizing dye (c)

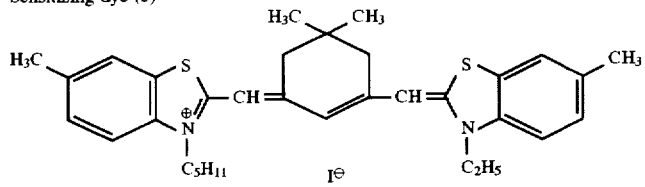

Photosensitive Silver Halide Emulsion (2) (for Green-Sensitive Emulsion Layer]

The liquid (1) and the liquid (2) shown in Table 6 were added simultaneously, at the same flow rate, over 10 min. to an aqueous gelatin solution (prepared by adding 20 g of gelatin, 0.30 g of potassium bromide, 2.0 g of sodium chloride, and 30 mg of a compound (a) to 600 ml of water, followed by heating to 46° C.) that was being stirred well. After 5 min. the liquid (3) and the liquid (4) shown in Table 6 were added simultaneously, over 30 min. at the same flow rate. One min after the completion of the addition of the liquids (3) and (4), 60 ml of a methanol solution containing sensitizing dyes (sensitizing dye ($d_1$): 360 mg; and sensitizing dye ($d_2$): 73.4 mg) were added, at one stroke. The mixture was washed with water and was desalted (using a settling agent (e) at a pH of 4.0) in a usual manner; then 22 g of lime-processed ossein gelatin was added, the pH and the pAg were adjusted to 6.0 and 7.6, respectively, and then 1.8 mg of sodium thiosulfate and 180 mg of 4-hydroxy-6-methyl-1,3,3a,7-tetrazaindene were added, to carry out optimum chemical sensitization at 60° C. Then, 90 mg of an antifoggant (f), and 70 mg of a compound (b) and 3 ml of a compound (g) as antiseptics were added, followed by cooling. Thus, 635 g of a monodisperse cube silver chlorobromide emulsion having an average grain size of 0.30 μm was obtained.

TABLE 6

|  | Liquid (1) | Liquid (2) | Liquid (3) | Liquid (4) |
| --- | --- | --- | --- | --- |
| $AgNO_3$ | 10.0 g | — | 90.0 g | — |
| $NH_4NO_3$ | 60.0 mg | — | 380 mg | — |
| KBr | — | 3.50 g | — | 57.1 g |
| NaCl | — | 1.72 g | — | 3.13 g |
| $K_2IrCl_6$ | — | — | — | 0.03 mg |
| Total amount | Water to make 126 ml | Water to make 131 ml | Water to make 280 ml | Water to make 289 ml |

Dye ($d_1$)

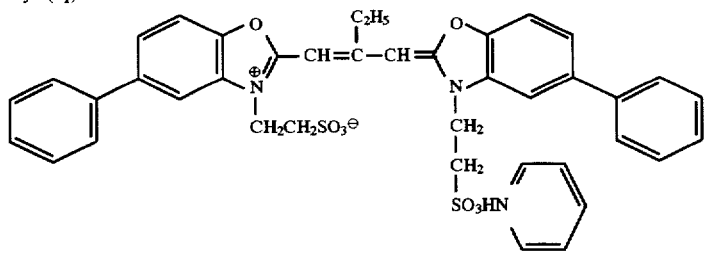

Dye($D_2$)

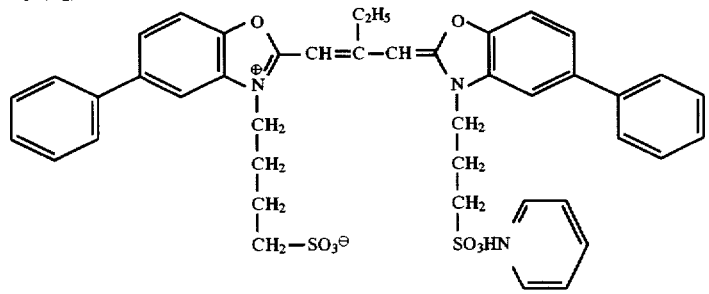

Settling agent (e)

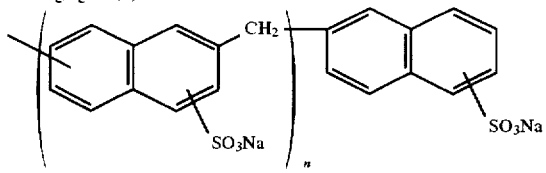

Antifoggant (f)

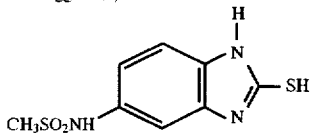

Compound (g)
OCH₂CH₂OH

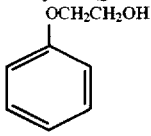

Photosensitive Silver Halide Emulsion (3) [for Blue-Sensitive Emulsion Layer]

Addition was started of the liquid (2), shown in Table 7, to an aqueous gelatin solution (prepared by adding 31.6 g of gelatin, 2.5 g of potassium bromide, and 13 mg of a compound (a) to 584 ml of water, followed by heating to 70° C.) that was being well stirred; and 10 sec after the start of the addition, addition was started of the liquid (1), shown in Table 7. Thereafter the liquids (1) and (2) were added over 30 min. Five min after the completion of the addition of the liquid (2), addition was started of the liquid (4), shown in Table 7, and 10 sec later, addition was started of the liquid (3), which was added over 27 min and 50 sec, and the liquid (4) was added over 28 min. The mixture was washed with water and was desalted (using a settling agent (e) at a pH of 3.9) in a usual manner; then 24.6 g of lime-processed ossein gelatin and 56 mg of a compound (b) were added, the pH and the pAg were adjusted to 6.1 and 8.5, respectively, and then 0.55 mg of sodium thiosulfate was added, to carry out optimum chemical sensitization at 65° C. Then, 0.35 g of a sensitizing dye (h), 56 mg of an antifoggant (f), and 2.3 ml of a compound (g), as an antiseptic, were added, followed by cooling. Thus, 582 g of a monodisperse octahedron silver bromide emulsion having an average grain size of 0.55 μm was obtained.

TABLE 7

|  | Liquid (1) | Liquid (2) | Liquid (3) | Liquid (4) |
|---|---|---|---|---|
| AgNO₃ | 15.8 g | — | 72.2 g | — |
| NH₄NO₃ | 68.0 mg | — | 308 mg | — |
| KBr | — | 11.4 g | — | 52.2 g |
| Total amount | Water to make 134 ml | Water to make 134 ml | Water to make 194 ml | Water to make 195 ml |

Settling agent (b)

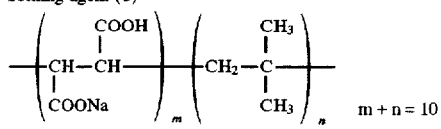

Sensitizing dye (h)

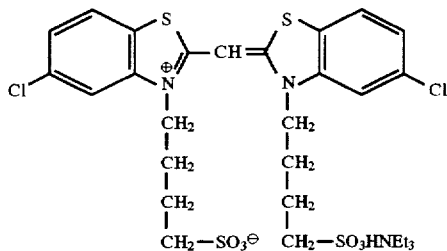

Antifoggant (i)

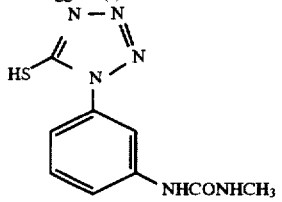

Benzotriazole Silver Emulsion [Organic Silver Salt]

28 g of gelatin and 13.2 g of benzotriazole were dissolved in 300 ml of water. The resulting solution was kept at 40° C. and stirred. To this solution was added a solution of 17 g of silver nitrate in 1,000 ml of water, over 2 min. The pH of this benzotriazole silver emulsion was adjusted, and excess salts were precipitated and removed. Thereafter the pH was adjusted to 6.30, thereby obtaining 400 g of a benzotriazole silver emulsion.

<Preparation Method of emulsified Dispersion of Coupler>

The oil-phase components and the aqueous-phase components of each composition shown in Table 8 were dissolved, respectively, to obtain uniform solutions at 60° C. The oil-phase components and the aqueous-phase components were combined together and were dispersed in a 1-liter stainless steel vessel, by a dissolver equipped with a disperser having a diameter of 5 cm, at 10,000 rpm for 20 min. Warm water (as an additional water) was added thereto in the amount shown in Table 8, followed by stirring at 2,000 rpm for 10 min. Thus, emulsified dispersions containing three couplers, that is, cyan, magenta, and yellow couplers, were prepared.

TABLE 8

|  | Cyan | Magenta | Yellow |
|---|---|---|---|
| Cyan coupler (C-43) | 2.82 g | — | — |
| Magenta coupler (C-40) | — | 3.29 g | — |
| Yellow coupler (C-21) | — | — | 2.86 g |
| Color developing agent (EXCD-1) | 2.40 g | 2.40 g | 2.40 g |
| Antifoggant (5) | 0.08 g | 0.08 g | 0.08 g |
| High-boiling solvent (6) | 4.08 g | 4.85 g | 3.83 g |
| Ethyl acetate | 24 ml | 24 ml | 24 ml |
| Lime-processed gelatin | 5.0 g | 5.0 g | 5.0 g |
| Surface-active agent (7) | 0.40 g | 0.40 g | 0.40 g |
| Water | 75.0 ml | 75.0 ml | 75.0 ml |
| Additional water | 60.0 ml | 60.0 ml | 60.0 ml |

Cyan coupler (C-43)

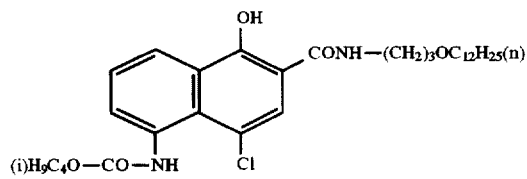

Magenta coupler (C-40)

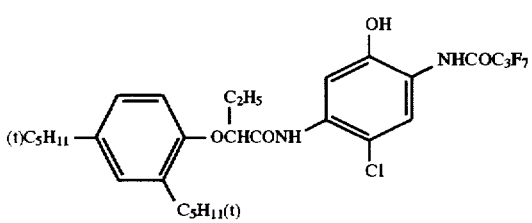

Yellow coupler (C-21)

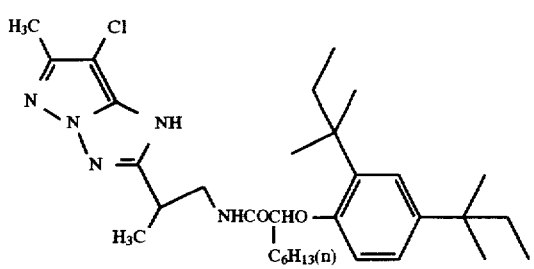

Reducing agent for color developing (EXCD-1)

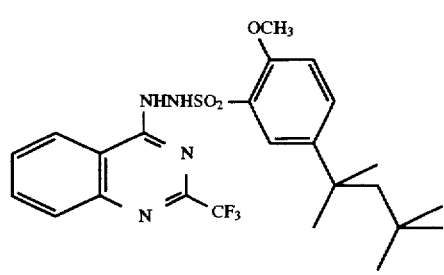

(Compound described in EP Patent No. 545491A1)

Antifoggant (5)

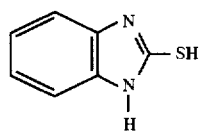

High-boiling solvent (6)

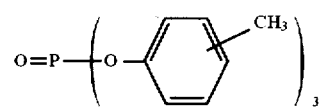

Surface active agent (7)

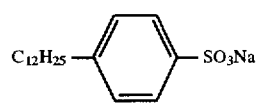

By using the thus obtained material, a heat-processable color photographic material 501, having the multi-layer constitution shown in Table 9, was produced.

TABLE 9

Constitution of light-sensitive material 501

| Layer constitution | Additive | Added amount (mg/m²) |
|---|---|---|
| Sixth layer Protective layer | Lime-proceed gelatin | 1940 |
|  | Matting agent (silica) | 200 |
|  | Surface-active agent (8) | 50 |
|  | Surface-active agent (9) | 300 |
|  | Base precursor (10) | 1400 |
|  | Water-soluble polymer (11) | 120 |
| Fifth layer Yellow color-forming layer | Lime-processed gelatin | 2000 |
|  | Blue-sensitive silver halide emulsion | 1250 (in terms of silver) |
|  | Benzotriazole silver emulsion | 300 (in terms of silver) |
|  | Yellow coupler (C-21) | 570 |
|  | Color developing agent (EXCD-1) | 480 |
|  | Antifoggant (5) | 16 |
|  | High-boiling solvent (6) | 774 |
|  | Surface-active agent (7) | 80 |
|  | Heat solvent (12) | 1400 |
|  | Surface-active agent (9) | 70 |
|  | Water-soluble polymer (11) | 40 |
| Fourth layer Intermediate layer | Lime-processed gelatin | 970 |
|  | Surface-active agent (8) | 50 |
|  | Surface-active agent (9) | 300 |
|  | Base precursor (10) | 1400 |
|  | Water-soluble polymer (11) | 60 |
| Third layer Magenta color-forming layer | Lime-processed gelatin | 1000 |
|  | Green-sensitive silver halide emulsion | 625 (in terms of silver) |
|  | Benzotriazole silver emulsion | 150 (in terms of silver) |
|  | Magenta coupler (C-40) | 330 |
|  | Color developing agent (EXCD-1) | 240 |
|  | Antifoggant (5) | 8 |
|  | High-boiling solvent (6) | 490 |
|  | Surface-active agent (7) | 40 |
|  | Heat solvent (12) | 700 |
|  | Surface-active agent (9) | 35 |
|  | Water-soluble polymer (11) | 20 |
| Second layer Intermediate layer | Lime-processed gelatin | 970 |
|  | Surface-active agent (8) | 50 |
|  | Surface-active agent (9) | 300 |
|  | Base precursor (10) | 1400 |
|  | Water-soluble polymer (11) | 60 |

TABLE 9-continued

Constitution of light-sensitive material 501

| Layer constitution | Additive | Added amount (mg/m²) |
|---|---|---|
| First layer Cyan color-forming layer | Lime-processed gelatin | 1000 |
| | Red-sensitive silver halide emulsion | 625 (in terms of silver) |
| | Benzotriazole silver emulsion | 150 (in terms of silver) |
| | Cyan coupler (C-43) | 280 |
| | Color developing agent (EXCD-1) | 240 |
| | Antifoggant (5) | 8 |
| | High-boiling solvent (6) | 410 |
| | Surface-active agent (7) | 40 |
| | Heat solvent (12) | 700 |
| | Surface-active agent (9) | 35 |
| | Water-soluble polymer (11) | 20 |
| | Transparent PET base (102 μm) | |

Surface-active agent (8)

$NaO_3S-CH-COOC_8H_{17}$
$\quad\quad\quad\;\;|$
$\quad\quad\quad CH_2-COOC_8H_{17}$ Surface-active agent (9)

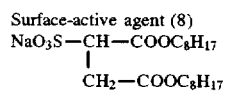

$C_9H_{19}\text{—}\phantom{x}\text{—}O(CH_2CH_2O)_{8.5}\text{—}OH$

Base precursor (10)

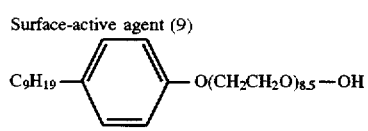

$CCl_3COO^{\ominus}\quad H_2\overset{\oplus}{N}=C$
$\quad\quad\quad\quad\quad\quad\quad\quad / \;\; \backslash$
$\quad\quad\quad\quad\quad\quad NH_2 \quad NH_2$ Water-soluble polymer (11)

—(CH₂—CH)—

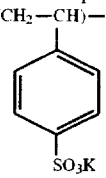

SO₃K

Heat solvent (12)
D-Sorbitol

The procedure for the preparation of 501 was repeated, except that the color-developing agent and the couplers were changed as shown in Table 10, thereby producing photographic materials 502 to 522. These samples were exposed to light at 2,000 lux for 1 sec through B, G, and R filters, with the density changed continuously. The exposed samples were heat-developed for 10 sec, by bringing the base side in contact with a heat drum heated to 140° C. After the processing, they were removed from the drum, thereby obtaining cyan, magenta, and yellow color images corresponding to the filters used for the exposure. Immediately after the processing, the maximum density part ($D_{max}$) and the minimum density part ($D_{min}$) of these samples were measured by an X-rite density-measuring machine, and the results are shown in Table 11.

TABLE 10

| Sample No. | | Cyan Coupler | Cyan Color developing agent | Cyan Added amount | Magenta Coupler | Magenta Color developing agent | Magenta Added amount | Yellow Coupler | Yellow Color developing agent | Yellow Added amount |
|---|---|---|---|---|---|---|---|---|---|---|
| 501 | (Comparative Example) | C-43 | EXCD-1 | 1.0 | C-40 | EXCD-1 | 1.0 | C-21 | EXCD-1 | 1.0 |
| 502 | (") | " | " | 2.0 | " | " | 2.0 | " | " | 2.0 |
| 503 | (") | C-41 | " | 1.0 | C-47 | " | 1.0 | " | " | 1.0 |
| 504 | (") | " | " | 2.0 | " | " | 2.0 | " | " | 2.0 |
| 505 | (This Invention) | C-43 | (57) | 1.0 | C-40 | (57) | 1.0 | " | (57) | 1.0 |
| 506 | (") | " | (47) | 1.0 | " | (47) | 1.0 | " | (47) | 1.0 |
| 507 | (") | " | (38) | 1.0 | " | (38) | 1.0 | " | (38) | 1.0 |
| 508 | (") | " | (36) | 1.0 | " | (36) | 1.0 | " | (36) | 1.0 |
| 509 | (") | " | (36) | 2.0 | " | (36) | 2.0 | " | (36) | 2.0 |
| 510 | (") | " | (52) | 1.0 | " | (52) | 1.0 | " | (52) | 1.0 |
| 511 | (") | C-41 | (14) | 1.0 | C-47 | (14) | 1.0 | " | (14) | 1.0 |
| 512 | (") | " | (13) | 1.0 | " | (13) | 1.0 | " | (13) | 1.0 |
| 513 | (") | " | (3) | 1.0 | " | (3) | 1.0 | " | (3) | 1.0 |
| 514 | (") | " | (1) | 1.0 | " | (1) | 1.0 | " | (1) | 1.0 |
| 515 | (") | " | (1) | 2.0 | " | (1) | 2.0 | " | (1) | 2.0 |
| 516 | (") | " | (24) | 1.0 | " | (24) | 1.0 | " | (24) | 1.0 |
| 517 | (Comparative Example) | C-41 | EXCD-1 | 1.0 | C-27 | EXCD-1 | 1.0 | C-2 | EXCD-1 | 1.0 |
| 518 | (This Invention) | " | (71) | 1.0 | " | (71) | 1.0 | " | (71) | 1.0 |
| 519 | (") | " | (73) | 1.0 | " | (73) | 1.0 | " | (73) | 1.0 |
| 520 | (Comparative Example) | C-43 | EXCD-1 | 1.0 | C-56 | EXCD-1 | 1.0 | C-77 | EXCD-1 | 1.0 |
| 521 | (This Invention) | " | (36) | 1.0 | " | (36) | 1.0 | " | (36) | 1.0 |
| 522 | (") | " | (68) | 1.0 | " | (68) | 1.0 | " | (68) | 1.0 |

The added amount is expressed in a molar ratio to the color developing agent in each layer of the light-sensitive material in 501.

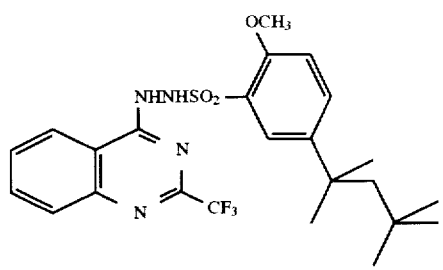
EXCD-1
(Compound described in EP Patent No. 545491A1)
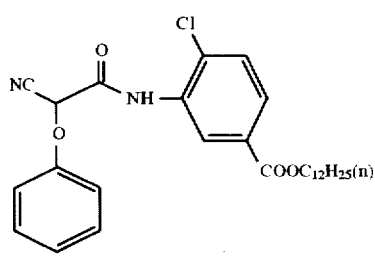
(C-2)
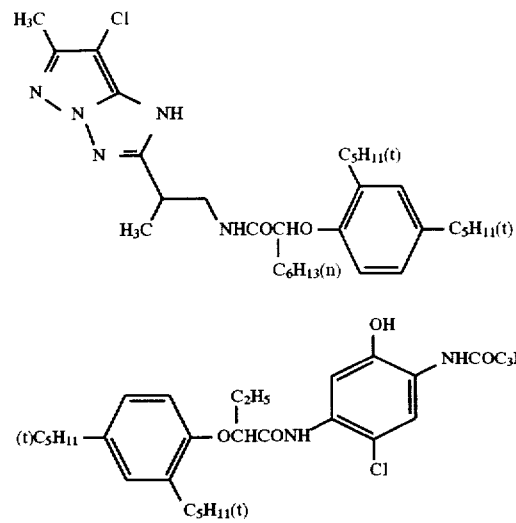
(C-21)
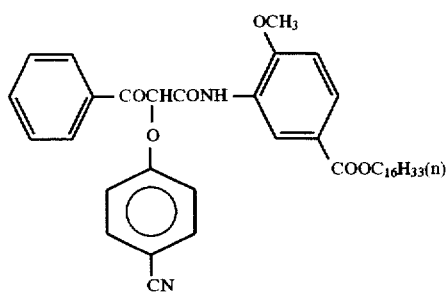
(C-77)
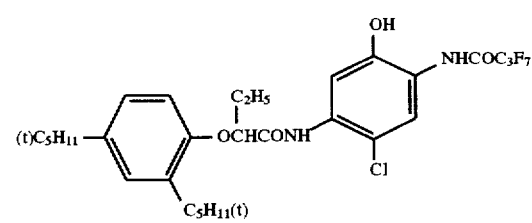
(C-40)
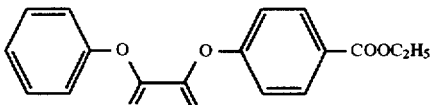
(C-27)
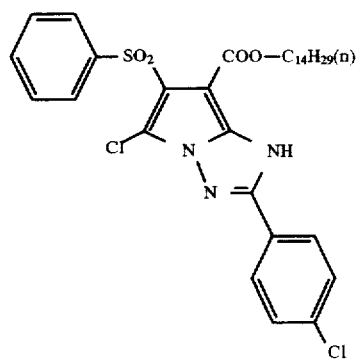
(C-47)
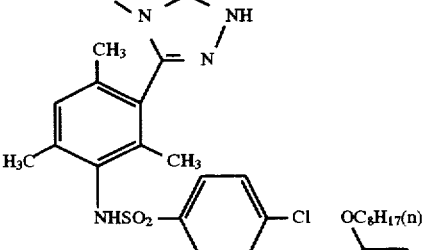
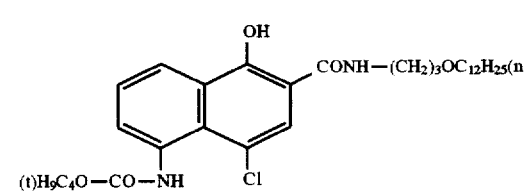
(C-43)
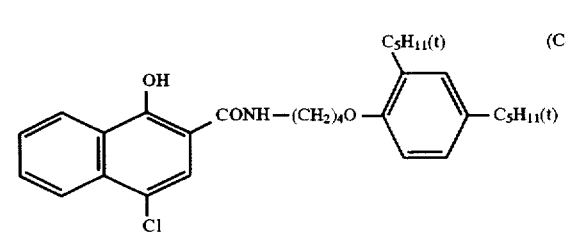
(C-41)
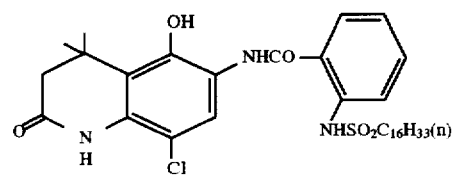
(C-56)

TABLE 11

| | | Before storage | | | | | |
|---|---|---|---|---|---|---|---|
| | | Cyan | | Magenta | | Yellow | |
| Sample No. | | Dmax | Dmin | Dmax | Dmin | Dmax | Dmin |
| 501 | (Comparative Example) | 0.25 | 0.20 | 0.22 | 0.20 | 0.25 | 0.21 |
| 502 | (Comparative Example) | 0.26 | 0.22 | 0.23 | 0.21 | 0.30 | 0.21 |
| 503 | (Comparative Example) | 0.24 | 0.20 | 0.25 | 0.20 | 0.24 | 0.20 |
| 504 | (Comparative Example) | 0.28 | 0.21 | 0.28 | 0.24 | 0.27 | 0.21 |
| 505 | (This Invention) | 0.70 | 0.20 | 0.72 | 0.19 | 0.74 | 0.20 |
| 506 | (This Invention) | 1.20 | 0.21 | 1.14 | 0.37 | 1.16 | 0.77 |
| 507 | (This Invention) | 1.42 | 0.22 | 1.28 | 0.21 | 1.38 | 0.22 |
| 508 | (This Invention) | 1.45 | 0.20 | 1.32 | 0.20 | 1.49 | 0.20 |
| 509 | (This Invention) | 1.60 | 0.22 | 1.45 | 0.21 | 1.63 | 0.22 |
| 510 | (This Invention) | 0.48 | 0.20 | 0.49 | 0.20 | 0.50 | 0.21 |
| 511 | (This Invention) | 0.55 | 0.21 | 0.52 | 0.20 | 0.54 | 0.20 |
| 512 | (This Invention) | 0.88 | 0.22 | 0.75 | 0.21 | 0.93 | 0.20 |
| 513 | (This Invention) | 1.38 | 0.20 | 1.32 | 0.20 | 1.39 | 0.21 |
| 514 | (This Invention) | 1.42 | 0.22 | 1.38 | 0.21 | 1.50 | 0.20 |
| 515 | (This Invention) | 1.48 | 0.22 | 1.41 | 0.22 | 1.59 | 0.22 |
| 516 | (This Invention) | 0.49 | 0.24 | 0.41 | 0.21 | 0.48 | 0.20 |
| 517 | (Comparative Example) | 0.23 | 0.20 | 0.21 | 0.20 | 0.22 | 0.21 |
| 518 | (This Invention) | 1.61 | 0.23 | 1.52 | 0.23 | 1.62 | 0.24 |
| 519 | (This Invention) | 1.60 | 0.22 | 1.48 | 0.22 | 1.53 | 0.22 |
| 520 | (Comparative Example) | 0.26 | 0.22 | 0.23 | 0.20 | 0.23 | 0.20 |
| 521 | (This Invention) | 1.49 | 0.24 | 1.42 | 0.22 | 1.54 | 0.23 |
| 522 | (This Invention) | 1.53 | 0.22 | 1.43 | 0.21 | 1.60 | 0.21 |

Summarizing the results shown in Table 11, it can be understood that in the photographic materials 501 to 504, 517, and 520, which use color-developing agents of Comparative Examples, even when the amounts to be added are increased, images excellent in discrimination cannot be obtained, while in the photographic materials 505 to 516, 518, 519, 521, and 522 which use color-developing agents of the present invention, images excellent in discrimination can be obtained. From the above, the effect of the present invention is apparent.

Example 4
(Preparation Method of Zinc Hydroxide Dispersion)

31 g of zinc hydroxide powder, whose primary particles had a grain size of 0.2 μm, 1.6 g of carboxylmethylcellulose and 0.4 g of sodium polyacrylate, as a dispersant, 8.5 g of lime-processed ossein gelatin, and 158.5 ml of water were mixed together, and the mixture was dispersed by a mill containing glass beads for 1 hour. After the dispersion, the glass beads were filtered off, to obtain 188 g of a dispersion of zinc hydroxide.

By using the thus obtained dispersion of zinc hydroxide, a heat-processable color photographic material 601, shown in Table 12, was produced.

TABLE 12

| Constitution of light-sensitive material 601 | | |
|---|---|---|
| Layer constitution | Additive | Added amount (mg/m²) |
| Sixth layer Protective layer | Lime-proceed gelatin | 1940 |
| | Matting agent (silica) | 200 |
| | Surface-active agent (8) | 50 |
| | Surface-active agent (9) | 300 |
| | Base precursor (10) | 600 |
| | Water-soluble polymer (11) | 120 |
| Fifth layer Yellow color- | Lime-processed gelatin | 2000 |
| | Blue-sensitive silver halide | 1250 (in terms |

TABLE 12-continued

| Constitution of light-sensitive material 601 | | |
|---|---|---|
| Layer constitution | Additive | Added amount (mg/m²) |
| forming layer | emulsion | of silver) |
| | Yellow coupler (C-21) | 570 |
| | Color developing agent (EXCD-1) | 480 |
| | Antifoggant (5) | 16 |
| | High-boiling solvent (6) | 774 |
| | Surface-active agent (7) | 80 |
| | Water-soluble polymer (11) | 40 |
| Fourth layer Intermediate layer | Lime-processed gelatin | 970 |
| | Surface-active agent (8) | 50 |
| | Surface-active agent (9) | 300 |
| | Zinc hydroxide | 400 |
| | Water-soluble polymer (11) | 60 |
| Third layer Magenta color-forming layer | Lime-processed gelatin | 1000 |
| | Green-sensitive silver halide emulsion | 625 (in terms of silver) |
| | Magenta coupler (C-40) | 330 |
| | Color developing agent (EXCD-1) | 240 |
| | Antifoggant (5) | 8 |
| | High-boiling solvent (6) | 490 |
| | Surface-active agent (7) | 40 |
| | Heat solvent (12) | 20 |
| Second layer Intermediate layer | Lime-processed gelatin | 970 |
| | Surface-active agent (8) | 50 |
| | Surface-active agent (9) | 300 |
| | Zinc hydroxide | 400 |
| | Water-soluble polymer (11) | 60 |
| First layer Cyan color-forming layer | Lime-processed gelatin | 1000 |
| | Red-sensitive silver halide emulsion | 625 (in terms of silver) |
| | Cyan coupler (C-43) | 280 |
| | Color developing agent (EXCD-1) | 240 |
| | Antifoggant (5) | 8 |
| | High-boiling solvent (6) | 410 |
| | Surface-active agent (7) | 40 |
| | Water-soluble polymer (11) | 20 |
| Transparent PET base (102 μm) | | |

The procedure for the preparation of 601 was repeated, except that the color-developing agent and the couplers were changed as shown in Table 15, thereby producing photographic materials 602 to 622. The thus prepared light-sensitive material was subjected to gradation exposure through B, G, and R filters, whose density were changed continuously, for sensitometry using an FWH sensitometer (the color temperature of the light source of which was 3200° K), manufactured by Fuji Photo Film Co., Ltd.

After the exposed light-sensitive material was immersed in water for 2.5 sec, with the water kept at 40° C., it was squeezed by a roller and was immediately placed to bring the coated surface and a processing sheet R401 in contact with each other.

By using a heat drum, whose temperature was regulated to bring the temperature of the water-absorbed coated surface to 80° C., they were heated for 30 sec, and when the processing sheet was pulled out of the light-sensitive material, cyan, magenta, and yellow color images corresponding to the filters used for the exposure were obtained clearly on the light-sensitive material.

Immediately after the processing, the densities of the maximum density section (Dmax) and the minimum density section (Dmin) of the sample were measured by an X-LITE densitometer. The results are shown in Table 16.

The constitutions of the processing sheet R401 and the support A used are shown in Tables 13 and 14.

TABLE 13

| Number of layer | Additive | Coated amount (mg/m²) |
|---|---|---|
| Fourth layer | Acid-processed gelatin | 220 |
| | Water soluble polymer (1) | 60 |
| | Water soluble polymer (2) | 200 |
| | Additive (1) | 80 |
| | Palladium sulfide | 3 |
| | Potassium nitrate | 12 |
| | Matting agent (1) | 10 |
| | Anionic surface-active agent(1) | 7 |
| | Anionic surface-active agent (2) | 7 |
| | Ampholytic surface-active agent (1) | 10 |
| Third layer | Lime-processed gelatin | 240 |
| | Water soluble polymer (2) | 24 |
| | Hardening agent (1) | 180 |
| | Anionic surface-active agent (3) | 9 |
| Second layer | Lime-processed gelatin | 2400 |
| | Water soluble polymer (2) | 360 |
| | Water soluble polymer (3) | 700 |
| | Water soluble polymer (4) | 600 |
| | High boiling solvent (1) | 2000 |
| | Additive (2) | 20 |
| | Potassium hydantoin | 260 |
| | Guanidine picolinic acid salt | 2910 |
| | Potassium quinolinic acid salt | 225 |
| | Sodium quinolinic acid salt | 180 |
| | Anionic surface-active agent (3) | 24 |
| First layer | Gelatin | 280 |
| | Water soluble polymer (1) | 12 |
| | Anionic surface-active agent (1) | 14 |
| | Hardening agent (1) | 185 |
| Support | PET support A (thickness 63 μm) | |

TABLE 14

| | Constitution of support A | |
|---|---|---|
| Name of layer | Composition | Weight (mg/m²) |
| Surface undercoat layer | Gelatin | 100 |
| Polymer layer | Polyethylene telephthlate | 62500 |
| Backing undercoat | Methyl methacrylate/styrene/2- | |

TABLE 14-continued

| | Constitution of support A | |
|---|---|---|
| Name of layer | Composition | Weight (mg/m²) |
| layer | ethylhexyl acrylate/methacrylic acid copolymer | 1000 |
| | PMMA layer (average grain diameter 12 μm) | 120 |
| | | 63720 |

| | |
|---|---|
| Water-soluble polymer (1) | κ - Carrageenan |
| Water-soluble polymer (2) | Sumikagel L5H (trade name: manufactured by Sumitomo Kagaku Co.) |
| Water-soluble polymer (3) | Dextran (molecular weight 70,000) |
| Water-soluble polymer (4) | MP polymer MP102 (trade name: manufactured by Kurare Co.) |

Additive (1)

$$\begin{array}{c} N-N \\ \parallel \quad \diagdown \\ N \quad \diagup \\ \diagdown N \diagup \quad SH \end{array}$$

─⟨C₆H₄⟩─SO₃Na

Additive (2)

$$C_4H_9OOC\diagdown \diagdown N-OH$$
$$C_4H_9OOC\diagup \diagup$$

Hardening agent (1)

$$\begin{array}{c} O \diagdown \diagdown O \diagdown \diagdown O \diagdown \diagdown \\ \diagup O \quad \quad \quad \quad \quad O \diagup \end{array}$$

Anionic surface-active agent (1)

$$\begin{array}{c} \quad\quad\quad O \quad\quad\quad C_2H_5 \\ \quad\quad\quad \parallel \quad\quad\quad | \\ \quad\quad\diagdown O \diagdown CH-C_4H_9 \\ NaO_3S \\ \quad\quad\quad \parallel \quad\quad\quad | \\ \quad\quad\quad O \quad\quad\quad C_2H_5 \\ \quad\quad\quad\quad\quad\quad C_4H_9 \end{array}$$

Anionic surface-active agent (2)

$$\begin{array}{c} O \\ \parallel \\ C_8F_{17}-S-CH_2-COOK \\ \parallel \\ O \quad C_3H_7 \end{array}$$

Anionic surface-active agent (3)

$C_{13}H_{27}$─⟨C₆H₄⟩─SO₃Na

-continued

| Ampholytic surface-active agent (1) | High-boiling solvent (1) | |
|---|---|---|
| 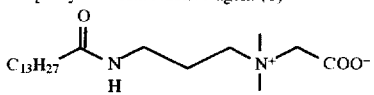 | EMPARA 40 (trade name: manufactured by Ajinomoto K.K.) | 5 |
| | Matting agent (1) SYLOID79 (trade name: manufactured by Fuji Davisson Co.) | 10 |

TABLE 15

| | | Cyan | | | Magenta | | | Yellow | | |
|---|---|---|---|---|---|---|---|---|---|---|
| Sample No. | | Coupler | Color developing agent | Added amount | Coupler | Color developing agent | Added amount | Coupler | Color developing agent | Added amount |
| 601 | (Comparative Example) | C-43 | EXCD-1 | 1.0 | C-40 | EXCD-1 | 1.0 | C-21 | EXCD-1 | 1.0 |
| 602 | (") | " | " | 2.0 | " | " | 2.0 | " | " | 2.0 |
| 603 | (") | C-41 | " | 1.0 | C-47 | " | 1.0 | " | " | 1.0 |
| 604 | (") | " | " | 2.0 | " | " | 2.0 | " | " | 2.0 |
| 605 | (This Invention) | C-43 | (57) | 1.0 | C-40 | (57) | 1.0 | " | (57) | 1.0 |
| 606 | (") | " | (47) | 1.0 | " | (47) | 1.0 | " | (47) | 1.0 |
| 607 | (") | " | (38) | 1.0 | " | (38) | 1.0 | " | (38) | 1.0 |
| 608 | (") | " | (36) | 1.0 | " | (36) | 1.0 | " | (36) | 1.0 |
| 609 | (") | " | (36) | 2.0 | " | (36) | 2.0 | " | (36) | 2.0 |
| 610 | (") | " | (52) | 1.0 | " | (52) | 1.0 | " | (52) | 1.0 |
| 611 | (") | C-41 | (14) | 1.0 | C-47 | (14) | 1.0 | " | (14) | 1.0 |
| 612 | (") | " | (13) | 1.0 | " | (13) | 1.0 | " | (13) | 1.0 |
| 613 | (") | " | (3) | 1.0 | " | (3) | 1.0 | " | (3) | 1.0 |
| 614 | (") | " | (1) | 1.0 | " | (1) | 1.0 | " | (1) | 1.0 |
| 615 | (") | " | (1) | 2.0 | " | (1) | 2.0 | " | (1) | 2.0 |
| 616 | (") | " | (24) | 1.0 | " | (24) | 1.0 | " | (24) | 1.0 |
| 617 | (Comparative Example) | C-41 | EXCD-1 | 1.0 | C-27 | EXCD-1 | 1.0 | C-2 | EXCD-1 | 1.0 |
| 618 | (This Invention) | " | (71) | 1.0 | " | (71) | 1.0 | " | (71) | 1.0 |
| 619 | (") | " | (73) | 1.0 | " | (73) | 1.0 | " | (73) | 1.0 |
| 620 | (Comparative Example) | C-43 | EXCD-1 | 1.0 | C-56 | EXCD-1 | 1.0 | C-77 | EXCD-1 | 1.0 |
| 621 | (This Invention) | " | (36) | 1.0 | " | (36) | 1.0 | " | (36) | 1.0 |
| 622 | (") | " | (68) | 1.0 | " | (68) | 1.0 | " | (68) | 1.0 |

The added amount is expressed in a molar ratio to the color developing agent in each layer of the light-sensitive material 601.

TABLE 16

| | | Before storage | | | | | |
|---|---|---|---|---|---|---|---|
| | | Cyan | | Magenta | | Yellow | |
| Sample No. | | Dmax | Dmin | Dmax | Dmin | Dmax | Dmin |
| 601 | (Comparative Example) | 0.22 | 0.20 | 0.26 | 0.21 | 0.31 | 0.23 |
| 602 | (Comparative Example) | 0.23 | 0.21 | 0.26 | 0.21 | 0.32 | 0.25 |
| 603 | (Comparative Example) | 0.22 | 0.20 | 0.26 | 0.22 | 0.28 | 0.22 |
| 604 | (Comparative Example) | 0.25 | 0.23 | 0.30 | 0.24 | 0.30 | 0.23 |
| 605 | (This Invention) | 0.64 | 0.20 | 0.55 | 0.20 | 0.62 | 0.26 |
| 606 | (This Invention) | 1.00 | 0.21 | 1.03 | 0.35 | 1.12 | 0.80 |
| 607 | (This Invention) | 1.32 | 0.22 | 1.28 | 0.21 | 1.35 | 0.25 |
| 608 | (This Invention) | 1.40 | 0.23 | 1.42 | 0.24 | 1.50 | 0.26 |
| 609 | (This Invention) | 1.48 | 0.22 | 1.47 | 0.25 | 1.52 | 0.29 |
| 610 | (This Invention) | 0.36 | 0.20 | 0.35 | 0.24 | 0.35 | 0.24 |
| 611 | (This Invention) | 0.46 | 0.21 | 0.55 | 0.24 | 0.44 | 0.23 |
| 612 | (This Invention) | 0.71 | 0.22 | 0.83 | 0.23 | 0.80 | 0.24 |
| 613 | (This Invention) | 1.42 | 0.22 | 1.30 | 0.27 | 1.44 | 0.21 |
| 614 | (This Invention) | 1.51 | 0.22 | 1.42 | 0.26 | 1.50 | 0.28 |
| 615 | (This Invention) | 1.55 | 0.22 | 1.50 | 0.26 | 1.58 | 0.30 |
| 616 | (This Invention) | 0.34 | 0.24 | 0.30 | 0.22 | 0.30 | 0.24 |
| 617 | (Comparative Example) | 0.25 | 0.23 | 0.27 | 0.24 | 0.29 | 0.24 |

TABLE 16-continued

| | | Before storage | | | | | |
|---|---|---|---|---|---|---|---|
| | | Cyan | | Magenta | | Yellow | |
| Sample No. | | Dmax | Dmin | Dmax | Dmin | Dmax | Dmin |
| 618 | (This Invention) | 1.49 | 0.21 | 1.49 | 0.28 | 1.52 | 0.30 |
| 619 | (This Invention) | 1.38 | 0.23 | 1.41 | 0.26 | 1.50 | 0.28 |
| 620 | (Comparative Example) | 0.24 | 0.21 | 0.23 | 0.22 | 0.28 | 0.25 |
| 621 | (This Invention) | 1.57 | 0.25 | 1.48 | 0.24 | 1.48 | 0.24 |
| 622 | (This Invention) | 1.52 | 0.24 | 1.41 | 0.28 | 1.54 | 0.25 |

Summarizing the results shown in Table 16, it can be understood that, similarly to Example 3, in the photographic materials 601 to 604, 617, and 620, which use color-developing agents of Comparative Examples, images excellent in discrimination cannot be obtained, while in the photographic materials 605 to 616, 618, 619, 621, and 622, which use color-developing agents of the present invention, images excellent in discrimination can be obtained. In this Example, the effect of the present invention is also apparent.

Example 5

The procedure for preparing Sample (100) in Example 1 was repeated, except that the color-developing agent was not added and the couplers were changed to the couplers shown in Table 17, in the same molar amounts, thereby preparing Samples (700) to (702). (With respect to silver chlorobromide emulsions, in Sample (700), the silver chlorobromide emulsion A used in Example 1 was used; in Sample (701), the silver chlorobromide B used in Example 1 was used; and in Sample (702), the silver chlorobromide C used in Example 1 was used.)

By using an FWH-type sensitometer (color temperature of the light source: 3,200° K), manufactured by Fuji Photo Film Co., Ltd., gradation exposure was given to the thus prepared Sample (700) through a blue filter for sensitometry, to the thus prepared Sample (701) through a green filter for sensitometry, and to the thus prepared Sample (702) through a red filter for sensitometry.

The thus exposed Samples were processed with the following processing solutions in the following processing steps:

| Processing step | Temperature | Time |
|---|---|---|
| Development | 40° C. | 45 sec |
| Bleach-fix | 40° C. | 45 sec |
| Rinse | room temperature | 45 sec |
| Alkali processing | room temperature | 30 sec |

(Developing Solution)

| Water | 800 ml |
|---|---|
| Potassium phosphate | 40 g |
| Disodium N,N-bis(sulfonatoethyl)hydroxylamine | 10 g |
| KCl | 5 g |
| Hydroxylethylidene-1,1-disulfonic acid (30%) | 4 ml |
| Color developing agent (18) | 2 g |
| Water to make | 1,000 ml |
| pH (at 25° C. by using potassium hydroxide) | 12.0 |

(Bleach-fix Solution)

| Water | 600 ml |
|---|---|
| Ammonium thiosulfate (700 g/liter) | 93 ml |

-continued

| Ammonium sulfite | 40 ml |
|---|---|
| Ethylenediaminetetraacetic acid iron (III) ammonium salt | 55 g |
| Ethylenediamintetraacetic acid | 2 g |
| Nitric acid (67%) | 30 g |
| Water to make | 1,000 ml |
| pH (at 25° C. by using acetic acid and ammonia water) | 5.8 |

(Rinsing Solution)

| Sodium chlorinated isocyanurate | 0.02 g |
|---|---|
| Deionized water (conductivity: 5 µS/cm or below) | 1,000 ml |
| pH | 6.5 |

(Alkali Processing Solution)

| Water | 800 ml |
|---|---|
| Potassium cabonate | 30 g |
| Water to make | 1,000 ml |
| pH (at 25° C. by using sulfuric acid) | 10.0 |

The above processing was repeated for Samples (700) to (702), except that the color-developing agent (18) in the developing solution was changed to the color-developing agents shown in Table 17, in the same molar amount.

TABLE 17

| Sample No. | Coupler | Color developing agent |
|---|---|---|
| 700 | C-21 | (18) |
| | | (26) |
| | | (40) |
| 701 | C-40 | (18) |
| | | (26) |
| | | (40) |
| 702 | C-43 | (18) |
| | | (26) |
| | | (40) |

In all the cases of the processing solution containing the color-developing agent (18), the processing solution containing the color-developing agent (26), and the processing solution containing the color-developing agent (40), the Sample (700) gave an excellent yellow image, image-wise, the Sample (701) gave an excellent magenta image, image-wise, and the Sample (702) gave an excellent cyan image, image-wise.

Example 6 (Comparative example)

Example 1 was repeated to prepare silver halide light-sensitive materials, except that, in Samples (100), (200), and (300), instead of the color-developing agent (EXCD-1), Compound 3-42 (a compound whose σ values' sum was less than 0.80), described in JP-A No. 310555/1990, and Compound (2)-6 (a compound whose σ values' sum was less than 0.80), described in JP-A No. 165171/1993, were used in the same molar amount. These six light-sensitive materials were developed in the same way as in Example 1, and the maximum color density was measured, and the Dmax values were less than 0.20.

Example 7 (Comparative example)

Example 3 for the preparation of the light-sensitive material 501 was repeated, except that, instead of the color-developing agent (EXCD-1) in the first layer, the third layer, and the fifth layer, Compound 3-42, described in JP-A No.310555/1990, or Compound (2)-6, described in JP-A No.165171/1993, was used in the same molar amount, thereby preparing heat-processible color light-sensitive materials. These two light-sensitive materials were developed similarly to Example 3, and the Dmax value and the Dmin value of the cyan, magenta, and yellow were measured. The Dmin values were in the order of 0.20, but the Dmax values were less than 0.25.

Having described our invention as related to the present embodiments, it is our intention that the invention not be limited by any of the details of the description, unless otherwise specified, but rather be construed broadly within its spirit and scope as set out in the accompanying claims.

What we claim is:

1. A silver halide photographic light-sensitive material, comprising a compound represented by formula (V) or (VI):

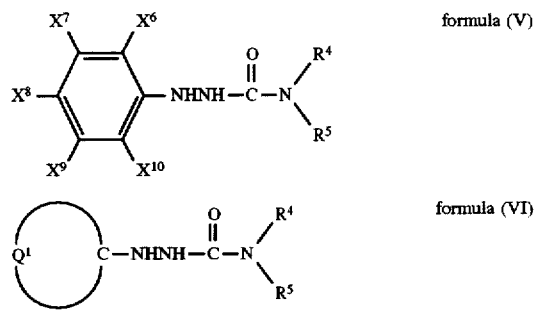

wherein $R^4$ and $R^5$ each represent a hydrogen atom or a substituent, and at least one of $R^4$ and $R^5$ is a hydrogen atom ; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.20 or more but 3.80 or below;

$Q^1$ represents a group of nonmetal atoms required to form, together with the C, a nitrogen-containing 5-membered to 8-membered heterocyclic ring.

2. The silver halide photographic light-sensitive material as claimed in claim 1, wherein the light-sensitive material contains at least one coupler.

3. The silver halide photographic light-sensitive material according to claim 1, wherein $R^4$ and $R^5$ in formulas (V) and (VI) each represent a hydrogen atom, a straight-chain alkyl group, a branched-chain alkyl group, or a cycloalkyl group, having 1 to 50 carbon atoms; a straight-chain alkenyl group, a branched-chain alkenyl group, or a cycloalkenyl group, having 2 to 50 carbon atoms; an alkynyl group having a total of 2 to 50 carbon atoms, an aryl group having 6 to 50 carbon atoms, an acyloxy group having 1 to 50 carbon atoms, a carbamoyloxy group having 1 to 50 carbon atoms, a carbonamido group having 1 to 50 carbon atoms, a sulfonamido group having 1 to 50 carbon atoms, a carbamoyl group having 1 to 50 carbon atoms, a sulfamoyl group having 0 to 50 carbon atoms, an alkoxy group having 1 to 50 carbon atoms, an aryloxy group having 6 to 50 carbon atoms, an aryloxycarbonyl group having 7 to 50 carbon atoms, an alkoxycarbonyl group having 2 to 50 carbon atoms, an N-acylsulfamoyl group having 1 to 50 carbon atoms, an alkylsulfonyl group having 1 to 50 carbon atoms, an arylsulfonyl group having 6 to 50 carbon atoms, an alkoxycarbonylamino group having 2 to 50 carbon atoms, an aryloxycarbonylamino group having 7 to 50 carbon atoms, an amino group having 0 to 50 carbon atoms, a cyano group, a nitro group, a carboxyl group, a hydroxy group, a sulfo group, a mercapto group, an alkylsulfinyl group having 1 to 50 carbon atoms, an arylsulfinyl having 6 to 50 carbon atoms, an alkylthio group having 1 to 50 carbon atoms, an arylthio group having 6 to 50 carbon atoms, a ureido group having 1 to 50 carbon atoms, a heterocyclic group having 2 to 50 carbon atoms, an acyl group having 1 to 50 carbon atoms, a sulfamoylamino group having 0 to 50 carbon atoms, a silyl group having 3 to 50 carbon atoms, or a halogen atom.

4. The silver halide photographic light-sensitive material according to claim 2, wherein the color developing agent is present in an amount of 0.01 to 100 times the amount of the coupler.

5. The silver halide photographic light-sensitive material according to claim 1, wherein the compound represented by formula (V) or (VI) is a color developing agent.

6. The silver halide photographic light-sensitive material of claim 1, wherein said compound represented by formula (V) or (VI) is contained in at least one hydrophilic colloid layer placed on a base.

7. The silver halide photographic light-sensitive material according to claim 1, wherein for $X^6$ through $X^{10}$, the substituent is a straight-chain alkyl group, a branched-chain alkyl group, or a cycloalkyl group, having 1 to 50 carbon atoms; a straight-chain alkenyl group, a branched-chain alkenyl group, or a cycloalkenyl group, having 2 to 50 carbon atoms; an alkenyl group having a total of 2 to 50 carbon atoms, an aryl group having 6 to 50 carbon atoms, an acyloxy group having 1 to 50 carbon atoms, a carbanoyloxy group having 1 to 50 carbon atoms, a carbonamido group having 1 to 50 carbon atoms, a sulfonamide group having 1 to 50 carbon atoms, a carbamoyl group having 1 to 50 carbon atoms, a sulfamoyl group having 0 to 50 carbon atoms, an alkoxy group having 1 to 50 carbon atoms, an aryloxy group having 6 to 50 carbon atoms, an aryloxycarbonyl group having 7 to 50 carbon atoms, an alkoxycarbonyl group having 2 to 50 carbon atoms, an N-acylsulfamoyl group having 1 to 50 carbon atoms, an alkylsulfonyl group having 1 to 50 carbon atoms, an arylsulfonyl group having 6 to 50 carbon atoms, an alkoxycarbonylamino group having 2 to 50 carbon atoms, an aryloxycarbonylamino group having 7 to 50 carbon atoms, an amino group having 0 to 50 carbon atoms, a cyano group, a nitro group, a carboxyl group, a hydroxy group, a sulfo group, a mercapto group, an alkylsulfinyl group having 1 to 50 carbon atoms, an arylsulfinyl having 6 to 50 carbon atoms, an alkylthio group having 1 to 50 carbon atoms, an arylthio group having 6 to 50 carbon atoms, a ureido group having 1 to 50 carbon atoms, a heterocyclic group having 2 to 50 carbon atoms, an acyl group having 1 to 50 carbon atoms, a sulfamoylamino group having 0 to 50 carbon atoms, a silyl group having 3 to 50 carbon atoms, or a halogen atom.

8. A silver halide photographic light-sensitive material, comprising a compound represented by formula (V) or (VII):

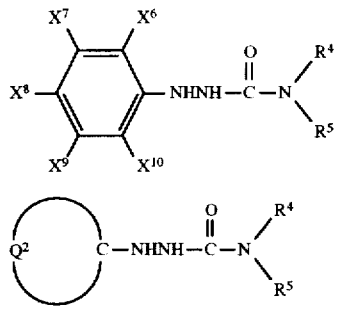

formula (V)

formula (VII)

wherein $R^4$ and $R^5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.50 or more but 3.80 or below;

$Q^2$ represents a group of nonmetal atoms required to form, together with the C, a nitrogen-containing 5-membered to 8-membered heterocyclic ring, to which a benzene ring or a heterocyclic ring is condensed.

9. The silver halide photographic light-sensitive material according to claim 8, wherein $R^4$ and $R^5$ in formula (V) and (VII) each represent a hydrogen atom, a straight-chain alkyl group, a branched-chain alkyl group, or a cycloalkyl group, having 1 to 50 carbon atoms; a straight-chain alkenyl group, a branched-chain alkenyl group, or a cycloalkenyl group, having 2 to 50 carbon atoms; an alkynyl group having a total of 2 to 50 carbon atoms, an aryl group having 6 to 50 carbon atoms, an acyloxy group having 1 to 50 carbon atoms, a carbamoyloxy group having 1 to 50 carbon atoms, a carbonamido group having 1 to 50 carbon atoms, a sulfonamido group having 1 to 50 carbon atoms, a carbamoyl group having 1 to 50 carbon atoms, a sulfamoyl group having 0 to 50 carbon atoms, an alkoxy group having 1 to 50 carbon atoms, an aryloxy group having 6 to 50 carbon atoms, an aryloxycarbonyl group having 7 to 50 carbon atoms, an alkoxycarbonyl group having 2 to 50 carbon atoms, an N-acylsulfamoyl group having 1 to 50 carbon atoms, an alkylsulfonyl group having 1 to 50 carbon atoms, an arylsulfonyl group having 6 to 50 carbon atoms, an alkoxycarbonylamino group having 2 to 50 carbon atoms, an aryloxycarbonylamino group having 7 to 50 carbon atoms, an amino group having 0 to 50 carbon atoms, a cyano group, a nitro group, a carboxyl group, a hydroxy group, a sulfo group, a mercapto group, an alkylsulfinyl group having 1 to 50 carbon atoms, an arylsulfinyl having 6 to 50 carbon atoms, an alkylthio group having 1 to 50 carbon atoms, an arylthio group having 6 to 50 carbon atoms, a ureido group having 1 to 50 carbon atoms, a heterocyclic group having 2 to 50 carbon atoms, an acyl group having 1 to 50 carbon atoms, a sulfamoylamino group having 0 to 50 carbon atoms, a silyl group having 3 to 50 carbon atoms, or a halogen atom.

10. The silver halide photographic light-sensitive material according to claim 8, wherein the compound represented by formula (V) or (VII) is a color developing agent.

11. The silver halide photographic light-sensitive material as claimed in claim 8, wherein the light-sensitive material contains at least one coupler.

12. The silver halide photographic light-sensitive material according to claim 8, wherein for $X^6$ through $X^{10}$, the substituent is a straight-chain alkyl group, a branched-chain alkyl group, or a cycloalkyl group, having 1 to 50 carbon atoms; a straight-chain alkenyl group, a branched-chain alkenyl group, or a cycloalkenyl group, having 2 to 50 carbon atoms; an alkenyl group having a total of 2 to 50 carbon atoms, an aryl group having 6 to 50 carbon atoms, an acyloxy group having 1 to 50 carbon atoms, a carbanoyloxy group having 1 to 50 carbon atoms, a carbonamido group having 1 to 50 carbon atoms, a sulfonamide group having 1 to 50 carbon atoms, a carbamoyl group having 1 to 50 carbon atoms, a sulfamoyl group having 0 to 50 carbon atoms, an alkoxy group having 1 to 50 carbon atoms, an aryloxy group having 6 to so carbon atoms, an aryloxycarbonyl group having 7 to 50 carbon atoms, an alkoxycarbonyl group having 2 to 50 carbon atoms, an N-acylsulfamoyl group having 1 to 50 carbon atoms, an alkylsulfonyl group having 1 to 50 carbon atoms, an arylsulfonyl group having 6 to 50 carbon atoms, an alkoxycarbonylamino group having 2 to 50 carbon atoms, an aryloxycarbonylamino group having 7 to 50 carbon atoms, an amino group having 0 to 50 carbon atoms, a cyano group, a nitro group, a carboxyl group, a hydroxy group, a sulfo group, a mercapto group, an alkylsulfinyl group having 1 to 50 carbon atoms, an arylsulfinyl having 6 to 50 carbon atoms, an alkylthio group having 1 to 50 carbon atoms, an arylthio group having 6 to 50 carbon atoms, a ureido group having 1 to 50 carbon atoms, a heterocyclic group having 2 to 50 carbon atoms, an acyl group having 1 to 50 carbon atoms, a sulfamoylamino group having 0 to 50 carbon atoms, a silyl group having 3 to 50 carbon atoms, or a halogen atom.

13. The silver halide photographic light-sensitive material of claim 8, wherein said compound represented by formula (V) or (VII) is contained in at least one hydrophilic colloid layer placed on a base.

14. A method of forming an image comprising developing a silver halide photographic light-sensitive material in the presence of a color-developing agent represented by formula (V) or (VI):

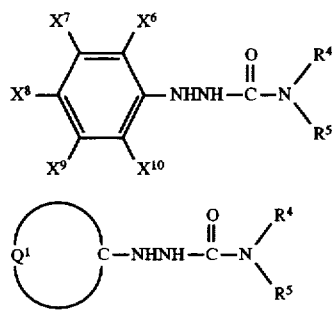

formula (V)

formula (VI)

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.20 or more but 3.80 or below;

$Q^1$ represents a group of nonmetal atoms required to form, together with the C, a nitrogen-containing 5-membered to 8-membered heterocyclic ring.

15. The method of forming an image as claimed in claim 14, wherein the light-sensitive material has been image-wise exposed to light before the development thereof.

16. The method of forming an image as claimed in claim 14, which comprises carrying out development by heating the light-sensitive material at 65° C. to 180° C., wherein the light-sensitive material comprises a compound represented by formula (V) or (VI):

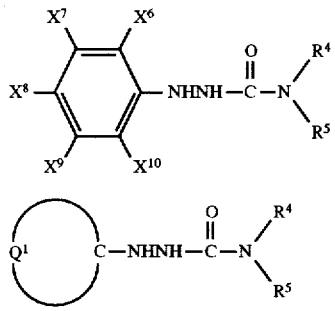

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.20 or more but 3.80 or below;

$Q^1$ represents a group of nonmetal atoms required to form, together with the C, a nitrogen-containing 5-membered to 8-membered heterocyclic ring to which a benzene ring or a heterocyclic ring is condensed.

17. The method of forming an image as claimed in claim 14 which comprises carrying out development of the light-sensitive material in a solution, wherein the light-sensitive material comprises a compound represented by formula (V) or (VI):

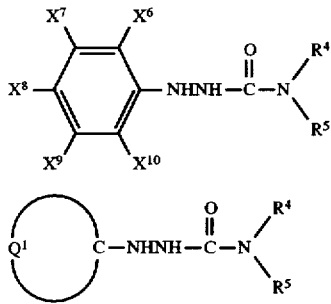

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.20 or more but 3.80 or below;

$Q^1$ represents a group of nonmetal atoms required to form, together with the C, a nitrogen-containing 5-membered to 8-membered heterocyclic ring.

18. The method of forming an image as claimed in claim 14, which comprises carrying out development of the light-sensitive material with a processing solution containing a color-developing agent represented by the following formula (V) or (VI):

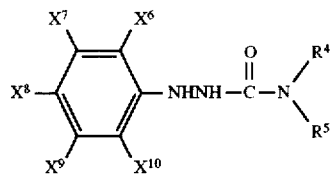

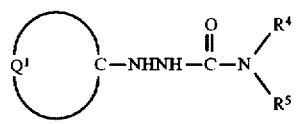

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.20 or more but 3.80 or below;

$Q^1$ represents a group of nonmetal atoms required to form, together with the C, a nitrogen-containing 5-membered to 8-membered heterocyclic ring.

19. A method of forming an image comprising developing a silver halide photographic light-sensitive material in the presence of a color-developing agent represented by formula (V) or (VII):

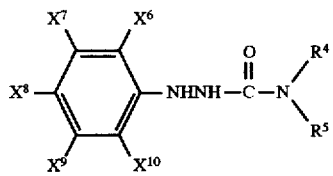

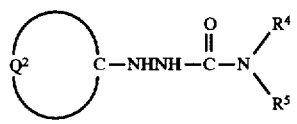

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.50 or more but 3.80 or below;

$Q^2$ represents a group of nonmetal atoms required to form, together with the C, a nitrogen-containing 5-membered to 8-membered heterocyclic ring, to which a benzene ring or a heterocyclic ring is condensed.

20. The method of forming an image as claimed in claim 19, which comprises carrying out development by heating the light-sensitive material at 65° C. to 180° C., wherein the light-sensitive material comprises a compound represented by formula (V) or (VII):

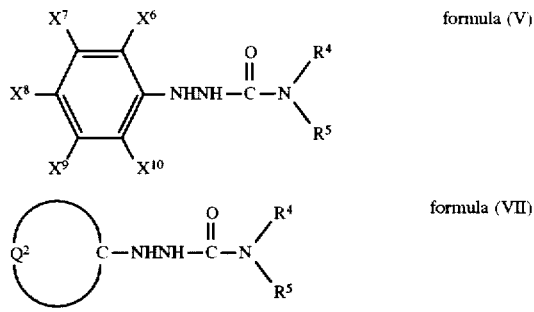

formula (V)

formula (VII)

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.50 or more but 3.80 or below;

$Q^2$ represents a group of nonmetal atoms required to form, together with the C, a nitrogen-containing 5-membered to 8-membered heterocyclic ring, to which a benzene ring or a heterocyclic ring is condensed.

21. The method of forming an image as claimed in claim 19, which comprises carrying out development of the light-sensitive material in a solution, wherein the light-sensitive material comprises a compound represented by formula (V) or (VII):

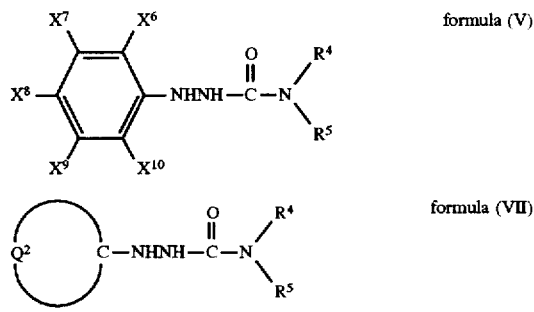

formula (V)

formula (VII)

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.50 or more but 3.80 or below;

$Q^2$ represents a group of nonmetal atoms required to form, together with the C, a nitrogen-containing 5-membered to 8-membered heterocyclic ring, to which a benzene ring or a heterocyclic ring is condensed.

22. The method of forming an image as claimed in claim 19, which comprises carrying out development of the light-sensitive material with a processing solution containing a color-developing agent represented by the following formula (V) or (VII):

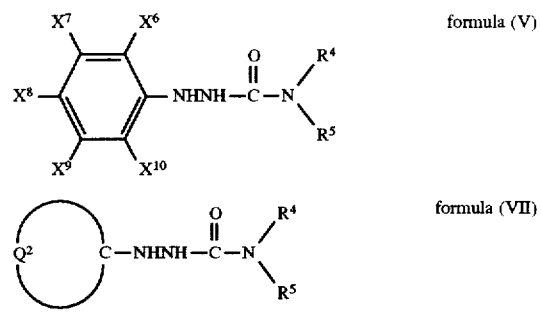

formula (V)

formula (VII)

wherein $R_4$ and $R_5$ each represent a hydrogen atom or a substituent, and at least one of $R^4$ and $R^5$ is a hydrogen atom; and $X^6$, $X^7$, $X^8$, $X^9$, and $X^{10}$ each represent a hydrogen atom, a cyano group, a sulfonyl group, a sulfinyl group, a sulfamoyl group, a carbamoyl group, an alkoxycarbonyl group, an aryloxycarbonyl group, an acyl group, a trifluoromethyl group, a halogen atom, an acyloxy group, an acylthio group, or a heterocyclic group, provided that the sum of the Hammett substituent constant σp values of $X^6$, $X^8$, and $X^{10}$ and the Hammett substituent constant σm values of $X^7$ and $X^9$ is 1.50 or more but 3.80 or below;

$Q^2$ represents a group of nonmetal atoms required to form, together with the C, a nitrogen-containing 5-membered to 8-membered heterocyclic ring, to which a benzene ring or a heterocyclic ring is condensed.

23. The method of forming an image as claimed in claim 19, wherein the light-sensitive material has been image-wise exposed to light before the development thereof.

* * * * *